US012622967B2

(12) United States Patent
Brooks et al.

(10) Patent No.: US 12,622,967 B2
(45) **Date of Patent: *May 12, 2026**

(54) MOLECULES, FORMULATIONS, AND METHODS FOR NUTRITIONAL SUPPORT OF ATHLETES, PATIENTS, AND OTHERS

(71) Applicant: Today, Inc., Seattle, WA (US)

(72) Inventors: George A. Brooks, Seattle, WA (US); Michael A. Horning, San Francisco, CA (US); Iñigo San Millán, Littleton, CO (US)

(73) Assignee: Today, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/668,190

(22) Filed: May 19, 2024

(65) Prior Publication Data

US 2024/0299548 A1 Sep. 12, 2024

Related U.S. Application Data

(63) Continuation of application No. 18/096,794, filed on Jan. 13, 2023, now Pat. No. 12,023,382.

(60) Provisional application No. 63/300,563, filed on Jan. 18, 2022.

(51) Int. Cl.

| | |
|---|---|
| ***A61K 31/277*** | (2006.01) |
| ***A23L 33/12*** | (2016.01) |
| ***A61K 47/10*** | (2017.01) |

(52) U.S. Cl.

CPC .............. *A61K 47/10* (2013.01); *A23L 33/12* (2016.08)

(58) Field of Classification Search

CPC ...... A61K 31/4174; A61K 9/006; A61K 9/06; A61K 9/08; A61K 9/12; A61P 25/28

See application file for complete search history.

(56) References Cited

U.S. PATENT DOCUMENTS

| | | | | |
|---|---|---|---|---|
| 6,743,821 | B2 * | 6/2004 | Brooks | A61K 31/22 514/546 |
| 7,807,718 | B2 * | 10/2010 | Hashim | A61P 25/28 514/552 |
| 10,792,269 | B2 * | 10/2020 | Hashim | A61K 31/225 |
| 2023/0151395 | A1 * | 5/2023 | Lochmann | A61P 3/04 514/547 |

OTHER PUBLICATIONS

White et al. (A Systematic Review of Intravenous ß-Hydroxybutyrate Use in Humans—A Promising Future Therapy? Front Med (Lausanne). Sep. 21, 2021;8:740374. doi: 10.3389/fmed.2021.740374. PMID: 34621766; PMCID: PMC8490680.).*

* cited by examiner

*Primary Examiner* — Layla Soroush
(74) *Attorney, Agent, or Firm* — Robert H Lee

(57) ABSTRACT

The present invention relates to nutritional formulations for increasing sports and other physical performance and that have beneficial effects on health and wellness for various populations. The invention includes molecular compounds as disclosed. A preferred embodiment is a molecule type based on a glycerol backbone, with three glycerol functional groups $B_1$, $B_2$, $B_3$, wherein one or more of the B groups may correspond to one of the functional energy groups $A_1$, $A_2$ or $A_3$, as disclosed. The invention includes nutritional formulations, some based on the inventive molecular compounds. The invention also includes method of using, administering, and implementing the above, including computer implemented and computer assisted methods.

6 Claims, 88 Drawing Sheets

| **Example Formula #1** | | | |
|---|---|---|---|
| Solute | Total g/L | % Total | |
| Sodium L-(+)-Lactate | 16.2 | 16.2% | |
| Sodium L-(+)-pyruvate | 0.8 | 0.8% | Alternatives: Calcium Pyruvate and Magnesium Pyruvate |
| Sodium D-Acetoacetate | 0.92 | 0.92% | Alternative: Sodium Beta Hydroxybutyrate |
| Potassium L-(+)-Lactate | 0.52 | 0.52% | |
| Calcium L-(+)-Lactate | 0.99 | 0.99% | |
| Magnesium L-(+)-Lactate | 0.564 | 0.56% | |
| Monosodium phosphate | 0.07 | 0.07% | |
| | | | |
| Fructose | 20 | 19.95% | |
| Glucose | 20 | 19.95% | |
| Maltodextrin | 20 | 19.95% | |
| TOTAL | 100.2 | | |

FIG. 1

| **Example Formula #2** | | | |
|---|---|---|---|
| Solute | Total g/L | % Total | |
| Sodium L-(+)-Lactate | 17.15 | 17.12% | |
| Sodium L-(+)-pyruvate | 0.8 | 0.80% | |
| Sodium Acetoacetate | 0 | 0.00% | Alternative: Sodium Beta Hydroxybutyrate |
| Potassium L-(+)-Lactate | 0.52 | 0.52% | |
| Calcium L-(+)-Lactate | 0.99 | 0.99% | |
| Magnesium L-(+)-Lactate | 0.564 | 0.56% | |
| | | | |
| Fructose | 30 | 29.94% | |
| Glucose | 30 | 29.94% | |
| Maltodextrin | 0 | 0.00% | |
| TOTAL | 100.194 | | |

FIG. 2

| **Example Formula #3** | | | |
|---|---|---|---|
| Solute | Total g/L | % Total | |
| Sodium L-(+)-Lactate | 17.05 | 21.30% | |
| Sodium D Acetoacetate | 0.92 | 1.15% | Alternative: Sodium Beta Hydroxybutyrate |
| Potassium L-(+)-Lactate | 0.52 | 0.65% | |
| Calcium L-(+)-Pyruvate | 0.99 | 1.24% | |
| Magnesium L-(+)-Pyruvate | 0.564 | 0.70% | |
| | | | |
| Fructose | 20 | 24.99% | |
| Glucose | 20 | 24.99% | |
| Maltodextrin | 20 | 24.99% | |
| TOTAL | 80.044 | | |

FIG. 3

| **Example Formula #4** | | | |
|---|---|---|---|
| Solute | Total g/L | % Total | |
| Sodium L-(+)-Lactate | 17.95 | 22.43% | |
| Sodium D Acetoacetate | 0 | 0.00% | Alternative: Sodium Beta Hydroxybutyrate |
| Potassium L-(+)-Lactate | 0.52 | 0.65% | |
| Calcium L-(+)-Pyruvate | 0.99 | 1.24% | |
| Magnesium L-(+)-Pyruvate | 0.564 | 0.70% | |
| | | | |
| Fructose | 30 | 37.49% | |
| Glucose | 30 | 37.49% | |
| Maltodextrin | 0 | 0.00% | |
| TOTAL | 80.024 | | |

FIG. 4

| **Example Formula #5** | | | |
|---|---|---|---|
| Solute | Total g/L | % Total | |
| Sodium L-(+)-Lactate | 16.25 | 16.21% | |
| Sodium L-(+)-pyruvate | 0.8 | 0.80% | Alternatives:<br>Calcium Pyruvate and<br>Magnesium Pyruvate |
| Sodium D-Acetoacetate | 0.92 | 0.92% | Alternative: Sodium Beta Hydroxybutyrate |
| Potassium L-(+)-Lactate | 0.52 | 0.52% | |
| Calcium L-(+)-Lactate | 0.99 | 0.99% | |
| Magnesium L-(+)-Lactate | 0.564 | 0.56% | |
| Monosodium phosphate | 0.073 | 0.07% | |
| | | | |
| Fructose | 60 | 59.85% | |
| Glucose | 0 | 0% | |
| Maltodextrin | 0 | 0% | |
| TOTAL | 100.234 | | |

FIG. 5

| **Example Formula #6** | | | |
|---|---|---|---|
| Solute | Total g/L | % Total | |
| Sodium L-(+)-Lactate | 17.15 | 17.12% | |
| Sodium L-(+)-pyruvate | 0.8 | 0.80% | |
| Sodium Acetoacetate | 0 | 0.00% | Alternative: Sodium Beta Hydroxybutyrate |
| Potassium L-(+)-Lactate | 0.52 | 0.52% | |
| Calcium L-(+)-Lactate | 0.99 | 0.99% | |
| Magnesium L-(+)-Lactate | 0.564 | 0.56% | |
| | | | |
| Fructose | 60 | 59.88% | |
| Glucose | 0 | 0% | |
| Maltodextrin | 0 | 0.00% | |
| TOTAL | 100.194 | | |

FIG. 6

| **Example Formula #7** | | | |
|---|---|---|---|
| Solute | Total g/L | Total (%) | |
| Sodium L-(+)-Lactate | 17.95 | 89.64 | |
| Sodium Acetoacetate | 0 | 0.00 | |
| Potassium L-(+)- Lactate | 0.52 | 2.60 | |
| Calcium L-(+)-Pyruvate | 0.99 | 4.94 | |
| Magnesium L-(+)-Pyruvate | 0.564 | 2.82 | |
| | | | |
| Fructose | 0 | 0.00 | |
| Glucose | 0 | 0.00 | |
| Maltodextrin | 0 | 0.00 | |
| TOTAL | 20.024 | | |

FIG. 7

| **Example Formula #8** | | | |
|---|---|---|---|
| Solute | Total (g/L) | Total (%) | |
| Sodium L-(+)-Lactate | 17.05 | 85.06 | |
| Sodium Acetoacetate | 0.92 | 4.59 | Alternative:<br>Sodium<br>BOHB |
| Potassium L-(+)-Lactate | 0.52 | 2.59 | |
| Calcium L-(+)-Pyruvate | 0.99 | 4.94 | |
| Magnesium L-(+)-<br>Pyruvate | 0.564 | 2.81 | |
| | | | |
| Fructose | 0 | 0.00 | |
| Glucose | 0 | 0.00 | |
| Maltodextrin | 0 | 0.00 | |
| TOTAL | 20.044 | | |

FIG. 8

| **Example Formula #9** | | |
|---|---|---|
| Solute | Total (g/L) | Total (%) |
| Sodium L-(+)-Lactate | 2.5 | 2.48% |
| Potassium L-(+)-Lactate | 0.1 | 0.07% |
| Calcium L-(+)-Pyruvate | 0.1 | 0.14% |
| Magnesium L-(+)-Pyruvate | 0.1 | 0.08% |
| | | |
| Glycerol di-lactate, mono-palmitate ester | 52.0 | 52.12% |
| Fructose | 15.0 | 15.04% |
| Glucose | 0.0 | 0.00% |
| Maltodextrin | 30.0 | 30.07% |
| TOTAL | 99.8 | |

FIG. 9

| **Example Formula #10** | | |
|---|---|---|
| Solute | Total (g/L) | Total (%) |
| Sodium L-(+)-Lactate | 2.5 | 2.51% |
| Potassium L-(+)-Lactate | 0.1 | 0.10% |
| Calcium L-(+)-Pyruvate | 0.1 | 0.10% |
| Magnesium L-(+)-Pyruvate | 0.1 | 0.10% |
| | | |
| Glycerol di-lactate, mono-palmitate ester | 52.0 | 52.10% |
| Fructose | 15.0 | 15.03% |
| Glucose | 0.0 | 0.00% |
| Glycerol di-acetate, mono-palmitate ester | 30.0 | 30.06% |
| TOTAL | 99.8 | |

FIG. 10

| **Example Formula #11** | | |
|---|---|---|
| Solute | Total (g/L) | Total (%) |
| Sodium L-(+)-Lactate | 2.5 | 2.18 |
| Potassium L-(+)-Lactate | 0.5 | 0.45 |
| Calcium L-(+)-Pyruvate | 1.0 | 0.86 |
| Magnesium L-(+)-Pyruvate | 0.6 | 0.49 |
| | | |
| Glycerol di-lactate, mono-palmitate ester | 50.0 | 43.64 |
| Fructose | 20.0 | 17.46 |
| Glucose | 20.0 | 17.46 |
| Maltodextrin | 20.0 | 17.46 |
| TOTAL | 114.6 | |

FIG. 11

| **Example Formula #12** | | |
|---|---|---|
| Solute | Total (g/L) | Total (%) |
| Sodium L-(+)-Lactate | 2.5 | 4.58% |
| Potassium L-(+)-Lactate | 0.5 | 0.95% |
| Calcium L-(+)-Pyruvate | 1.0 | 1.81% |
| Magnesium L-(+)-Pyruvate | 0.6 | 1.03% |
| | | |
| Glycerol di-lactate, mono-palmitate ester | 50.0 | 91.62% |
| Stevia | 0.0 | 0.00% |
| | | |
| | | |
| TOTAL | 54.6 | |

FIG. 12

| **Example Formula #13** | | |
|---|---|---|
| Solute | Total (g/L) | Total (%) |
| Sodium L-(+)-Lactate | 2.5 | 2.18 |
| Potassium L-(+)-Lactate | 0.5 | 0.45% |
| Calcium L-(+)-Pyruvate | 1.0 | 0.86 |
| Magnesium L-(+)-Pyruvate | 0.6 | 0.49 |
| | | |
| Glycerol di-lactate, mono-palmitate ester | 50.0 | 43.64 |
| Fructose | 20.0 | 17.46 |
| Glucose | 0 | 0 |
| Maltodextrin | 40.0 | 37.46 |
| TOTAL | 114.6 | |

FIG. 13

| **Example Formula #14** | | |
|---|---|---|
| Solute | Total (g/L) | Total (%) |
| Sodium L-(+)-Lactate | 0.5 | 0.50 |
| Potassium L-(+)-Lactate | 0.1 | 0.10 |
| Calcium L-(+)-Pyruvate | 0.2 | 0.20 |
| Magnesium L-(+)-Pyruvate | 0.1 | 0.12 |
| | | |
| Whey Protein | 50.0 | 49.54 |
| Glycerol di-lactate, mono-palmitate ester | 50.0 | 49.54 |
| Stevia | 0.0 | 0.00 |
| TOTAL | 100.9 | 100.0 |

FIG. 14

| **Example Formula #15** | | |
|---|---|---|
| Solute | Total (g/L) | Total (%) |
| Sodium L-(+)-Lactate | 2.5 | 2.3 |
| Potassium L-(+)-Lactate | 0.5 | 0.04 |
| Calcium L-(+)-Pyruvate | 1.0 | 0.08 |
| Magnesium L-(+)-Pyruvate | 0.6 | 0.05 |
| | | |
| Arginyl-Lactate | 20.0 | 18 |
| Arginyl-Acetoacetate | 20.0 | 18 |
| Arginyl-Beta Hydroxy Butyrate | 20.0 | 18 |
| Maltodextrin | 45.0 | 40.6 |
| TOTAL | 109.6 | |

FIG. 15

| **Example Formula #16** | | |
| --- | --- | --- |
| Solute | Total (g/L) | Total (%) |
| Sodium L-(+)-Lactate | 0.5 | 0.50 |
| Potassium L-(+)-Lactate | 0.01 | 0.01 |
| Calcium L-(+)-Pyruvate | 0.02 | 0.02 |
| Magnesium L-(+)-Pyruvate | 0.02 | 0.02 |
| | | |
| Arginyl-Lactate | 33.0 | 33.0 |
| Arginyl-Acetoacetate | 33.0 | 33.0 |
| Arginyl-Acetate | 33.0 | 33.0 |
| Stevia | 0.0 | 0.00 |
| TOTAL | 99.9 | |

FIG. 16

| **Example Formula #17** | | |
|---|---|---|
| Solute | Total (g/L) | Total (%) |
| Sodium L-(+)-Lactate | 2.5 | 2.18 |
| Potassium L-(+)-Lactate | 0.5 | 0.45 |
| Calcium L-(+)-Pyruvate | 1.0 | 0.86 |
| Magnesium L-(+)-Pyruvate | 0.6 | 0.49 |
| | | |
| Glycerol di-lactate mono-palmitate ester | 50.0 | 43.6 |
| Beta hydroxy butyrate | 20.0 | 17.5 |
| Glycerol di-acetate mono-palmitate | 20.0 | 17.5 |
| Maltodextrin | 20.0 | 17.5 |
| TOTAL | 114.6 | 100.00 |

FIG. 17

| **Example Formula #18** | | |
|---|---|---|
| Solute | Total (g/L) | Total (%) |
| Sodium L-(+)-Lactate | 2.5 | 2.18 |
| Potassium L-(+)-Lactate | 0.5 | 0.45 |
| Calcium L-(+)-Pyruvate | 1.0 | 0.86 |
| Magnesium L-(+)-Pyruvate | 0.6 | 0.49 |
| | | |
| Glycerol di-lactate mono-palmitate ester | 50.0 | 44.3 |
| Beta hydroxy butyrate | 20.0 | 17.7 |
| Glycerol di-acetate mono-palmitate | 20.0 | 17.7 |
| Maltodextrin | 20.0 | 17.7 |
| TOTAL | 114.6 | |

FIG. 18

| **Example Formula #19** | | |
|---|---|---|
| Solute | Total (g/L) | Total (%) |
| Sodium L-(+)-Lactate | 2.5 | 2.48 |
| Potassium L-(+)-Lactate | 0.1 | 0.07 |
| Calcium L-(+)-Pyruvate | 0.1 | 0.14 |
| Magnesium L-(+)-Pyruvate | 0.1 | 0.08 |
| | | |
| Arginyl Lactate | 52.0 | 52.12 |
| Fructose | 15.0 | 15.04 |
| Glucose | 0.0 | 0.00 |
| Maltodextrin | 30.0 | 30.07 |
| TOTAL | 99.8 | |

FIG. 19

| **Example Formula #20** | | |
|---|---|---|
| Solute | Total (g/L) | Total (%) |
| Glycerol di-lactate, mono-palmitate ester | | 0.1% to 99.9% |
| Sodium lactate | | 0.1% to 99.9% |

FIG. 20

| **Example Formula #21** | | |
|---|---|---|
| Solute | Total (g/L) | Total (%) |
| Sodium L-(+)-Lactate | | 0.0% to 100% |
| Sodium acetoacetate | | 0.0% to 100% |
| Glycerol di-lactate, mono-palmitate ester | | 0.0% to 100% |

FIG. 21

Glycerol

Glycerol-backbone molecule

Lactate

Sodium Lactate

Sodium L-(+)-Lactate

Acetoacetate

Sodium Acetoacetate

Potassium Lactate

Potassium L-(+)-Lactate

Calcium Lactate

Calcium L-(+)-Lactate

Magnesium Lactate

Magnesium L-(+)-Lactate

Pyruvate

Sodium Pyruvate

Arginyl L-(+)-Lactate

Histidine L-(+)-Lactate

Lysine L-(+)-Lactate

Glutamine L-(+)-Lactate

Arginyl - beta hydroxybutyrate

Arginyl – acetoacetate

Arginyl–acetate

Glycerol Tri-L-(+)-Lactate

Glycerol Di-L-(+)-Lactate

Glycerol Mono-L-(+)-Lactate

Glycerol Tri-Palmitate

Mono-L-(+)-Lactate-Di-Palmitate

Glycerol Di-L-(+)-Lactate-Mono-Palmitate

Glycerol Tri-Octanoate

Mono-L(+)-Lactate-Di-Octanoate

Glycerol Di-L-(+)-Lactate-Mono-Octanoate

Glycerol Tri-acetoacetate

Glycerol Di-acetoacetate

Glycerol Mono-acetoacetate

Glycerol Mono-Acetoacetate-Di-L-(+)-Lactate

Glycerol 1,3 Di-Acetoacetate-Mono-L-(+)-Lactate

Glycerol 3 Mono-Acetoacetate-1,2 Di-Palmitate

Glycerol 1,3 Di-Acetoacetate-2 Mono-Palmitate

Glycerol 3 Mono-Acetate-1,2 Di-Lactate

Glycerol 1,2 Di-Acetate 3 Mono-L-(+)-Lactate

Glycerol 2 Mono-Acetate-1,3 Di-Palmitate

Glycerol 1,2 Di-Acetate- 3 Mono-Palmitate

Glycerol Triacetate

BetaHydroxybutyrate (BOHB)

D-Beta-Hydroxybutyrate (BOHB)

Glycerol Tri-D-Beta-Hydroxybutyrate

Glycerol 1,3 Di-D-Beta-Hydroxybutyrate-2 mono acetoacetate

Glycerol 1 Mono-D-Beta-Hydroxybutyrate-2,3 Di Acetoacetate

Glycerol 1,3 Di-D-Beta-Hydroxybutyrate-2 mono-L-(+)-Lactate

Glycerol 1 Mono-D-Beta-Hydroxybutyrate-2,3 Di-L-(+)-Lactate

Arginyl Pyruvate

Histidine Pyruvate

Lysine Pyruvate

Glutamine Pyruvate

Glycerol Tri-Pyruvate

Glycerol 1,3 Di-Pyruvate

Glycerol mono-pyruvate

Glycerol 1 Mono-Pyruvate -2,3 Di-Palmitate

Glycerol 1,3 Di-Pyruvate- 2 Mono-Palmitate

Palmitate

Octanoate

Acetate

Glycerol 1 Mono Beta D Hydroxybutyrate 3 Mono L-(+)-Lactate

Glycerol 1 Mono Beta D Hydroxybutyrate 3 Mono Pyruvate

Glycerol 1 Mono-L-(+)-Lactate 3 Mono Acetoacetate

Glycerol 1 Mono Pyruvate 3 Mono Acetoacetate

Glycerol 1 Mono-L-(+)-Lactate 2 Mono Acetoacetate 3 Mono Beta Hydroxybutyrate

Glycerol 1 Mono Pyruvate 2 Mono Acetoacetate 3 Mono Beta Hydroxybutyrate

Glycerol 1 Mono-L-(+)-Lactate 3 Mono Palmitate

Glycerol 1 Mono Pyruvate 3 Mono Palmitate

Glycerol 1 Mono-L-(+)-Lactate 3 Mono Octanoate

Glycerol 1 Pyruvate 3 Mono Octanoate

Glycerol 1 Mono-L-(+)-Lactate 3 Mono Acetate

Glycerol 1 Pyruvate 3 Mono Acetate

Glycerol 1 beta hydroxybutyrate 3 palmitate

Glycerol 1 acetoacetate 3 palmitate

Glycerol 1 beta hydroxybutyrate 3 octanoate

Glycerol 1 acetoacetate 3 octanoate

Glycerol 1 beta hydroxybutyrate 3 acetate

Glycerol 1 acetoacetate 3 acetate

Glycerol 1 Mono-L-(+)-Lactate, 2 Mono Palmitate 3 Mono beta hydroxybutyrate

Glycerol 1 Pyruvate, 2 Mono Palmitate 3 Mono beta hydroxybutyrate

Glycerol 1 L-(+)-Lactate, 2 Mono Octanoate, 3 Mono beta hydroxybutyrate

Glycerol 1 Pyruvate, 2 Mono Octanoate, 3 Mono beta hydroxybutyrate

Glycerol 1 L-(+)-Lactate, 2 Mono Acetate, 3 Mono beta hydroxybutyrate

Glycerol 1 Pyruvate, 2 Mono Acetate, 3 Mono beta hydroxybutyrate

Glycerol 1 L-(+)-Lactate, 3 Mono Acetoacetate

Glycerol 1 Pyruvate, 3 Mono Acetoacetate

Glycerol 1 L-(+)-Lactate, 2 Mono Palmitate, 3 Mono Acetoacetate

Glycerol 1 Pyruvate, 2 Mono Palmitate, 3 Mono Acetoacetate

Glycerol 1 L-(+)-Lactate, 2 Mono Octanoate, 3 Mono Acetoacetate

Glycerol 1 Pyruvate, 2 Mono Octanoate, 3 Mono Acetoacetate

Glycerol 1, 2 Di-Acetate, 3 Mono-L-(+)-Lactate

Glycerol 2 Mono-Acetate, 1,3 Di-L-(+)-Lactate

Glycerol 1 L-(+)-Lactate, 2 Mono Acetate, 3 Mono Acetoacetate

Glycerol 1 Pyruvate, 2 Mono Acetate, 3 Mono Acetoacetate

L-(+) Lactic acid (R = H or D)

L-(+) CD3 Lactic acid

Sodium L(+) Lactate (R = H or D. Other salts of lactate are also candidates)

Sodium L(+) CD3 Lactate (other salts of lactate are also candidates)

L-arginyl L-(+) CD3 lactate (lactate on Zwitterion);

other amino acids with basic side chains also candidates such as lysine and histidine Glycerol Tri- L- Lactate (R = D or H)

D5 Glycerol Tri- L- Lactate

Glycerol Tri – CD3 – L- Lactate

D5 Glycerol Tri – CD3- L- Lactate

Glycerol Di – CD3 – L- Lactate mono palmitate

L-lysine L-(+) CD3 Lactate

L-histidine L-(+) CD3 Lactate

MOLECULES, FORMULATIONS, AND METHODS FOR NUTRITIONAL SUPPORT OF ATHLETES, PATIENTS, AND OTHERS

APPLICATION PRIORITY DATA

The current patent application is a continuation of Ser. No. 18/096,794 by inventors Brooks, Homing, and San Millán, which claims priority claims priority to U.S. provisional patent application 63/300,563 filed Jan. 18, 2022, by inventors Brooks and Homing.

FIELD OF THE INVENTION

The present disclosure generally relates to the field of nutritional supplementation. Molecules, formulations, and methods for nutritional support of endurance athletes and others are disclosed.

BACKGROUND OF THE INVENTION

The present invention relates to formulations for preparing oral dietary supplements including sports drinks, useful for increasing sports and other physical performances and with beneficial effects on health and wellness.

Traditional sports drinks haven't changed much in formulation since introduction of Gatorade (trademarked name) in 1965. Since then the main ingredients in commercially available sports drinks have been electrolytes and simple sugars such as glucose, fructose, and sucrose. In recent years some companies have added other components such as maltodextrin, branched chain amino acids, and amino acids such as glutamine.

Drawbacks of current sports drink formulations stem from the fact that many who manufacture them lack an appreciation of fundamentals of exercise physiology and metabolism. For example, the drinks contain more or less hexoses that utilize the same set of intestinal solute transporters. Hence, adding more of the same class of solutes only saturates pathways of solute absorption limiting the mass of solute and water transport giving rise to gastrointestinal (GI) distress. In terms of solute transport, current sports drink formulations do not recognize that some classes of intestinal transporters are faster than others for moving solute from GI tract into blood.

As well, sports drinks in the prior art do not contemplate that some transporters are symporters that facilitate solute transport with a cation, typically sodium ion ($Na^+$), and to a lesser extent potassium ion ($K^+$). Co-transport provides the opportunity to move into blood from intestine two efficacious moieties necessary for supporting needs of energy-depleted and dehydrated athletes.

As well, current sports drinks contain either cations Na+ or K+ without regard to the cation levels in blood of healthy individuals that also contains lesser, but important amounts of calcium ($Ca^{++}$), magnesium ($Mg^{++}$), as well as anion counter ions including hydrogen phosphate ($HPO_4^{2-}$) and dihydrogen phosphate ($H_2PO_4^-$), and chloride ($Cl^-$). And finally, perhaps the greatest deficiency of those who manufacture current sports drinks is that they lack understanding of fuel energy substrates that the body, working muscles, heart, liver, kidneys, brain and sweat glands need and that optimal exercise performance requires integrative functioning of those diverse organ systems. Hence, current sports drinks are not optimal for supplying the metabolites needed to rapidly supply energy, electrolytes, and water for optimum performance.

Furthermore, until recently, the recommendations for dietary carbohydrate consumption during endurance activities called for about 30-60 g/h. In this field of endeavor as well in nutrition science in general, carbohydrates are organic compounds containing the atoms carbon (C), hydrogen (H), and oxygen (O) with hydrogen and oxygen in the same ratio as water (2:1).

However, in 2008 and based on substrate utilization analyses with competitive athletes, we realized that in contrast to 60 g/hr, consumption of 80-120 g/h would be more effective. We started using that approach with world-class athletes including athletes at the highest level of professional sports. That novel approach 13 years ago was not free of challenges as it was not easy to meet those carbohydrate requirements of 80-120 g/h. A major obstacle was that it wasn't easy to find sports drinks with high carbohydrate concentration and free of gastrointestinal issues for that high amount of carbohydrate.

The field of health and wellness is one of the largest markets in the world. There is a constant quest to find new products that can improve fitness, health, and well being. However, the majority of the products in the market lack scientific evidence to support claims of efficacy and eventually fade away because the products do not benefit the individual.

SUMMARY OF THE INVENTION

The invention includes, but is not limited to the following, with variations.

The invention includes, in a preferred embodiment, a nutritional formulation for humans and mammals including: a first molecule including gluconeogenic (GNG) precursors or monocarboxylate compounds (MCC). The abbreviation GNG is used herein to mean gluconeogenesis or gluconeogenic, and fractional gluconeogenesis is sometimes referred to as fGNG. The formulation also includes a second molecule type, based on a glycerol backbone, as illustrated in FIG. 23, in a preferred embodiment. FIG. 23 illustrates such a glycerol backbone molecule the glycerol backbone and three groups $B_1$, $B_2$, $B_3$, wherein one or more of the B groups may correspond to one of the functional energy groups $A_1$, $A_2$ or $A_3$, as described below. This second molecule has at least one of the functional groups as illustrated: $B_1$, $B_2$, $B_3$, includes a GNG precursor or MCC and one of the three functional groups is a fatty acid, typically esterified to the glycerol backbone.

The invention also includes preferred embodiments where: at least one of the functional groups: $B_1$, $B_2$, $B_3$, is a ketone or ketone body group; wherein at least one of the functional groups: $B_1$, $B_2$, $B_3$, is chosen from: beta-hydroxybutyrate, acetoacetate; wherein at least two functional groups: $B_1$, $B_2$, $B_3$, each are a GNG precursor or MCC; wherein the GNG precursor or MCC of the second molecule is lactate or pyruvate; wherein the fatty acid of the second molecule is one of: acetate, octanoate, palmitate, oleate or stearate.

The invention formulation in a preferred embodiment includes one or more salts; one or more anaplerotic compounds such as: succinate, glutamate, malate; one or more of: succinate, glutamate, malate. The formulation in is in aqueous form in a preferred embodiment. The aqueous formulation can have the second molecule in at least about 5-8% weight by volume and/or in a concentration of at least about 30 g/L. The aqueous formulation may have at least about 138 mM GNG precursor or MCC.

The aqueous formulation can have one or more of the following cations: $Na^+$, $K^+$, $Ca^{++}$, $Mg^{++}$ and/or one or more of the following anions: $Cl^-$, $HPO_4^{2-}$, $H_2PO_4^-$. The aqueous formulation of can be electrically neutral. The formulation can be suitable for one or more of: oral, enteral, or parenteral use. The aqueous formulation can have a molarity of about 300-1000 mM. The second molecule of the formulation can include two lactate groups, two pyruvate groups, or one lactate group and one pyruvate group, or one lactate group and two fatty acid groups.

The invention includes, in a preferred embodiment, a nutritional formulation for humans and mammals including: a first molecule including a GNG precursor or MCC, a second molecule including a second GNG precursor or MCC; and a third molecule including a fatty acid group. The invention includes a nutritional formulation wherein the second molecule or third molecule further includes a ketone or ketone body group; wherein the second molecule or third molecule further includes beta-hydroxybutyrate or acetoacetate; wherein the second molecule or third molecule further is a third GNG precursor or MCC; wherein the GNG precursor or MCC of the second molecule is lactate or pyruvate. The fatty acid of the third molecule includes one of: acetate, octanoate, palmitate, oleate or stearate.

The invention formulation in a preferred embodiment includes one or more salts; one or more anaplerotic compounds such as: succinate, glutamate, malate. The formulation is in aqueous form in a preferred embodiment. The aqueous formulation can have the second molecule at least about 5% weight by volume and/or in a concentration of at least about 30 g/L. The aqueous formulation can be where the components besides water are at least of about 5-8% weight by volume. The aqueous formulation can have one or more of the following cations: $Na^+$, $K^+$, $Ca^{++}$, $Mg^+$+ and/or one or more of the following anions: $Cl^-$, $HPO_4^{2-}$, $H_2PO_4^-$. The aqueous formulation can be electrically neutral. The formulation can be suitable for one or more of: oral, enteral, or parenteral use. The aqueous formulation can have a molarity of about 300-1000 mM. The second molecule of the formulation can include two lactate groups, two pyruvate groups, or one lactate group and one pyruvate group, or one lactate group and two fatty acid groups. The second molecule and third molecule can be the same or different molecules in preferred embodiments. The second molecule/third molecule may be a glycerol backbone molecule.

Many of the molecules disclosed are inventive in and of themselves. In a preferred embodiment a molecule type based on a glycerol backbone, as illustrated in FIG. 23. FIG. 23 illustrates such a glycerol backbone molecule the glycerol backbone and three groups $B_1$, $B_2$, $B_3$, wherein one or more of the B groups may correspond to one of the functional energy groups $A_1$, $A_2$ or $A_3$, as described below. It has at least one of the functional groups as illustrated: $B_1$, $B_2$, $B_3$, in preferred embodiments, wherein at least one of the three functional groups $B_1$, $B_2$, $B_3$, includes a fatty acid; wherein at least one of the functional groups $B_1$, $B_2$, $B_3$, is chosen from: beta-hydroxybutyrate, acetoacetate; wherein the molecule has an additional GNG precursor or MCC; wherein the GNG precursor or MCC includes lactate or pyruvate; wherein the molecule includes acetate, octanoate, palmitate, oleate or stearate functional group.

A molecule may also include a GNG precursor or MCC and a ketone or ketone body group, a fatty acid group, beta-hydroxybutyrate or acetoacetate, an additional GNG precursor or MCC, including lactate or pyruvate.

The molecule may be part of a formulation with additional components, the formulation may be an aqueous formulation. The aqueous formulation may have at least about 138 mM GNG precursor or MCC. The aqueous formulation may have at least about 30 g/L GNG precursor or MCC. The aqueous formulation may have one or more of the following cations: $Na^+$, $K^+$, $Ca^{++}$, $Mg^{++}$. The aqueous formulation may have one or more of the following anions: $Cl^-$, $HPO_4^{2-}$, $H_2PO_4^-$. The aqueous formulation may be electrically neutral. The formulation may be suitable for one or more of: oral, enteral, or parenteral use. The aqueous formulation may have a molarity of about 300-1000 mM.

The molecules of the inventions may be the basis for inventive formulations, as discussed above, and as now further described, and below. The molecules may be in a formulation such as aqueous formulation. A molecule in the aqueous formulation may be least about 5-8% weight by volume, and/or a concentration of at least about 30 g/L. The aqueous formulation may also have of the following cations: $Na^+$, $K^+$, $Ca^{++}$, $Mg^{++}{}_+$ the following anions: $Cl^-$, $HPO_4^{2-}$, $H_2PO_4^-$. The aqueous formulation may be electrically neutral and be suitable for one or more of: oral, enteral, or parenteral use. The aqueous formulation may have a molarity of about 300-1000 mM. The molecule may be suitable for nutritional support of humans or other mammals.

The invention also includes methods for administering, providing, and providing instructions for use of the disclosed molecules and formulations. The method of the invention provides nutritional support to a human under exercise, injury, illness, or other metabolic stress. The invention provides methods utilizing an aqueous formulation for oral, enteral, or parenteral consumption, the formulation having a molecule type as FIG. 23 illustrates, a glycerol backbone molecule. FIG. 23 illustrates such a glycerol backbone molecule the glycerol backbone and three groups $B_1$, $B_2$, $B_3$, wherein one or more of the B groups may correspond to one of the functional energy groups $A_1$, $A_2$ or $A_3$, as described.

The glycerol backbone and three groups $B_1$, $B_2$, $B_3$, can be such that one or more of the B groups may correspond to one of the functional energy groups molecule wherein at least one of the functional groups $B_1$, $B_2$, $B_3$, of the molecule is a GNG precursor or MCC and at least one of the three functional groups $B_1$, $B_2$, $B_3$, is a ketone or ketone body group; wherein at least one of the three functional groups $B_1$, $B_2$, $B_3$, of the molecule comprises a fatty acid; wherein the formulation comprises an additional GNG precursor or MCC.

The invention method contemplates wherein the formulation is provided so that consumption of the formulation is at a rate of at least about 80 g of non-water ingredients per dose, wherein consumption of the formulation is at a rate of no more than about 120 g of non-water ingredients per dose.

The invention method provides nutritional support to a human under exercise, injury, illness, or other metabolic stress, the method comprising: providing an aqueous formulation for oral, enteral, or parenteral consumption, the formulation may include: a first molecule comprising a GNG precursor or MCC; and a second molecule type as FIG. 23 illustrates, a glycerol backbone molecule. FIG. 23 illustrates such a glycerol backbone molecule the glycerol backbone and three groups $B_1$, $B_2$, $B_3$, wherein one or more of the B groups may correspond to one of the functional energy groups $A_1$, $A_2$ or $A_3$, as described. The glycerol backbone and three groups $B_1$, $B_2$, $B_3$ may be where at least one of the functional groups $B_1$, $B_2$, $B_3$, of the second molecule is a GNG precursor or MCC and at least one of the three functional groups $B_1$, $B_2$, $B_3$, is a fatty acid; wherein at least one of the three functional groups $B_1$, $B_2$, $B_3$, of the molecule is a ketone or ketone body group.

The formulation may have an additional GNG precursor or MCC. The formulation may be provided so that consumption of the formulation is at a rate of at least about 80 g of non-water ingredients per hour and wherein it is provided so that consumption of the formulation is at a rate of no more than about 120 g of non-water ingredients per dose. The invention includes a method of providing nutritional support to a human under exercise, injury, illness, or other metabolic stress, the method including providing human readable instructions on consuming an aqueous formulation as described above. The instructions may be provided by a computer graphical user interface and may be specific for diabetic or pre-diabetic patients.

The methods of providing nutritional support to a human under exercise, injury, illness, or other metabolic stress may include providing human readable instructions on consuming an aqueous formulation for oral, enteral, or parenteral consumption, the formulation including: a first molecule with a GNG precursor or MCC; and a second molecule type as FIG. 23 illustrates, a glycerol backbone molecule. FIG. 23 illustrates such a glycerol backbone molecule the glycerol backbone and three groups $B_1$, $B_2$, $B_3$, wherein one or more of the B groups may correspond to one of the functional energy groups $A_1$, $A_2$ or $A_3$, as described. The glycerol backbone and three groups $B_1$, $B_2$, $B_3$ may be at where one of the functional groups $B_1$, $B_2$, $B_3$, of the second molecule is a GNG precursor or MCC and at least one of the three functional groups $B_1$, $B_2$, $B_3$, is a fatty acid; wherein at least one of the three functional groups $B_1$, $B_2$, $B_3$, of the molecule is a ketone or ketone body group.

Also the molecule type may be wherein at least one of the functional groups $B_1$, $B_2$, $B_3$, of the second molecule comprises a GNG precursor or MCC and at least one of the three functional groups $B_1$, $B_2$, $B_3$, comprises a fatty acid, wherein at least one of the three functional groups $B_1$, $B_2$, $B_3$, of the molecule comprises a ketone or ketone body group; wherein the formulation comprises an additional GNG precursor or MCC. The formulation may be provided so that consumption of the formulation is at a rate of at least about 80 g of non-water ingredients per hour. The method wherein the formulation is provided so that consumption of the formulation is at a rate of no more than about 120 g of non-water ingredients per dose. Instructions may be provided by a computer graphical user interface and may be specific for diabetic or pre-diabetic patients.

The invention also includes methods of addressing the nutritional status of a human or other mammal, the method including: (a) measuring a blood glucose concentration, (b) measuring a blood lactate concentration, (c) measuring a blood ketone and ketone body concentration; and based on (a), (b), and (c), if (a) is less than about 5 mM and (b) is less than about 2 mM and (c) is less than about 0.2 mM, starting or increasing a nutritional support. The method may be used wherein the human or mammal is exercising, injured, ill or under other metabolic stress. This method contemplates molecules and formulations as disclosed throughout.

The invention also includes methods of addressing the nutritional status of a human or other mammal, the method including: (a) measuring a blood glucose concentration, (b) measuring a blood lactate concentration, (c) measuring a blood ketone and ketone body concentration; and based on (a), (b), and (c), if (a) is more than about 7 mM and (b) is less than about 4 mM and (c) is less than about 3 mM, ceasing or decreasing a nutritional support. The method may be used wherein the human or mammal is exercising, injured, ill or under other metabolic stress. This method contemplates molecules and formulations as disclosed throughout.

Additional formulations of the invention include a formulation including: an inorganic salt of a GNG precursor or MCC, a compound with a GNG precursor or MCC, and inorganic anions sufficient to achieve electrical neutrality. The compound may be an inorganic salt of a monocarboxylic compound, an organic group, an amino acid such as one of the following: arginine, histidine, lysine.

The compound may have a glycerol backbone as illustrated in FIG. 23. FIG. 23 illustrates such a glycerol backbone molecule the glycerol backbone and three groups $B_1$, $B_2$, $B_3$, wherein one or more of the B groups may correspond to one of the functional energy groups $A_1$, $A_2$ or $A_3$, as described. The compound may have lactate or pyruvate or acetate esterified to glycerol. The compound may have lactate or pyruvate and a free fatty acid esterified to glycerol. The compound may have a short, medium, or long chain fatty acid esterified to glycerol. The compound of may have lactate or pyruvate and beta hydroxy butyrate esterified to glycerol, may have lactate or pyruvate and acetoacetate esterified to glycerol, may have a biologically active ketone, ketoacid, or both esterified to glycerol. One or both of the GNG precursors or MCCs is acetate or an acetoacetate.

The formulation may be a nutritional formulation for humans or other mammals, may be suitable for oral, enteral, or parenteral use. The formulation may have one or more of the cations $Na^+$, $K^+$, $Ca^{++}$, $Mg^{++}$. The formulation further comprises one or more of the anions $HPO_4^{2-}$ or $H_2PO_4^-$. The formulation may be electrically neutral.

The invention also contemplates computer instructions and computer programs for executing the above methods, such as automated methods or administering as well as the providing instructions or guidance to humans to execute such methods. Deuteration of the molecules and formulations of the invention is contemplated to chemical behavior, such as reaction kinetics and uptake.

BRIEF DESCRIPTION OF THE DRAWINGS

The described techniques and mechanisms, together with other features, embodiments, and advantages of the present disclosure, may best be understood by reference to the following description taken in conjunction with the accompanying drawings, which illustrate various embodiments of the present techniques and mechanisms. In the drawings, structural elements having the same or similar functions are denoted by like reference numerals.

FIGS. 1-21 are tables that show preferred formulations of the invention, with approximate component concentrations (amounts), although different concentrations are contemplated and discussed throughout, as well as claimed.

FIG. 22 is glycerol, a compound with nutritional value that is used as a basis for a class of molecules of the invention. FIGS. 24-125 generally show variations on the molecule class of FIG. 23 that are some, but not all, preferred embodiments of the invention.

DETAILED DESCRIPTION OF THE INVENTION

Figure 22:
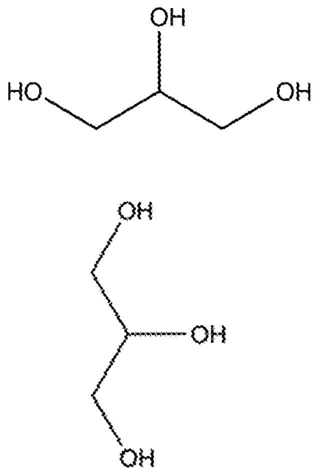
FIGS. 22-125 illustrate various preferred molecules of the invention, though related molecules are contemplated.

In the past, research supported carbohydrate supplementation rates of 1 gram/minute, or 60 g/hr. However, recently, it has been finally realized that higher energy substrate ingestion for endurance sports performance is possible, and some recommendations now call for 90 g/h. However, at present recommendations for using simple sugars and starches present challenges because they have limited absorption capacity and result in bloating and upset GI. Previous recommendation believed that 30 to 60 g/h would be the maximum to ingest to increase performance. However, with the formulations of this invention utilizing unique molecules using multiple carriers (R) and fuel energy sources (A) it is possible to significantly increase the ingestion of energy substrates to about 120 g per dose and achieve as much as 160 g/h of carbohydrate energy. With the formulations of the invention it is possible to significantly increase the ingestion of energy substrates to about 120 g in one single dose allowing a carbohydrate ingestion up to about 160 g/h. We have successfully used this protocol in the 2020 season during competition at the highest level of professional sports. Hence, we have created a new paradigm in oral dietary supplementation for endurance exercise competition. This is an amount that even science reports to be impossible to assimilate through traditional sports drinks based on glucose, fructose, maltodextrin, or sucrose.

The inventions disclosed are based on the inventors many decades of experience in this field, including one of the inventors, Brooks, being of inventor of the scientific concept known as the Lactate Shuttle Theory (or Hypothesis), which shows that by adding lactate, pyruvate and other compounds unique to the invention that it is possible to increase significantly the ingestion and uptake of carbohydrate as described (Brooks 1985, Brooks 1986, Brooks 2002, Brooks 2019).

The present invention relates to novel formulations to maximize short-, medium- and long-term fuel delivery and endurance exercise for the application of sports and other nutrition in healthy, ill, and injured humans and other mammals undergoing physical and other stresses such as extreme exercise and dehydration. By "other mammals," species such as race horses and camels in particular are intended. Supporting this invention there are fifty years of intense research in the field of exercise physiology, metabolism and nutrition with over three hundred peer-reviewed scientific publications plus practical experience coaching professional teams to world class victories. The above problems and drawbacks are optimized by the below invention.

In this field of endeavor as well as in nutrition science in general, carbohydrates are organic compounds containing the atoms carbon (C), hydrogen (H), and oxygen (O) with hydrogen and oxygen in the same ratio as water (2:1). In terms of human and mammalian nutrition, carbohydrates are foods such as sugars and starches. Historically, the term carbohydrate is abbreviated as CHO. In contrast, while foods and metabolites such as fatty acids and ketones are made generally of just of C, H and O atoms, the 2H, 1 O definition does not fit, and hence fats and ketones are not generally classified as carbohydrates. Amino acids are unique in that they are made of C, H, O and N atoms. In biology, processes of deamination (removing N) and transamination (switching the N to another molecule) allows for many amino acids to become carbohydrate metabolites. The conversion of CHO metabolites and amino acids to the essential blood metabolite glucose is termed gluconeogenesis (GNG), and amino acids readily converted to glucose are termed glucogenic. Also in biology, nutrition, and metabolism the important molecule glycerol (glycerin) does not readily fit into the definitions of carbohydrate or fat and is sometimes referred to as a sugar alcohol. However, glycerol is an important backbone molecule for triglyceride (body fat) storage as well as a GNG precursor.

Lactate, pyruvate, and similar nutritional molecules are herein referred to as monocarboxylate compounds (MCC). The metabolic precursors of glucose in the gluconeogenic (GNG) pathway are herein called GNG precursors. The abbreviation GNG is used herein to mean gluconeogenesis or gluconeogenic, and fractional gluconeogenesis is sometimes referred to as fGNG. GNG precursors include many MCCs, such as those listed herein, as well as other compounds, such as some amino acids (e.g., alanine) and glycerol compounds.

Functional Groups Simultaneously Providing Energy for Different Metabolic Pathways The invention includes novel and useful molecular compounds for delivery of energy substrate, and in particular delivers functional groups that can be utilized by more than one metabolic pathway. The invention also includes formulations that include and utilize these molecules, especially oral dietary supplement formulations as disclosed. Other embodiments include parenteral and enteral use. What is new and novel in the application is that up to three sets of cation carriers (negatively charged R-groups) are used to deliver multiple forms of anion energy substrate nutrients (positively charged A-groups), with both carriers and nutrients having biological viability. "Biological availability" refers to the ability of an energy substrate to be digested, absorbed, circulated, taken up and used by various tissues including working muscles, the beating heart, the liver in supporting blood glucose homeostasis via gluconeogenesis, and high-level executive function while providing an energy substrate for the brain. As well, these molecules can be delivered in conjunction with carbohydrate energy in forms typically identified as sugars and starches. There are no other drinks like those of the invention in the market making them the next generation of sports drinks, and because of the efficacy of the ingredients that make up the formulations, the benefits to health and wellness of the individual extend beyond sports performance including diabetes care.

A preferred embodiment of the invention has a formulation with at least two molecules wherein at least one of the molecules of the formulation has an R carrier group (herein labelled "R") and an A energy group (herein labelled "A") plus a second molecule that is a MCC or GNG precursor molecule. The second molecule also can follow the RA convention. More than one energy functional group A can be carried by a single R carrier group and up to three energy functional groups A can provide energy on a single molecule of a preferred embodiment of formulation such as when the R carrier group is glycerol. Typically the more than one A energy functional groups carried by a single R group will have more than one metabolic pathway as provided by a single molecule of the formulation.

In another preferred embodiment of the invention at least two molecules of the formulation have an R carrier group and an A energy group. Each of the Rs as shown can be different molecule carriers (e.g., $R_1$, $R_2$, $R_3$) or even the same molecule carrier. For instance, in a preferred embodiment, one of the Rs is the glycerol backbone molecule from the carrier group $R_2$, with each of the three As esterified to one carbon of the glycerol selected from the A energy group $A_1$, $A_2$, or $A_3$. Or, with such a glycerol backbone molecule, in some embodiments only one or two of the A energy functional groups is esterified to the glycerol, and the other energy functional groups are carried by other R carriers.

Anion Energy Substrate Groups A ($A_1$, $A_2$, $A_3$)

In the formulations of the invention the said anion energy substrate groups are MCC or GNG precursor anion $A_1$, ketone anion $A_2$ and fatty acid anion $A_3$, in which:

- the MCC or GNG precursor anion $A_1$ is lactate, pyruvate, their derivatives and mixtures of them as given in FIGS. 1-21 with approximate concentrations/amounts. FIGS. 1-21 show approximately isotonic aqueous formulations (Iso) with example approximate component concentrations (amounts), though different concentrations are contemplated. In preferred embodiments, the total concentrations are about 300 milliequivalents per Liter (mEq/Liter)] for oral or intravenous administration, though other formulations are shown and contemplated. Note that in the figures, the discussed carriers $R_1$ $R_2$ $R_a$ and $A_1$ $A_2$ A3 might not be subscripted, in other words, for example, R1 is the same as $R_1$.
- The ketone anion $A_2$ can be acetoacetate, beta-hydroxybutyrate, their derivatives and mixtures of them for isotonic solutions that are also provided in FIGS. 1-21. As stated immediately above, solutions of greater concentration s 1,000 mEq/L and >1,000 mEq/L depending on the route of administration and choice of beverage (aqueous solution gel, or other delivery format);
- the fatty acid anion $A_3$ can be short chain (e.g., acetate), medium chain (e.g., octanoate), or long chain (e.g., palmitate, oleate), their derivatives and mixtures of them. Solute concentrations can be of three levels: Isotonic and two hypertonic levels (s 1,000 mEq/L, and >1,000 mEq/L) mixtures of ingredients as listed in FIGS. 1-21.

In a preferred embodiment of the invention, the fatty acid anions $A_3$ are short-, medium-, long-chain, and very long chain fatty acids, having between 1 and 26 carbon atoms with a carboxyl group, their derivatives and mixtures of them. Boundaries of tonicity stated above and illustrated in FIGS. 1-21 for beverages and gels (≈300 to >1,000 mEq/L).

In the formulations of the invention the said anion energy substrate groups are MCC and GNG precursor anion $A_1$, ketone anion $A_2$ and fatty acid anion $A_3$, in which concentrated solutions of ≤1,000 mEq/L are suitable for oral or intravenous administration. Concentrated solutions of >1,000 mEq/L can be administered orally. In addition to serving as a template for $A_1$ administration, FIGS. 1-21 also provides desirable ranges of $A_2$ and $A_3$ energy substrates.

Cation Carrier Groups R ($R_1$, $R_2$, $R_3$)

In the formulations of the invention the said carrier molecule consists of cations of inorganic salts, esters and amino acids. In particular:

- the cations of inorganic salts $R_1$ are Sodium ($Na^+$), Potassium ($K^+$), Magnesium ($Mg^{++}$) and Calcium ($Ca^{++}$) in ratios as they exist in human blood;
- the esters, $R_2$ are mono-, di- and tri-esters of glycerol or glycerol esters, thiolesters of amino acids and their derivatives; and
- the amino acids, $R_3$ are arginine, lysine, cysteine, histidine and their derivatives that carry positive charges at alkaline pH, but in an acid environment such as the stomach, ready dissociate freeing both R and A groups for absorption.

According to a preferred embodiment of the formulations of the invention the amino acids are unique amino acids that can form thiolesters with organic anions, for example cysteine, methionine and their derivatives.

As stated, carriers R can be viable energy substrates in and of themselves that are attached to said other biologically viable energy substrates A. Carriers R and energy substrates A are readily transported from the intestine into the systemic blood circulation by independent transport mechanisms and subsequently moved around the body via the systemic circulation.

R Carriers Including Glycerol Backbone

Figure 23:
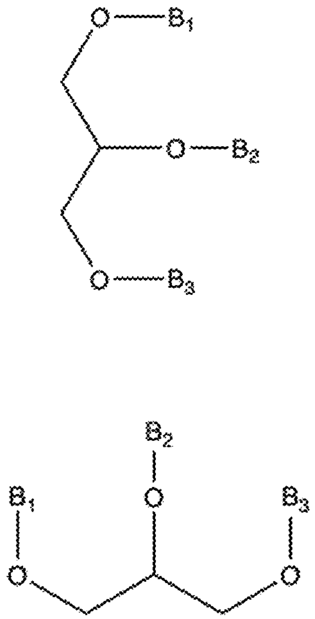
FIG. 23 illustrates a glycerol-backbone molecule, with functional groups $B_1$, $B_2$, $B_3$, as described, used as a basis for a class of molecules of the invention.
Figure 24:
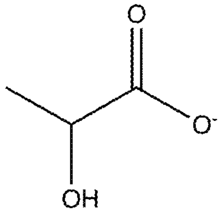
Figure 25:
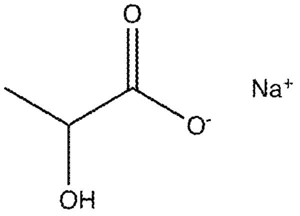
Figure 26:
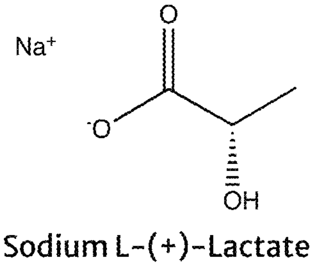
Figure 27:
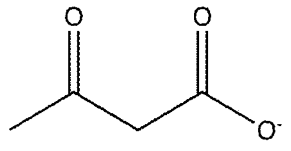
Figure 28:
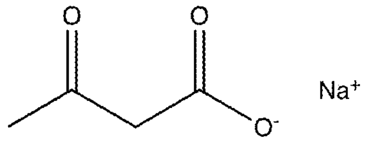
Figure 29:
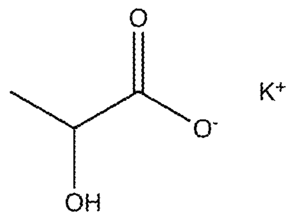
Figure 29:
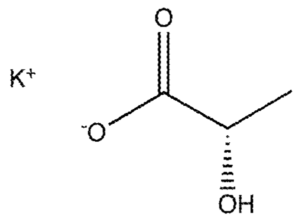
Figure 30:
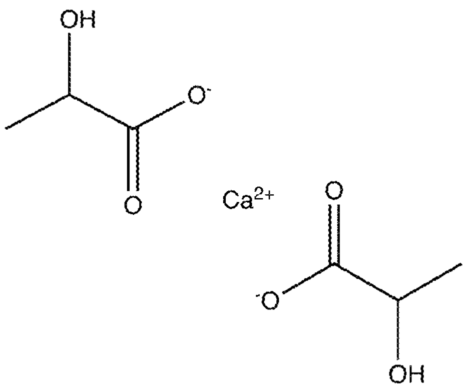
Figure 30:
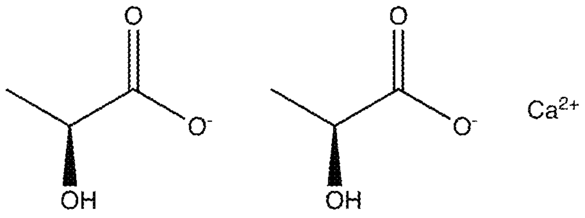
Figure 31:
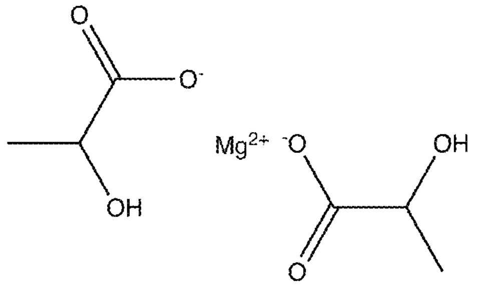
Figure 31:
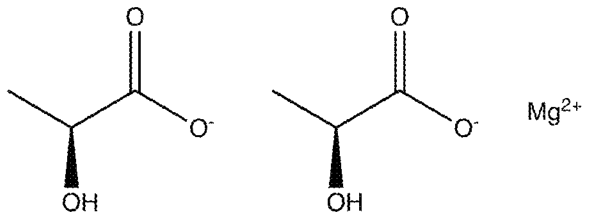
Figure 32:
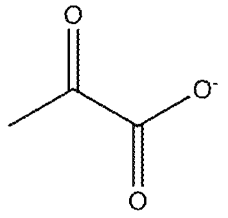
Figure 32:
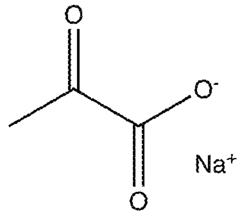
Figure 33:
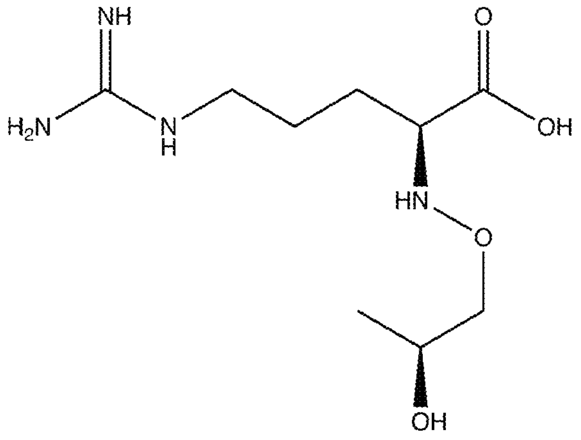
Figure 34:
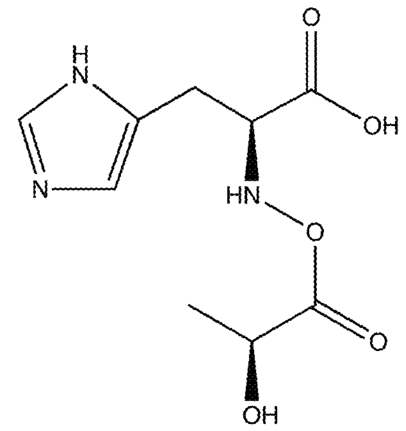
Figure 35:
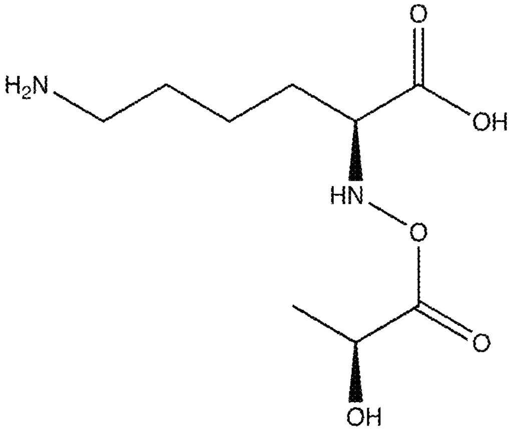
Figure 36:
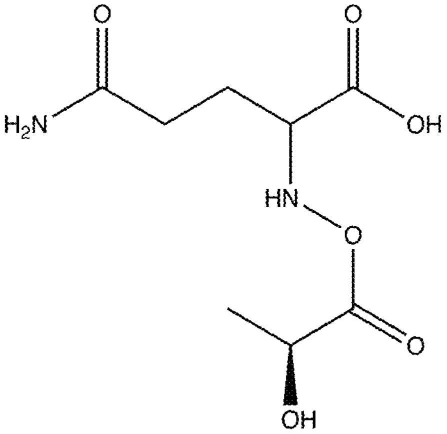
Figure 37:
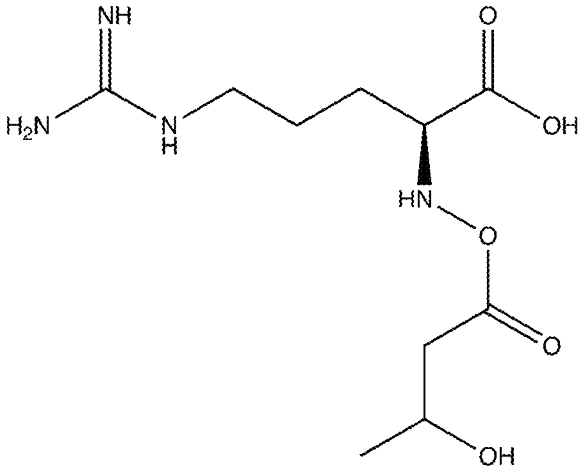
Figure 38:
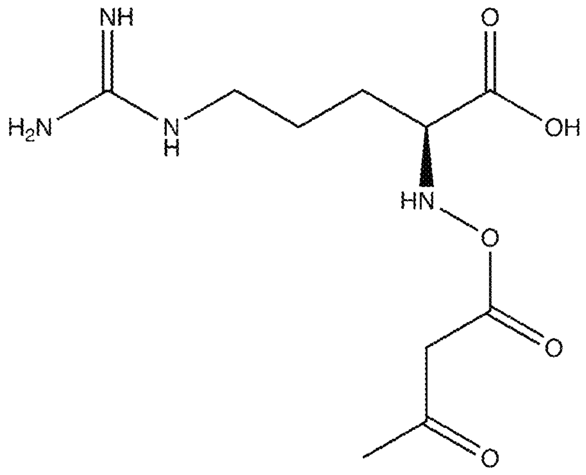
Figure 39:
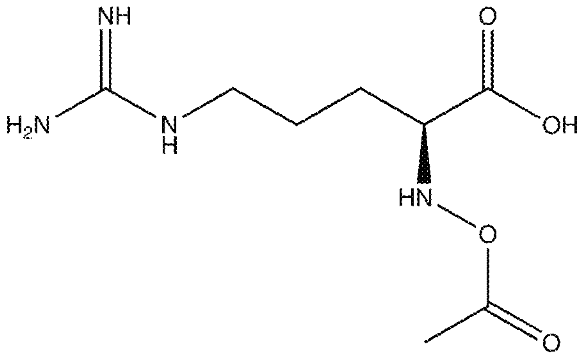
Figure 40:
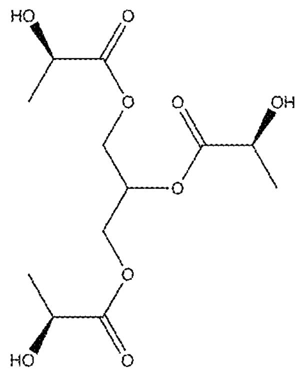
Figure 41:
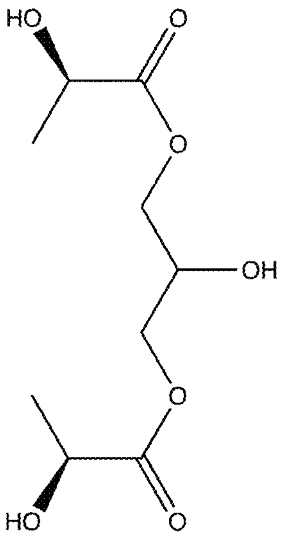
Figure 42:
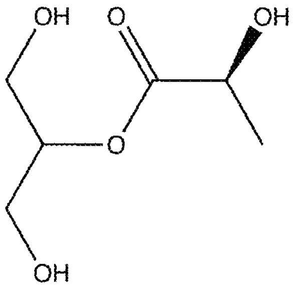
Figure 43:
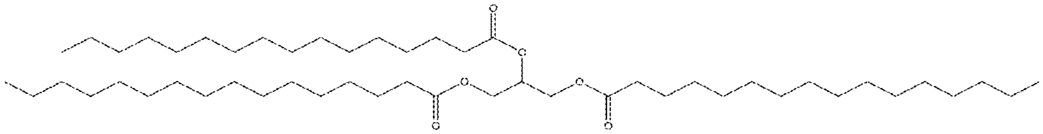
Figure 44:
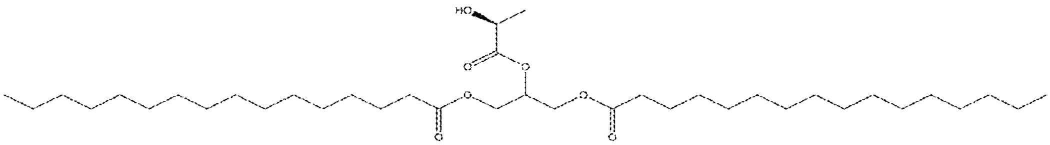
Figure 45:
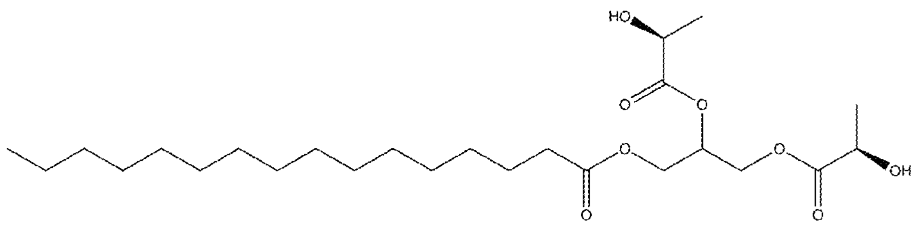
Figure 46:
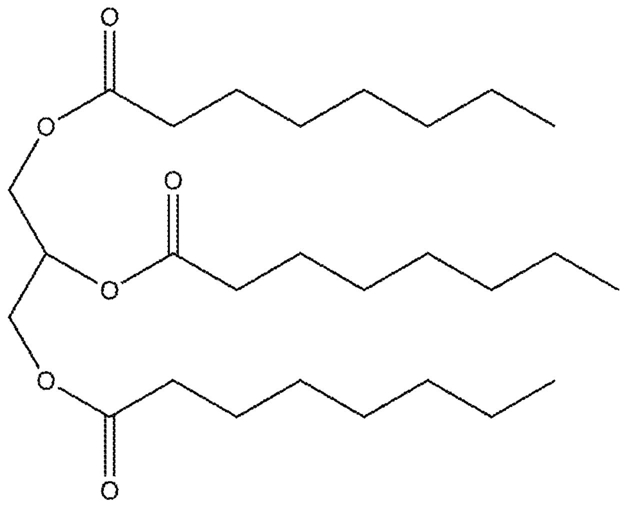
Figure 47:
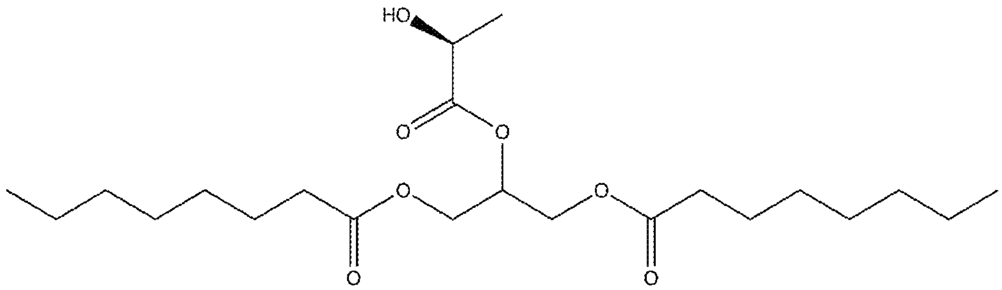
Figure 48:
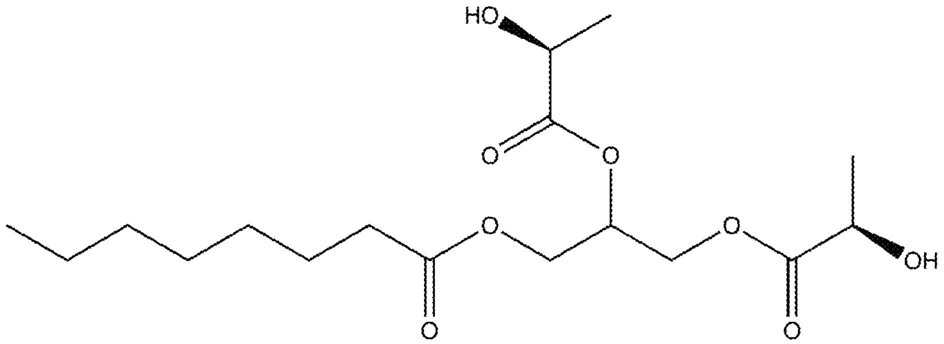
Figure 49:
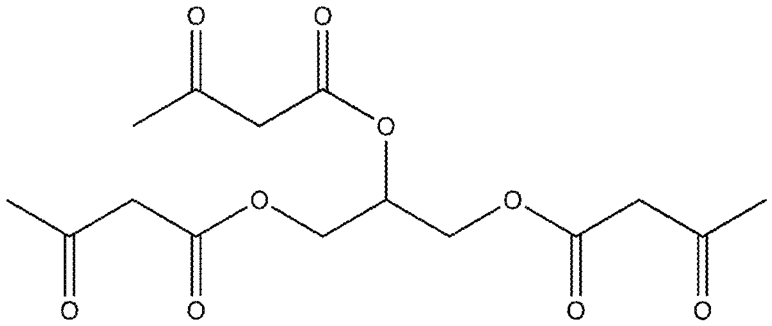
Figure 50:
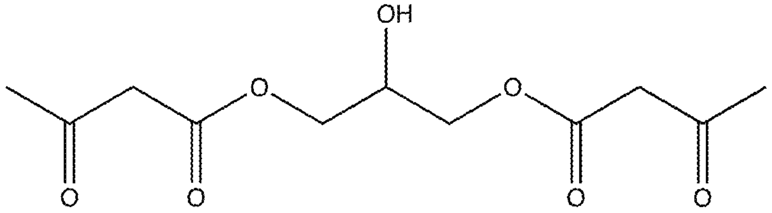
Figure 51:
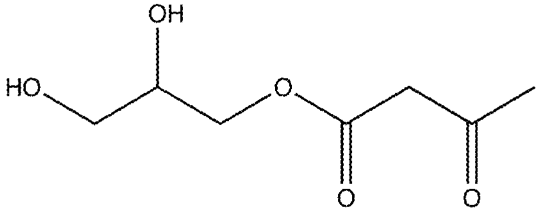
Figure 52:
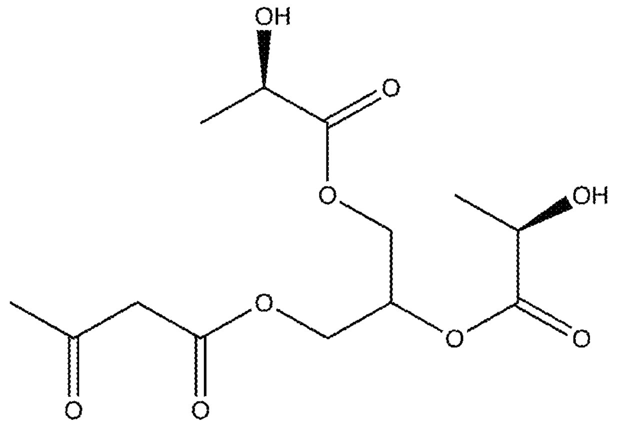
Figure 53:
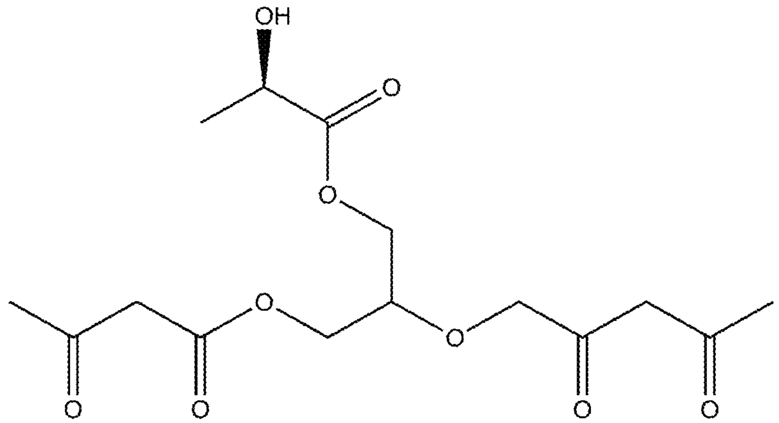
Figure 54:
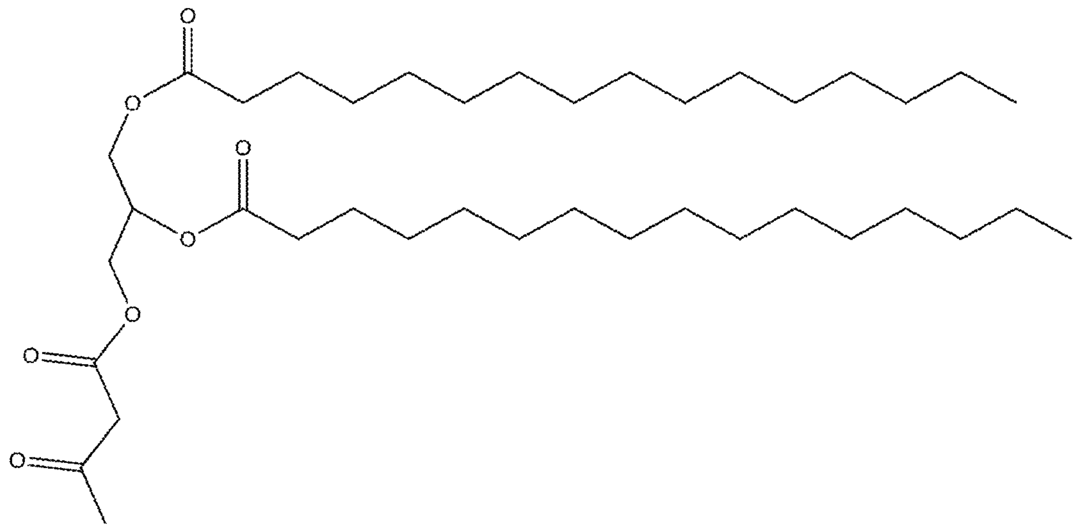
Figure 55:
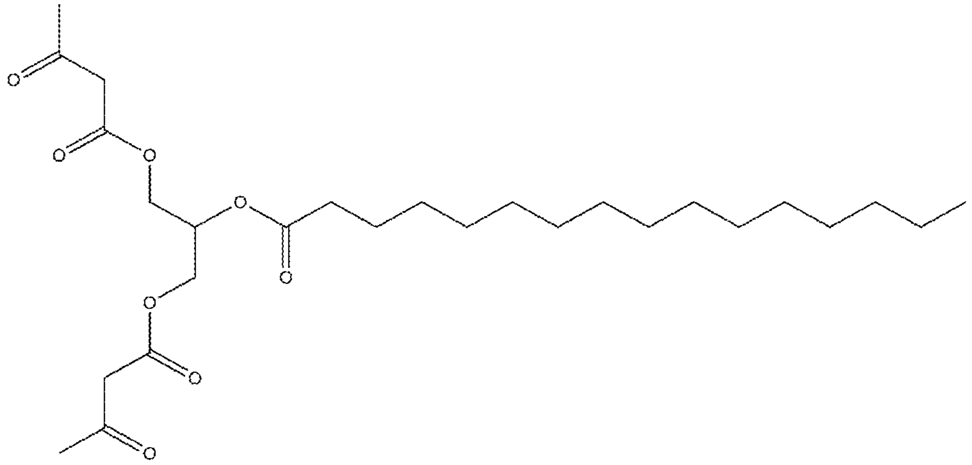
Figure 56:
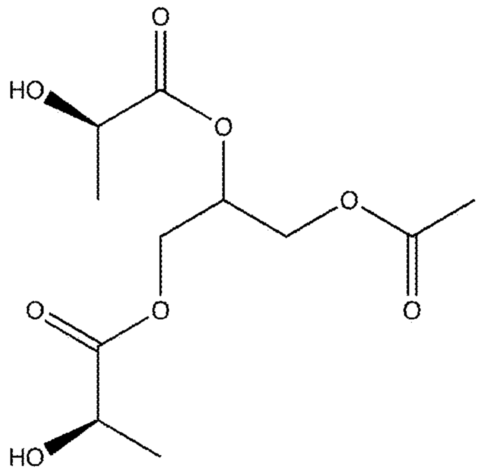
Figure 57:
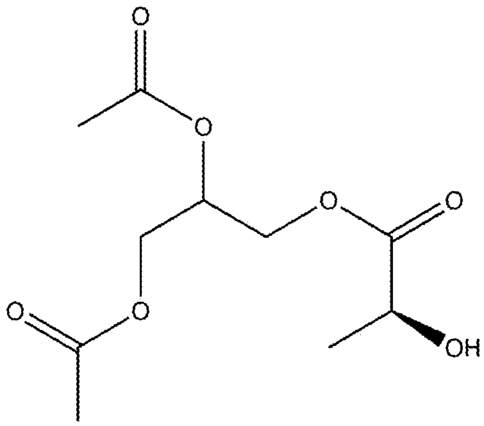
Figure 58:
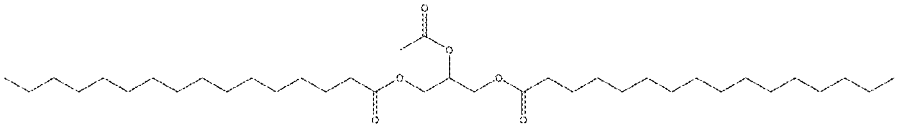
Figure 59:
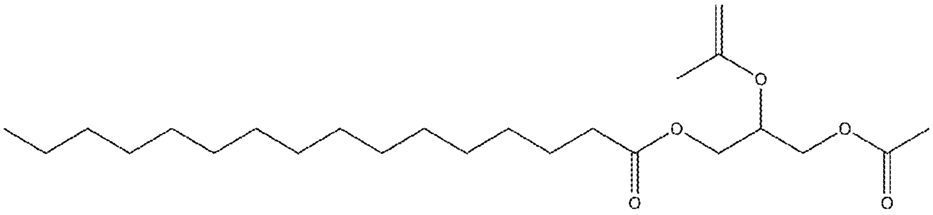
Figure 60:
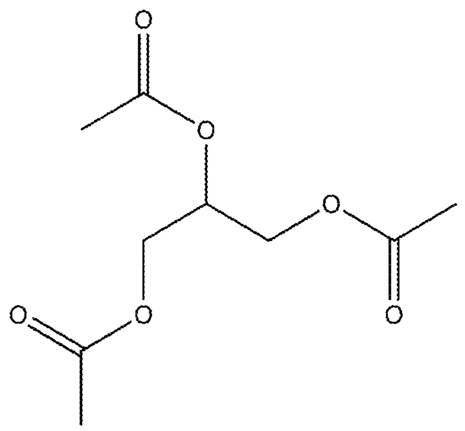
Figure 61:
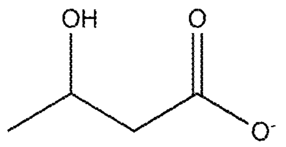
Figure 62:
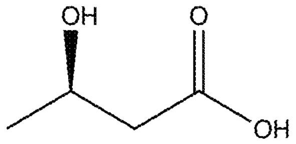
Figure 63:
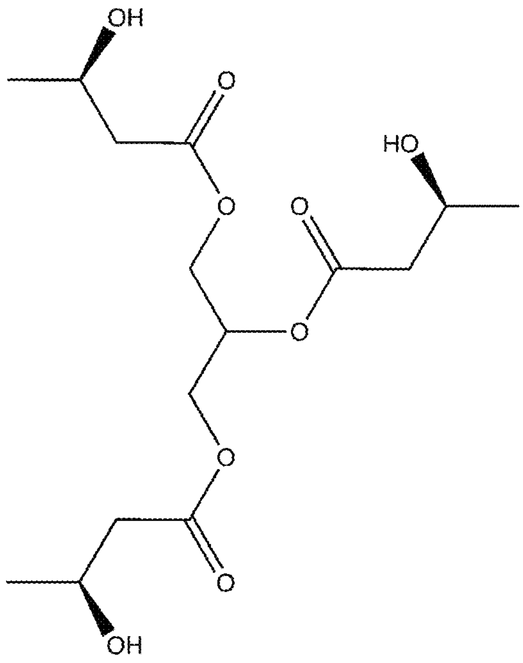
Figure 64:
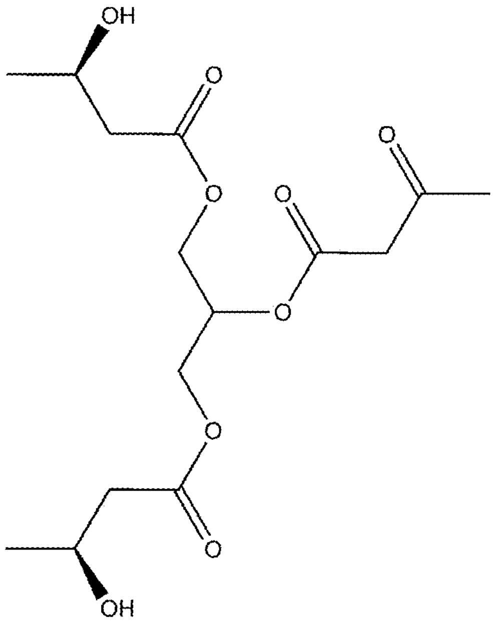
Figure 65:
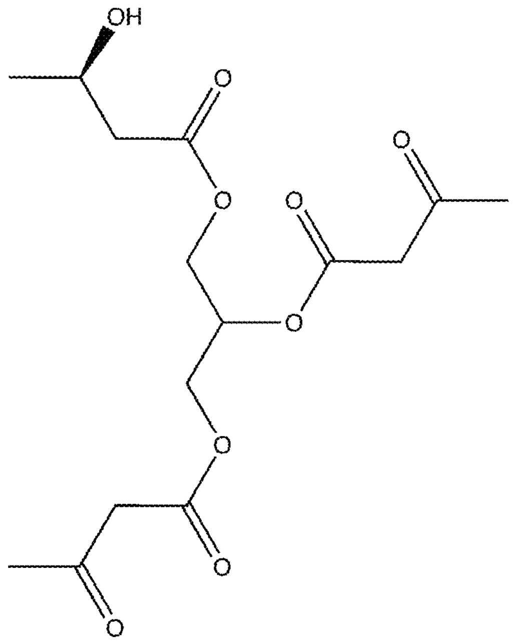
Figure 66:
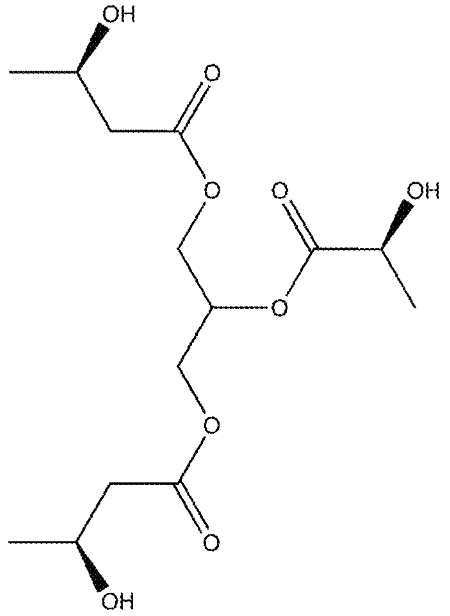
Figure 67:
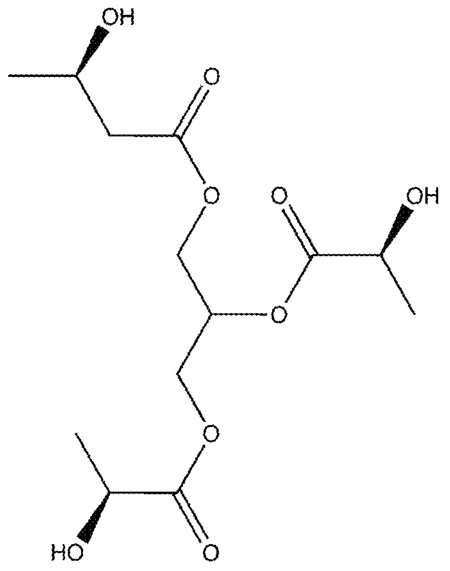
Figure 68:
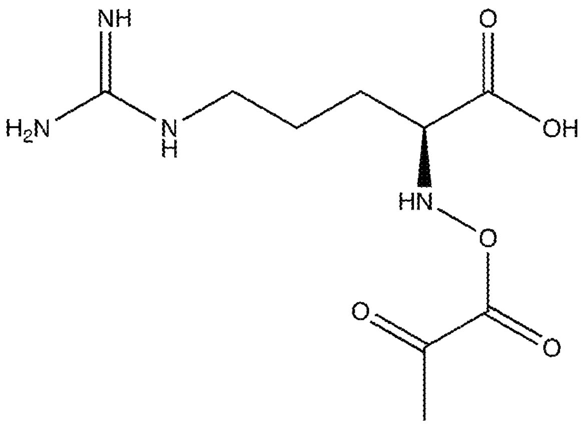
Figure 69:
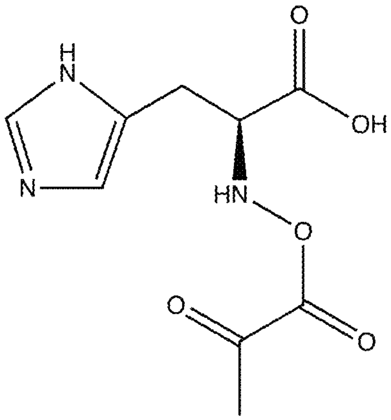
Figure 70:
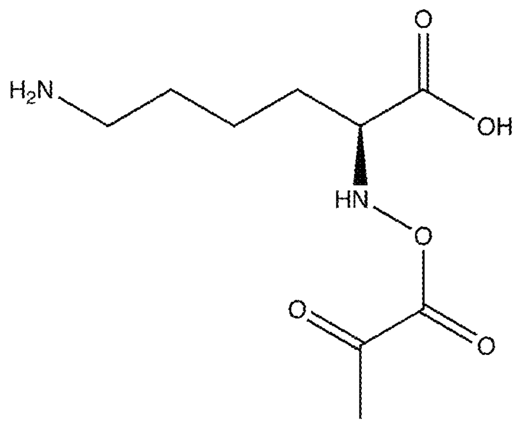
Figure 71:
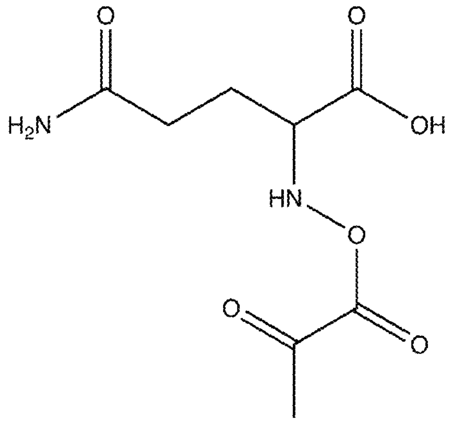
Figure 72:
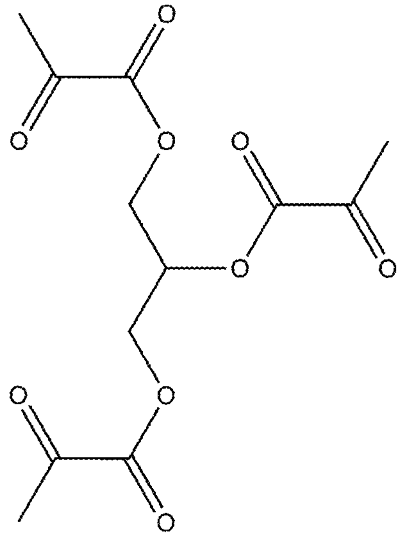
Figure 73:
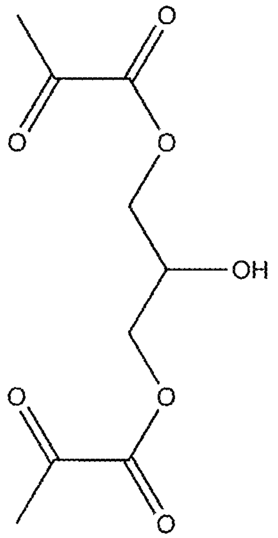
Figure 74:
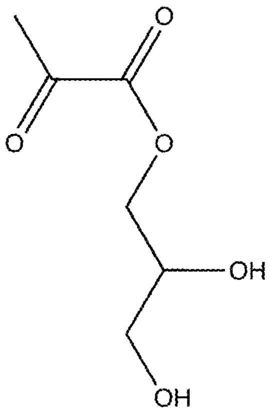
Figure 75:
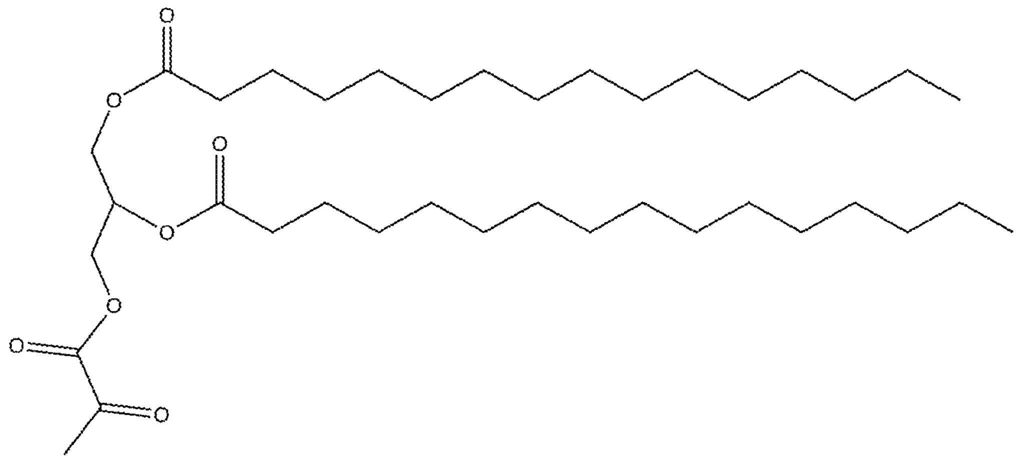
Figure 76:
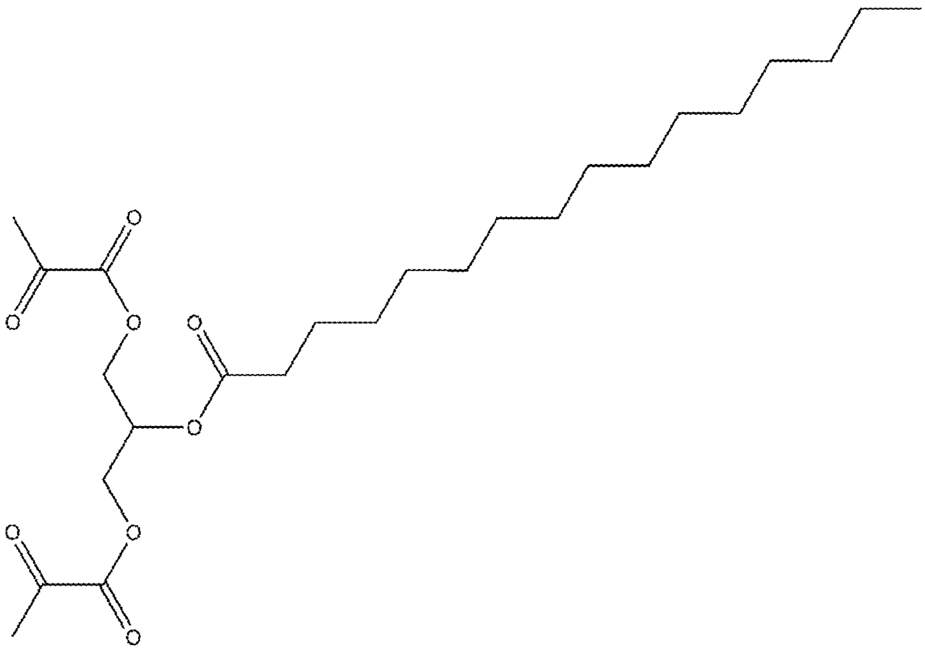
Figure 77:
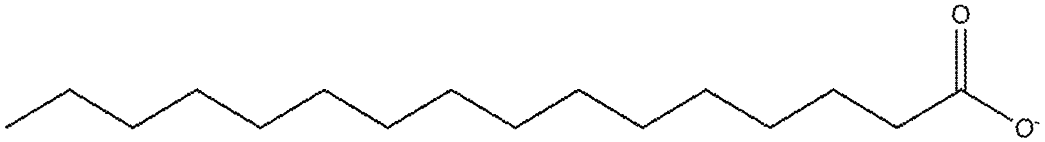
Figure 78:
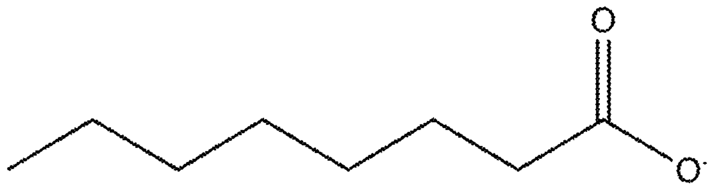
Figure 79:
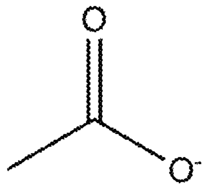
Figure 80:
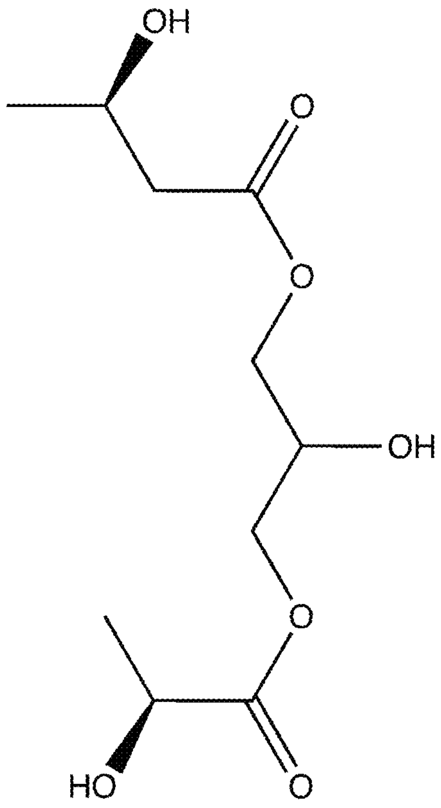
Figure 81:
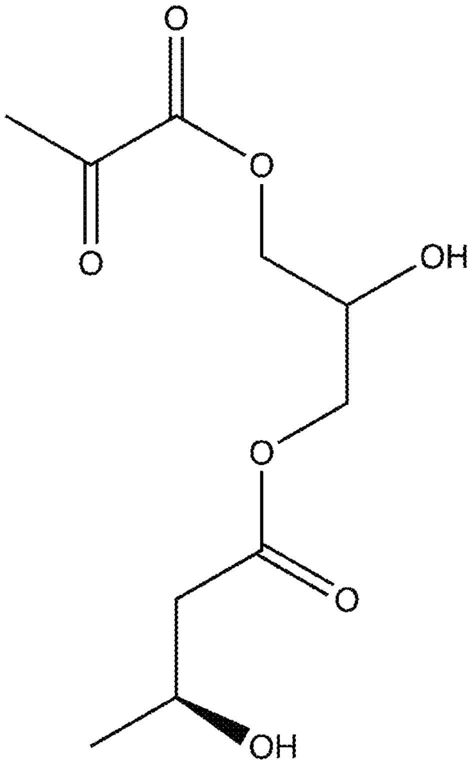
Figure 82:
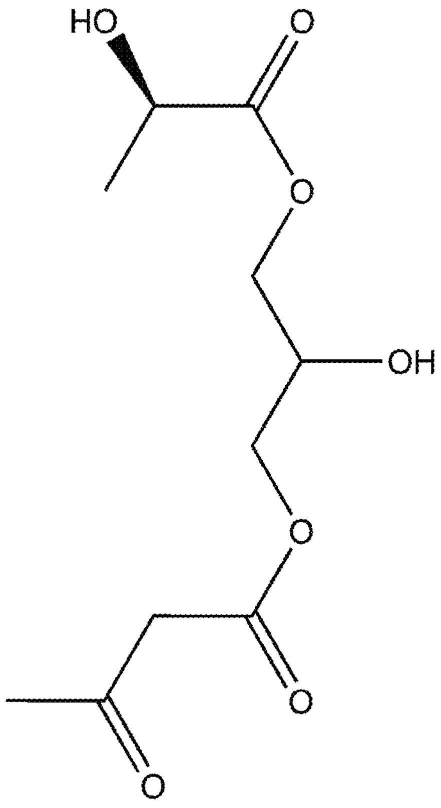
Figure 83:
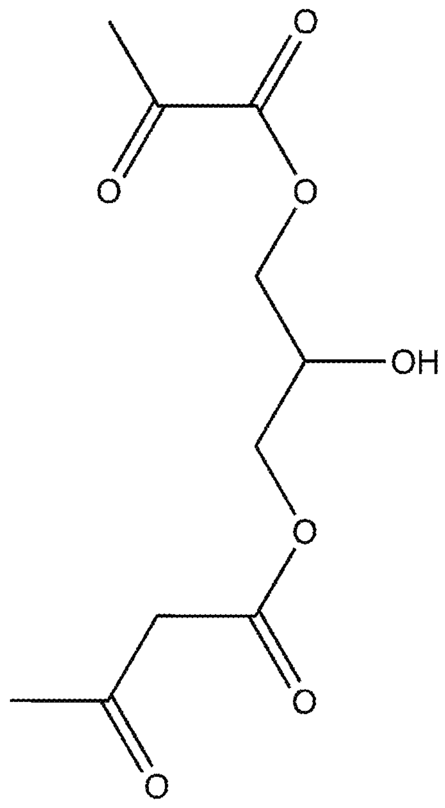
Figure 84:
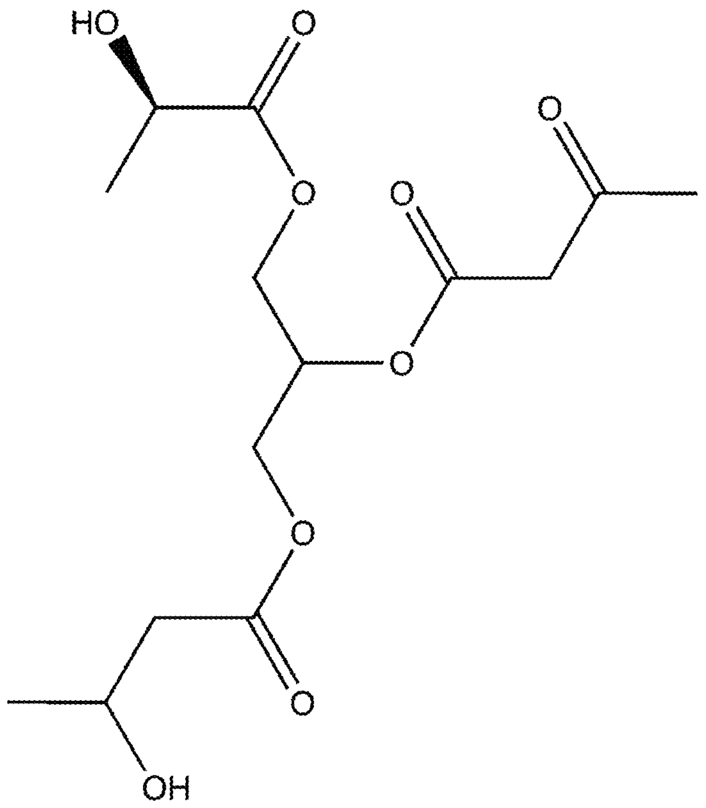
Figure 85:
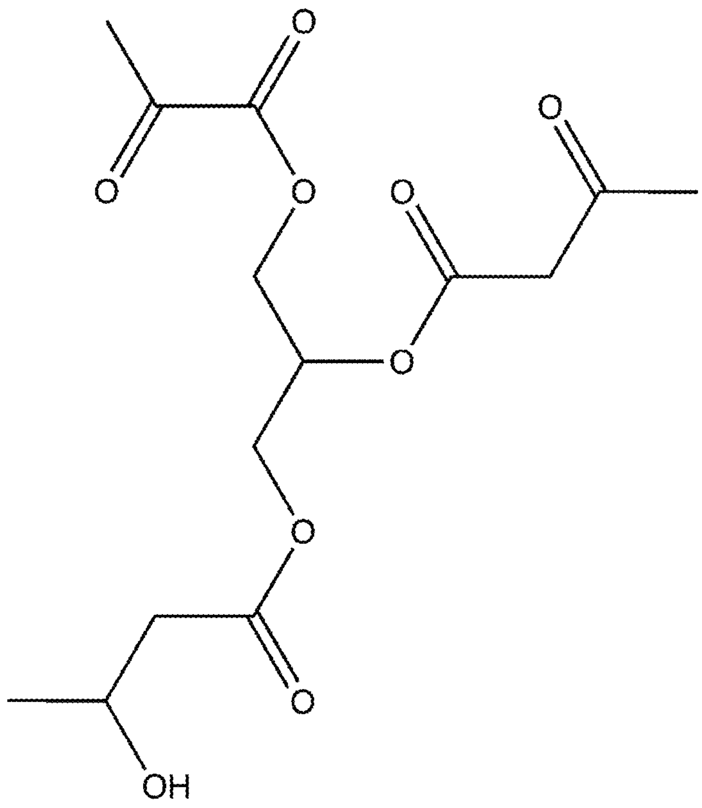
Figure 86:
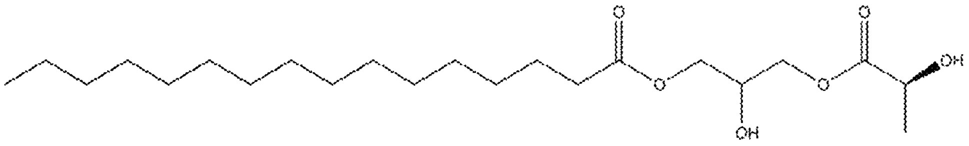
Figure 87:
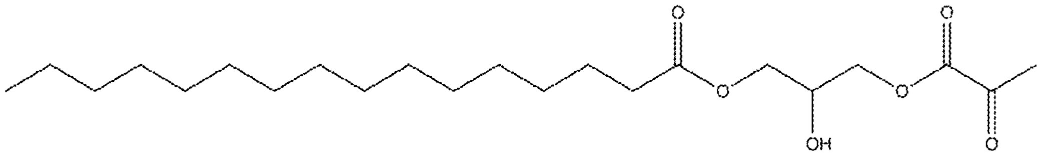
Figure 88:
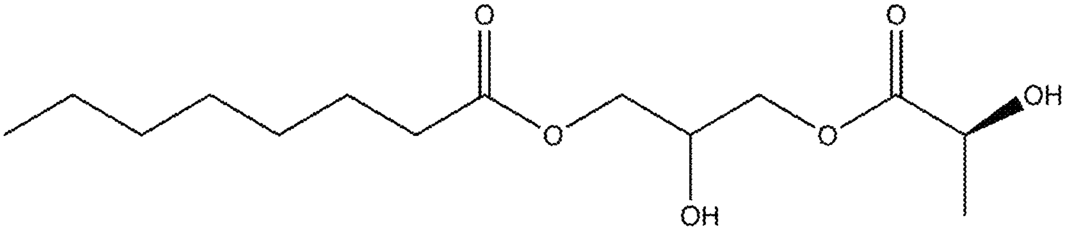
Figure 89:
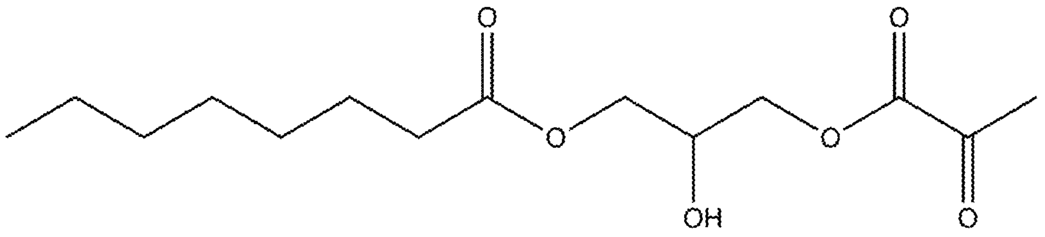
Figure 90:
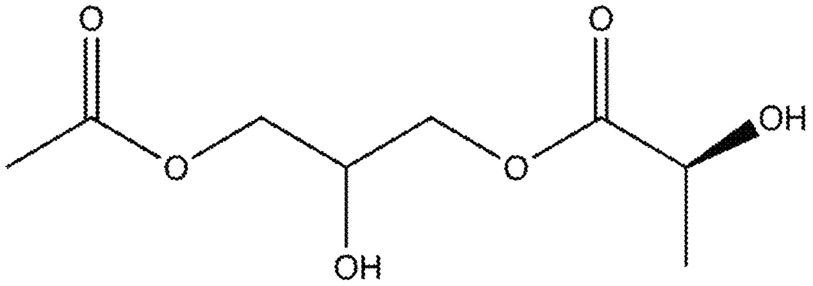
Figure 91:
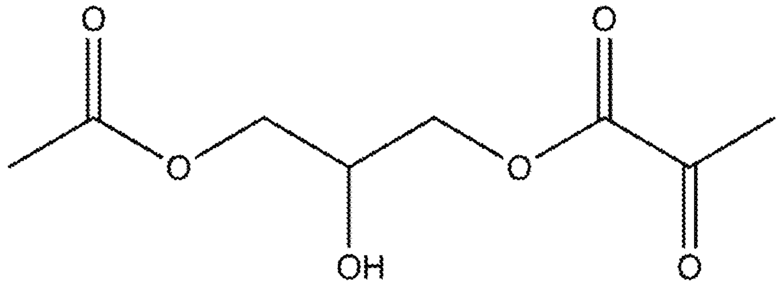
Figure 92:
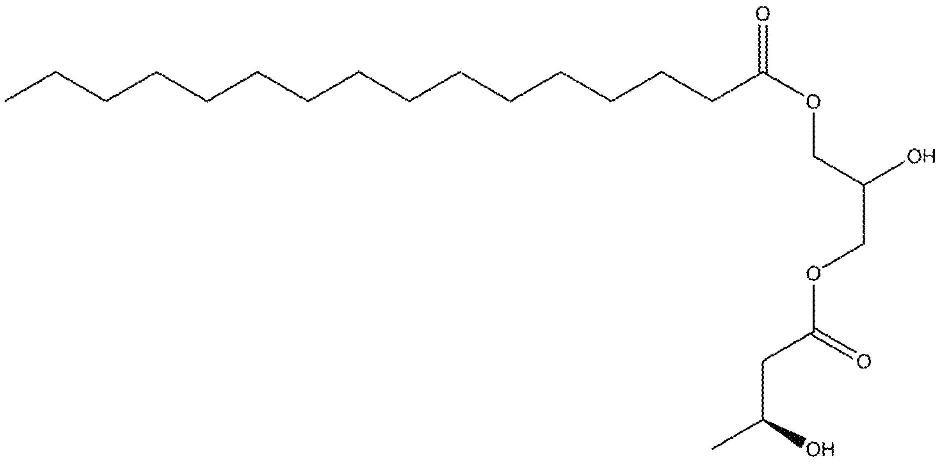
Figure 93:
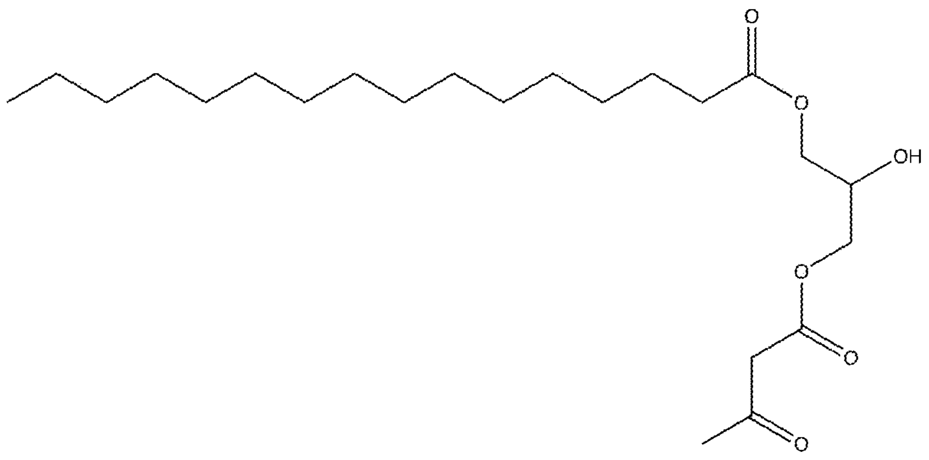
Figure 94:
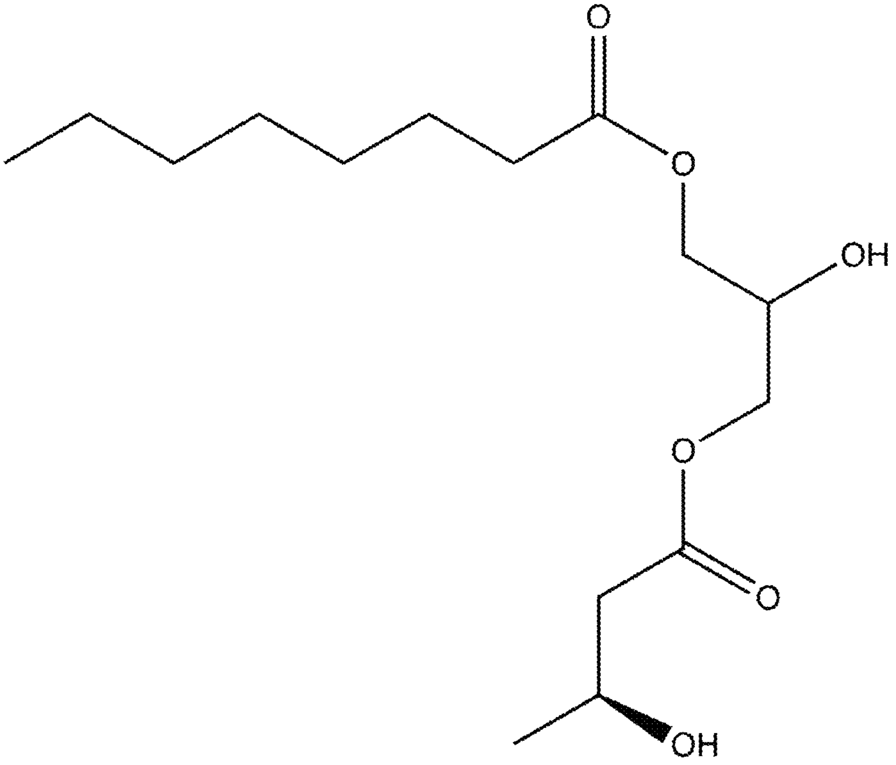
Figure 95:
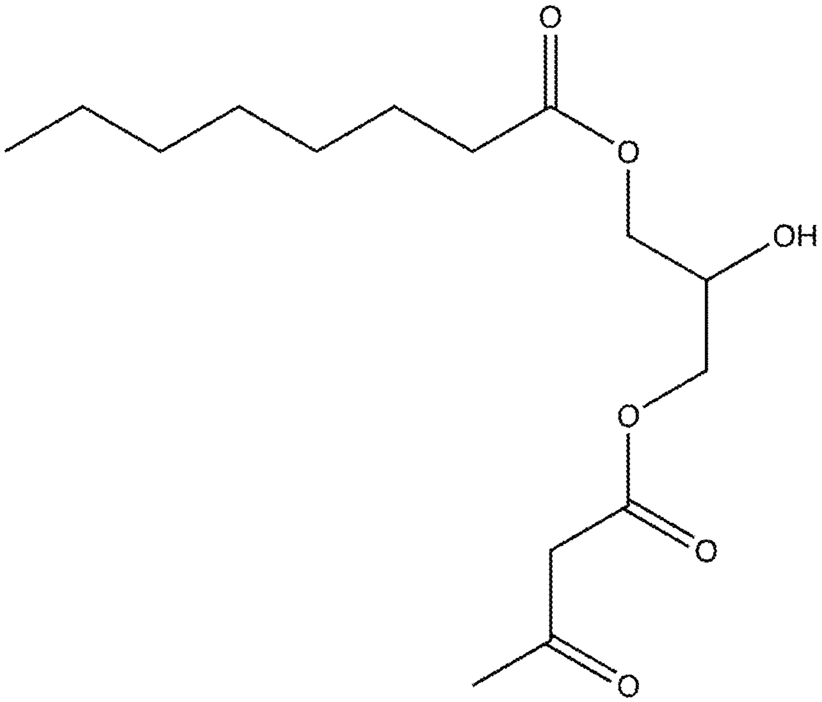
Figure 96:
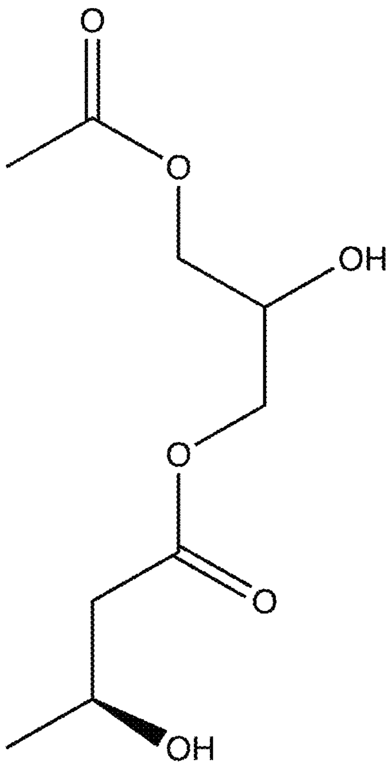
Figure 97:
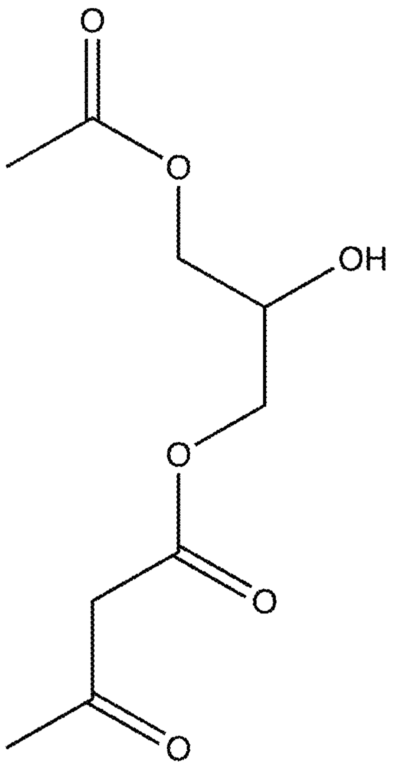
Figure 98:
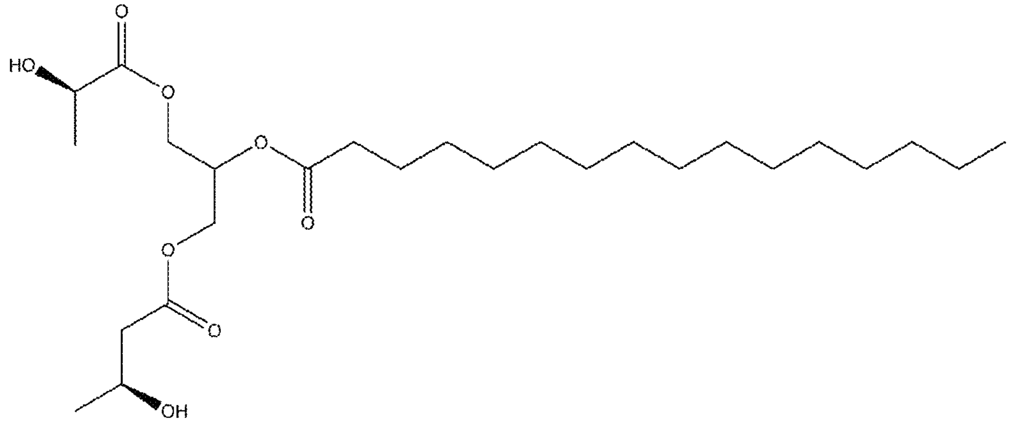
Figure 99:
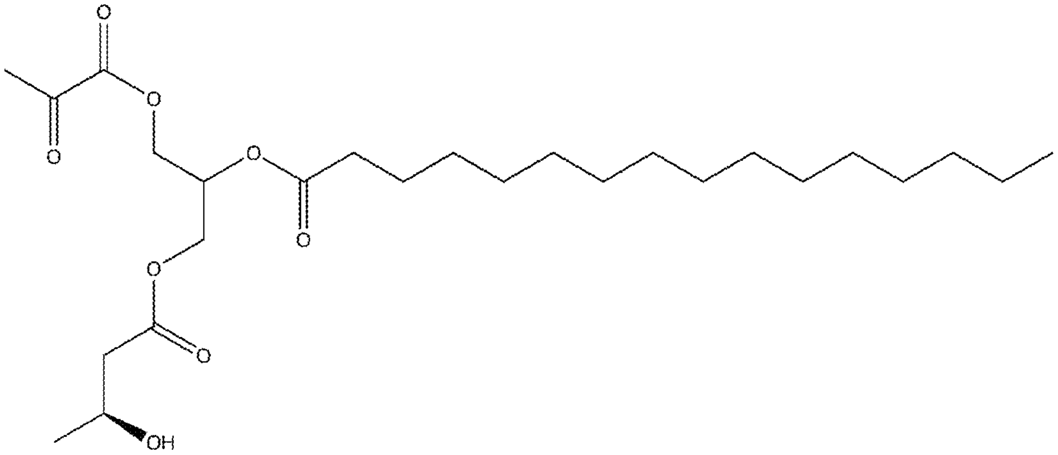
Figure 100:
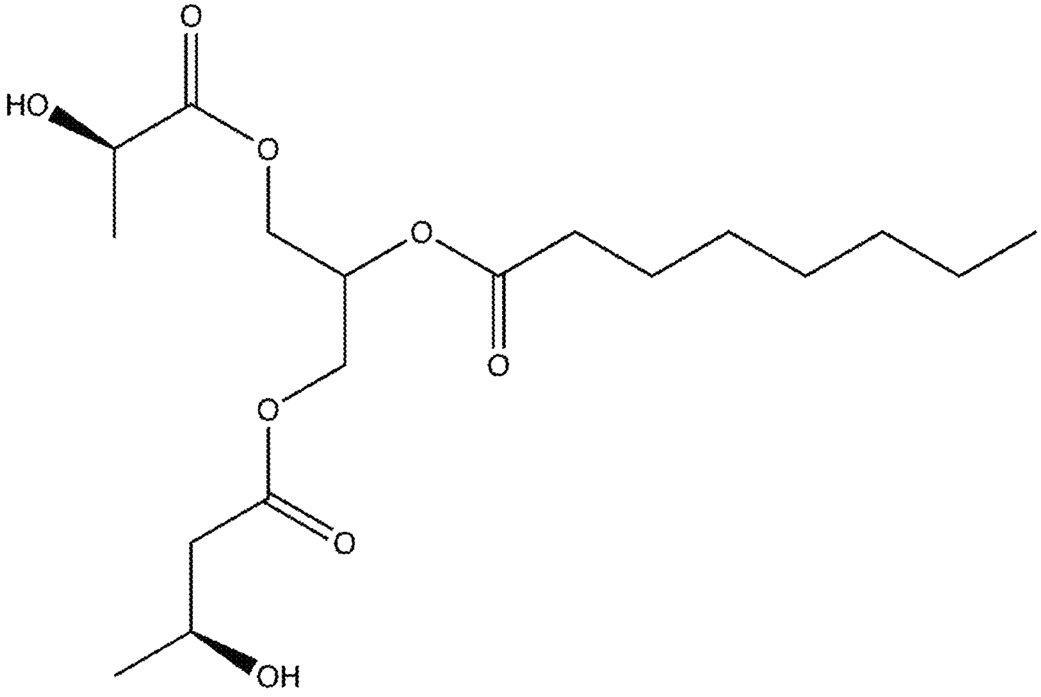
Figure 101:
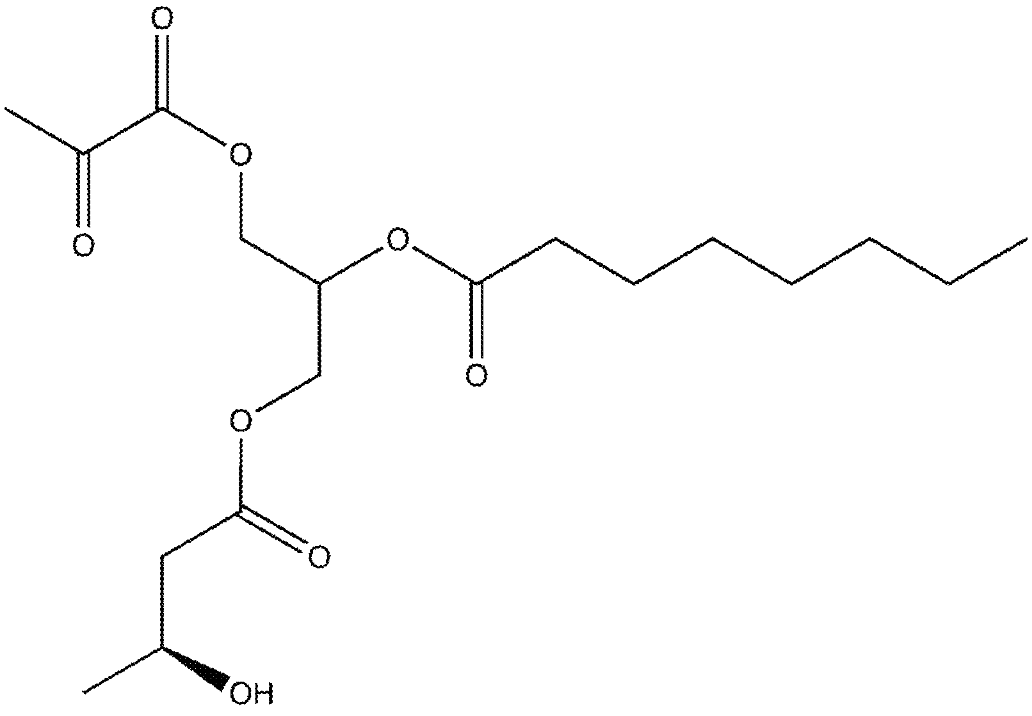
Figure 102:
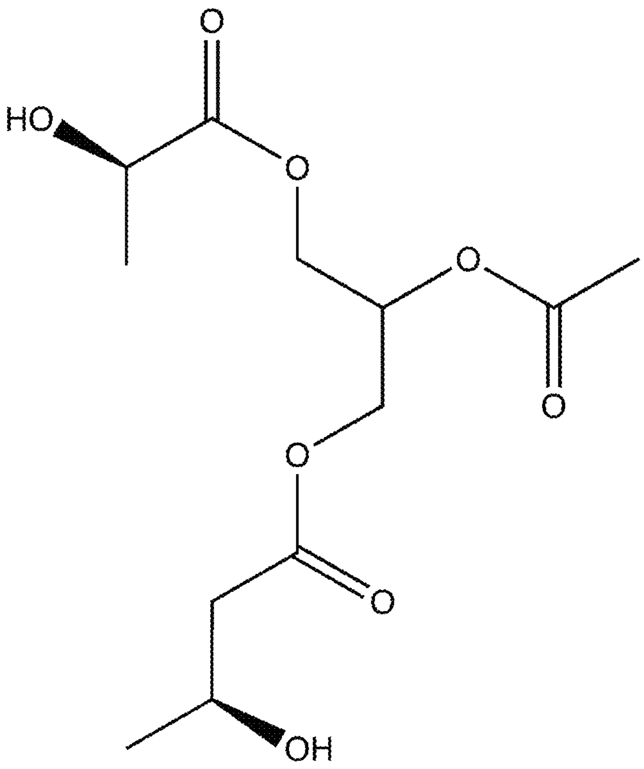
Figure 103:
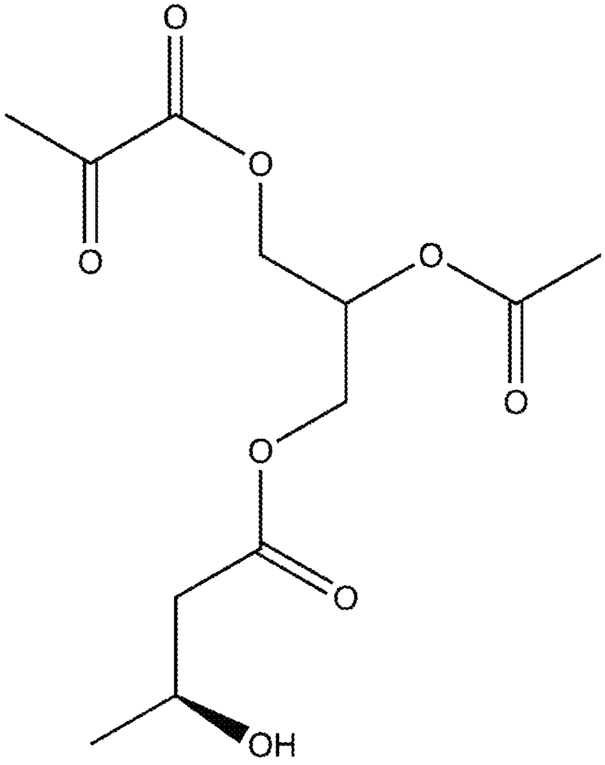
Figure 104:
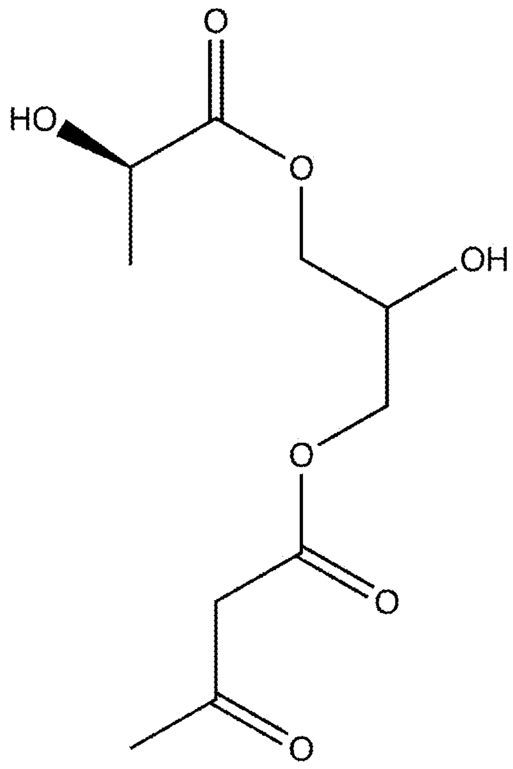
Figure 105:
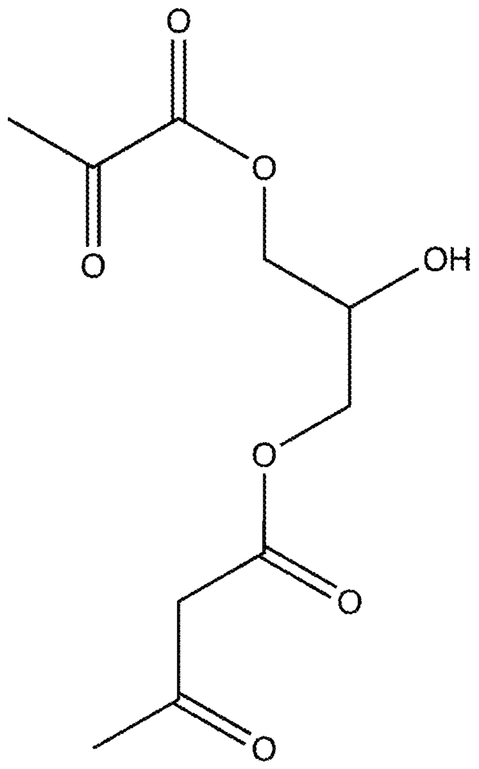
Figure 106:
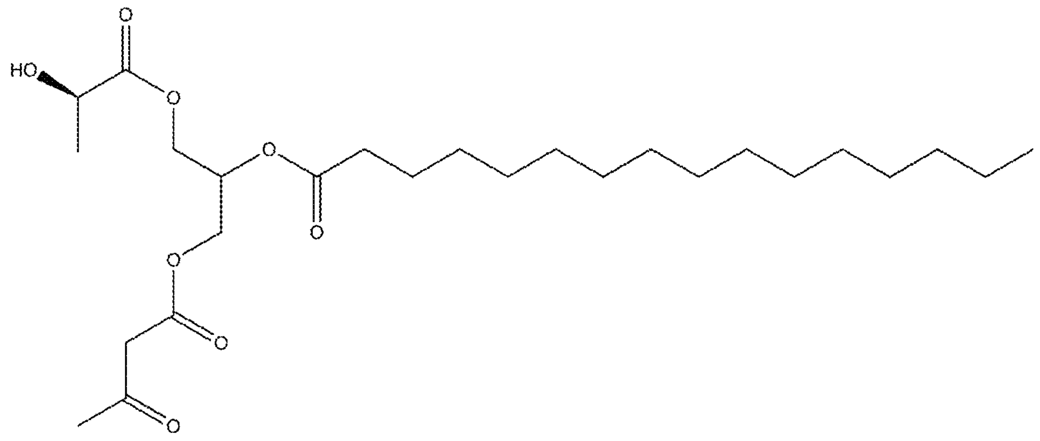
Figure 107:
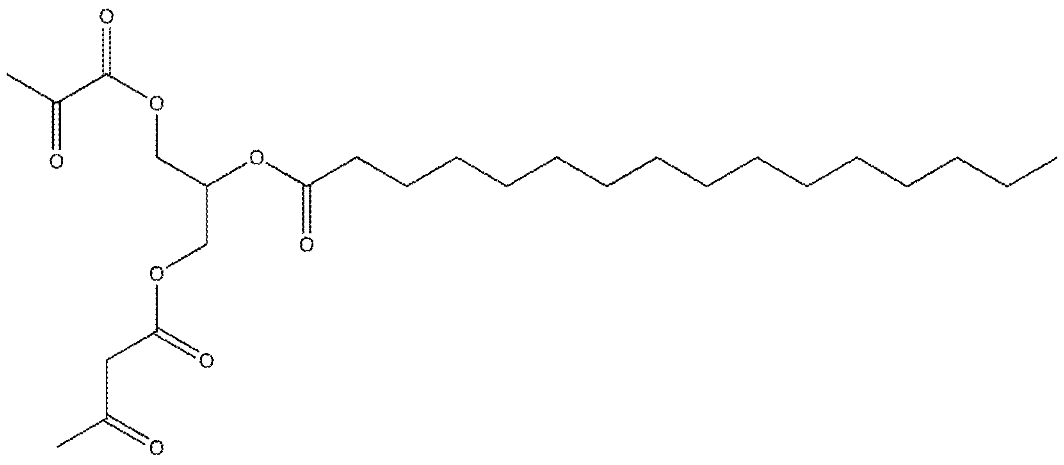
Figure 108:
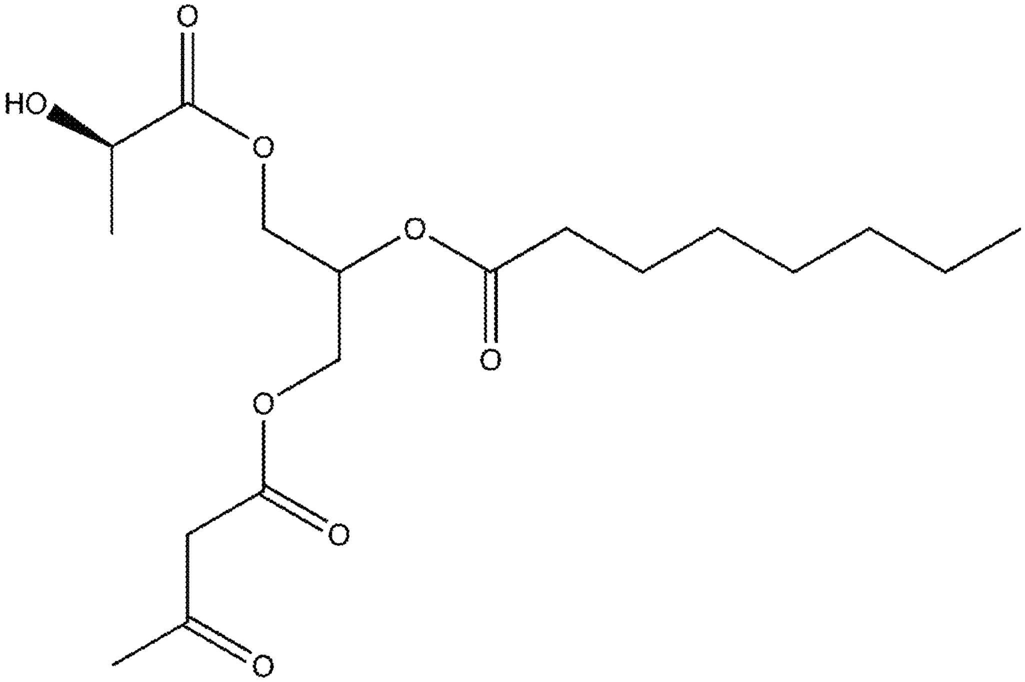
Figure 109:
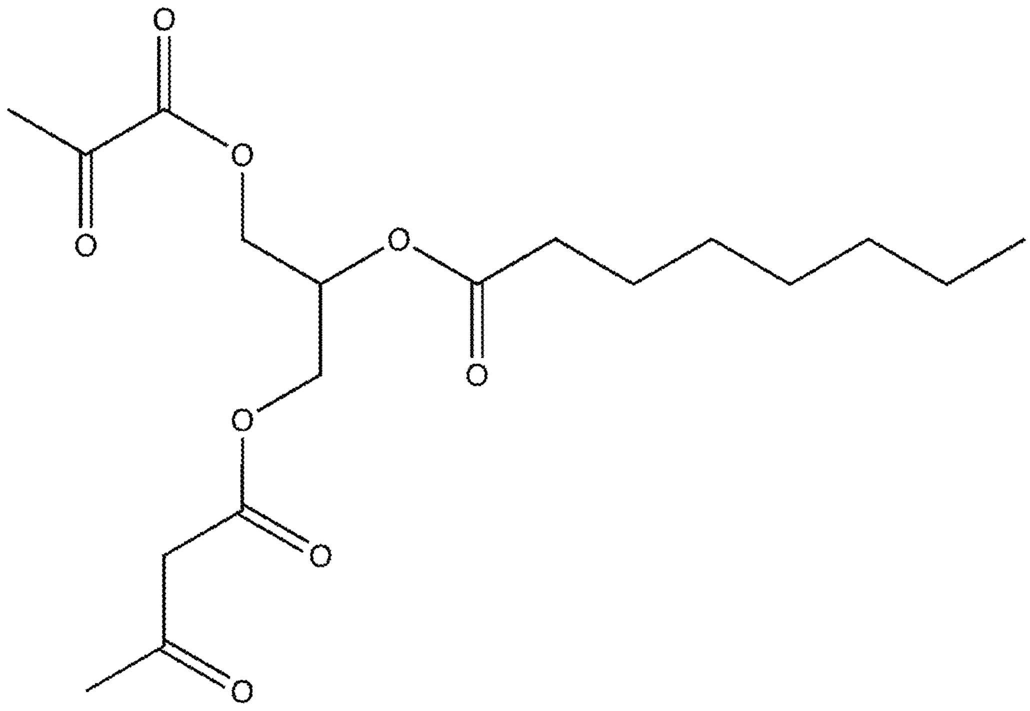
Figure 110:
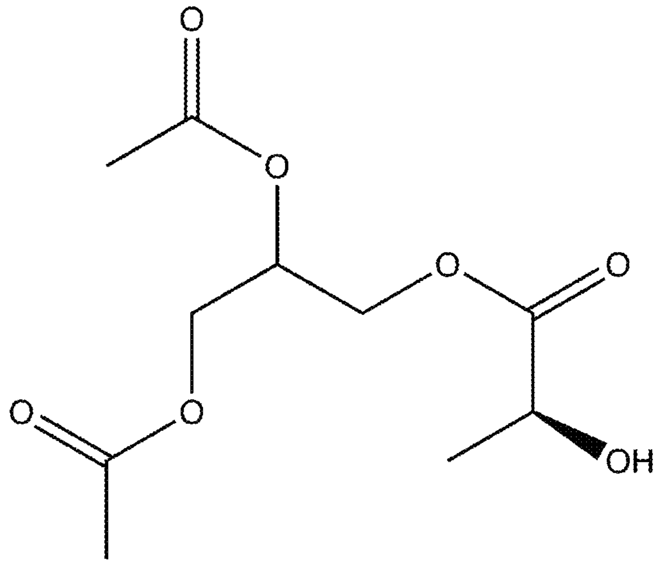
Figure 111:
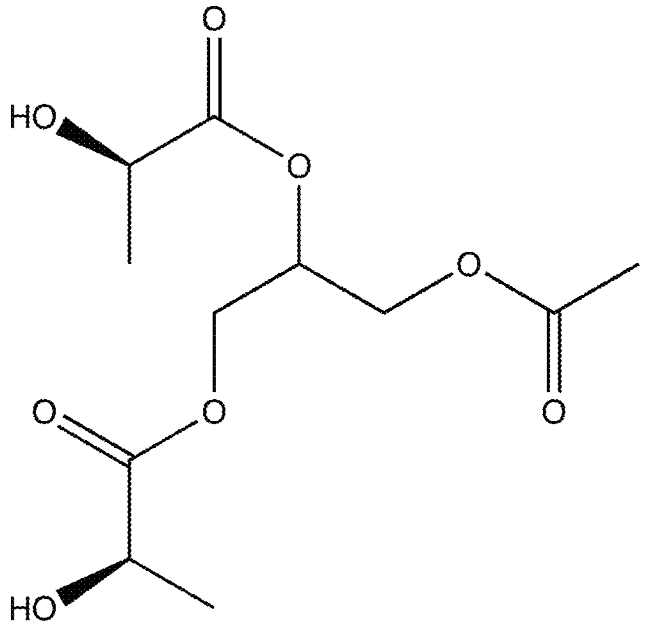
Figure 112:
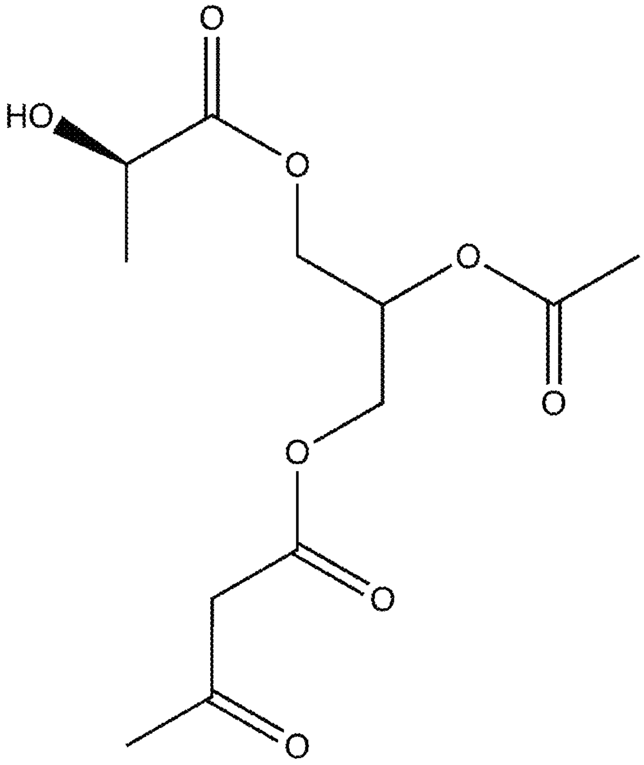
Figure 113:
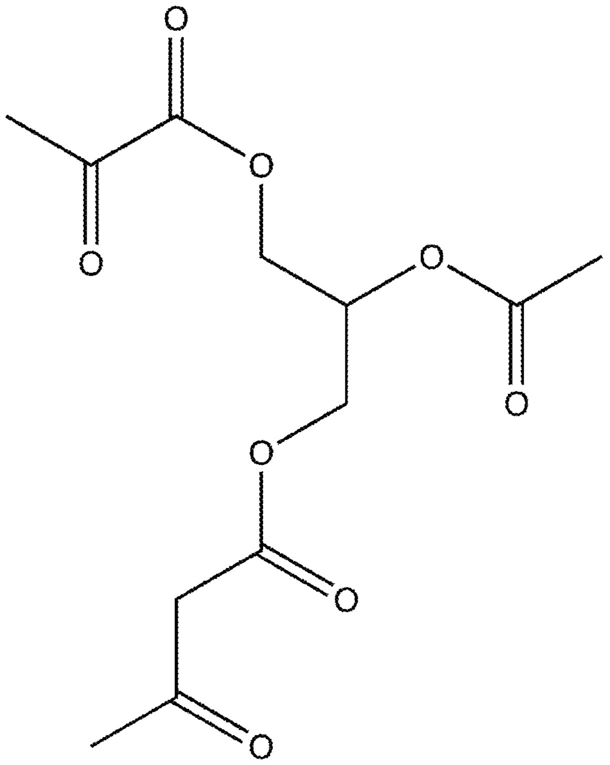

FIG. 23 illustrates such a glycerol backbone molecule the glycerol backbone and three groups $B_1$, $B_2$, $B_3$, wherein one or more of the B groups may correspond to one of the functional energy groups $A_1$, $A_2$ or $A_3$, as described. Glycerol and glycerol backbone have the added advantage in a formulation of being a hydrating agent, as discussed below. As well, the glycerol backbone has the advantage of being able to carry one, two, or three functional energy groups A. In another embodiment of the invention one or more of the $B_1$, $B_2$, $B_3$, groups may simply be hydrogen (H), in other words, essentially no functional group at that position.

Figure 125:
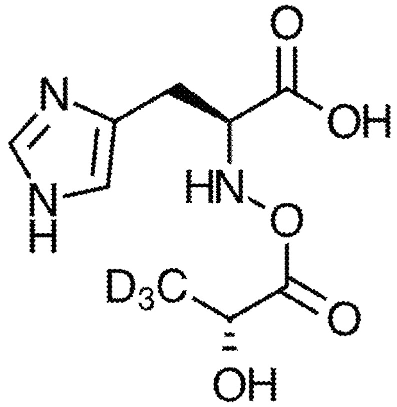

One, two, or even three of those functional groups (A) can be attached to the same molecule, in a preferred embodiment, to a glycerol backbone. Alternatively, the glycerol backbone can carry merely one or two of those functional groups. The one or more (anion) energy substrate groups (functional groups) of biological viability can be attached. Thus one or more of the A groups may be to the same glycerol backbone molecule, in other words a carbon (C) with an oxygen (O) (C—O), and each of the functional groups A is connected to the O, typically by a single bond (in other words, esterified to the glycerol backbone). FIGS. 22-125 illustrate some of the many possible variations of this glycerol backbone and associated functional groups.

Carriers R can be viable energy substrates in and of themselves that are attached to said other biologically viable energy substrates A. Carriers R and energy substrates A are readily transported from the intestine into the systemic blood circulation by independent transport mechanisms and subsequently moved around the body via the systemic circulation.

Examples of Combinations of RA Molecules Such as $R_1A_1$, $R_2A_1$, $R_3A_1$, $R_1A_2$, $R_2A_2$, $R_3A_2$, $R_1A_3$, $R_2A_3$, $R_3A_3$)

$R_1A_1$

In the formulation of the invention molecules with $R_1A_1$ cation carrier and anion energy configuration can included molecules, such as Sodium Lactate, Potassium Lactate, Magnesium lactate, Calcium lactate, Sodium Pyruvate, Potassium Pyruvate, Magnesium Pyruvate, Calcium Pyruvate, their derivatives and mixtures of them that center around levels found in blood of healthy individuals. Sodium ion ($Na^+$) is the main cation in plasma, normally 145 mEq/L; other cations are far less abundant in plasma. For instance, normal values for $K^+$, $Ca^{++}$, and $Mg^{++}$ are, respectively, 4, 2.5 and 1.5 mEq/L respectively. Hence, a mixture of inorganic cation salts when $A_1$ is lactate or pyruvate, $R_1$ would be made of $Na^+$, $K^+$, $Ca^{++}$, and $Mg^{++}$ in the ratio of 145, 4, 2.5, and 1.5. In this $A_1$ embodiment of invention, the main anion would be lactate or pyruvate, but phosphates ($PO_4^{3-}$), hydrogen phosphate ($HPO_4^{2-}$) and dihydrogen phosphate ($H_2PO_4^-$), in the amount of 1.0 mEq would be provided as well to support electro-neutrality in blood.

$R_2A_1$

In the formulation of the invention molecules with $R_2A_1$ cation carrier and anion energy configuration can included molecules, for example glycerol mono-pyruvate, glycerol di-pyruvate, glycerol tri-pyruvate, glycerol mono-lactate, glycerol di-lactate, glycerol tri-lactate, glycerol-lactate N-acetyl cysteine thiolester (LNACE), lactate N-acetyl methionine thiolester (LNAME), their derivatives and mixtures of them. Again, boundaries of mixture and tonicity stated above and illustrated in FIGS. 1-21 for beverages and gels apply also to RA energy substrates and the intended mode of delivery; specifically for delivery via beverage or gel: ≈300 mEq/L, 1,000≤mEq/L, and <1,000 mEq/L.

$R_3A_1$

In the formulation of the invention molecules with $R_3A_1$ cation carrier and anion energy configuration can included molecules, for example arginyl-lactate, arginyl-pyruvate, arginyl-alanine, their derivatives and mixtures of them. Other $R_3$ cation carriers such as lysine, cysteine and histidine can be used in place of arginine with the $A_1$ energy substrates. Again, boundaries of mixture and tonicity stated above and illustrated in FIGS. 1-21 for beverages and gels apply also to RA energy substrates and the intended mode of delivery; specifically for delivery via beverage or gel: ≈300 mEq/L, 1,000≤mEq/L, and <1,000 mEq/L.

$R_1A_2$

In the formulation of the invention molecules with $R_1A_2$ cation carrier and anion energy configuration can included molecules, for example Sodium acetoacetate, Potassium acetoacetate, Magnesium acetoacetate, Calcium acetoacetate, Sodium beta-hydroxybutyrate, Potassium beta-hydroxybutyrate, Magnesium beta-hydroxybutyrate, Calcium beta-hydroxybutyrate, their derivatives and mixtures of them. Again, boundaries of mixture and tonicity stated above and illustrated in FIGS. 1-21 for beverages and gels apply also to RA energy substrates and the intended mode of delivery; specifically for delivery via beverage or gel: ≈300 mEq/L, 1,000≤mEq/L, and <1,000 mEq/L.

$R_2A_2$

In the formulation of the invention molecules with $R_2A_2$ cation carrier and anion energy configuration can included molecules, for example glycerol mono-acetoacetate, glycerol di-acetoacetate, glycerol tri-acetoacetate, glycerol mono-beta-hydroxybutyrate, glycerol di-beta-hydroxybutyrate, glycerol tri-beta-hydroxybutyrate, their derivatives and mixtures of them. Again, boundaries of mixture and tonicity stated above and illustrated in FIGS. 1-21 for beverages and gels apply also to R or RA energy substrates and the intended mode of delivery; specifically for delivery via beverage or gel: ≈300 mEq/L, 1,000≤mEq/L, and <1,000 mEq/L.

$R_3A_2$

In the formulation of the invention molecules with $R_3A_2$ cation carrier and anion energy configuration can included molecules, for example, arginyl-acetoacetate, arginyl-beta hydroxybutyrate, their derivatives and mixtures of them. Other $R_3$ cation carriers such as lysine, cysteine and histidine can be used in place of arginine with the $A_2$ energy substrates. Again, boundaries stated above and illustrated in FIGS. 1-21 for beverages and gels apply also to RA energy substrates and the intended mode of delivery; specifically for delivery via beverage or gel: ≈300 mEq/L, 1,000≤mEq/L, and <1,000 mEq/L.

$R_1A_3$

In the formulation of the invention molecules with $R_1A_3$ cation carrier and anion energy configuration can included molecules, for example Sodium acetate, Potassium acetate, Magnesium acetate, Calcium acetate, Sodium octanoate, Potassium octanoate, Magnesium octanoate, Calcium octanoate, Sodium palmitate, Potassium palmitate, Magnesium palmitate, Calcium palmitate, Sodium oleate, Potassium oleate, Magnesium oleate, Calcium oleate, Sodium stearate, Potassium stearate, Magnesium stearate, Calcium stearate, their derivatives and mixtures of them. Again, boundaries stated above and illustrated in FIGS. 1-21 for beverages and gels apply also to RA energy substrates and the intended mode of delivery; specifically for delivery via beverage or gel: ≈300 mEq/L, 1,000≤mEq/L, and <1,000 mEq/L.

$R_2A_3$

In the formulation of the invention molecules with $R_2A_3$ cation carrier and anion energy configuration can included molecules, for example glycerol mono-acetate, glycerol di-acetate, glycerol tri-acetate, glycerol mono-octanoate, glycerol di-octanoate, glycerol tri-octanoate, glycerol mono-palmitate, glycerol di-palmitate, glycerol tri-palmitate, glycerol mono-oleate, glycerol di-oleate, glycerol tri-oleate, glycerol mono-stearate, glycerol di-stearate, glycerol tri-stearate, their derivatives and mixtures of them. Again, boundaries of mixture and tonicity stated above and illustrated in FIGS. 1-21 for beverages and gels apply also to RA energy substrates and the intended mode of delivery; specifically for delivery via beverage or gel: ≈300 mEq/L, 1,000≤mEq/L, and <1,000 mEq/L.

$R_3A_3$

In the formulation of the invention molecules with $R_3A_3$ cation carrier and anion energy configuration can included molecules, for example Arginyl acetate, Arginyl-octanoate, Arginyl-palmitate, Arginyl-oleate, Arginyl-stearate, their derivatives and mixtures of them. Other $R_3$ cation carriers such as lysine, cysteine and histidine can be used in place of arginine with the $A_3$ energy substrates. Again, boundaries of mixture and tonicity stated above and illustrated in FIGS. 1-21 for beverages and gels apply also to RA energy substrates and the intended mode of delivery; specifically for delivery via beverage or gel: ≈300 mEq/L, 1,000≤mEq/L, and <1,000 mEq/L.

Note that as in the stated example formulations, the following claims are based on the concept of a biologically viable carrier (R) being used to provide a biologically viable energy substrate (A) is applied. As well, in some cases the R-A concept is augmented by additions of sugars and starches as often provided in sports drinks and hydrating fluids. In particular, note also that formulas 15-21 have been annotated to indicate classes of energy substrate anions; specifically as indicated in the application, in combinations with each other wherein $A_1$=lactate, pyruvate, $A_2$=acetoacetate, beta hydroxybutyrate and $A_3$=acetate, octanoate, palmitate, oleate, etc., and R can be any R group specified in the application. To reiterate from the above, $R_1$ are the inorganic cations of Sodium ($Na^+$), Potassium ($K^+$), Magnesium ($Mg^{++}$) and Calcium ($Ca^{++}$) plus mono- and di-phosphorous ($H_2PO_4$ and $H_2PO_{3s}$) in ratios as they exist in human blood; $R_2$ are mono-, di- and tri-esters of glycerol (i.e., glycerol esters) and thiol esters of amino acids and their derivatives; and, —$R_a$ are the amino acids arginine, lysine, cysteine, histidine and their derivatives.

According to preferred embodiments, molecules of the invention may include:

- lactate anion (Lac) and its derivatives also with biological viability, in particular arginine or glycerol derivatives, such as Arginyl L-(+)-Lactate, Histidine L-(+)-Lactate, Lysine L-(+)-Lactate, glutamine L-(+)-Lactate, Glycerol Tri-L-(+)-Lactate, Glycerol Di-L-(+)-Lactate, Glycerol Mono-L-(+)-Lactate, Glycerol Tri-Palmitate, Glycerol Mono-L-(+)-Lactate-Di-Palmitate, Glycerol Di-L-(+)-Lactate-Mono-Palmitate, Glycerol Tri-Octanoate, Glycerol Mono-L (+)-Lactate-Di-Octanoate or Glycerol Di-L (+)-Lactate-Mono-Octanoate;
- pyruvate anion (Pyr) and its derivatives also with biological viability, in particular are arginine or glycerol derivatives, such as Sodium Pyruvate, Arginyl Pyruvate, Histidine Pyruvate, Lysine Pyruvate, Glutamine Pyruvate, Glycerol Tri-Pyruvate, Glycerol Di-Pyruvate, Glycerol Mono-Pyruvate, Glycerol Mono-Pyruvate or Di-Glycerol Di-Pyruvate-Mono-Palmitate;

acetate anion (Ace) and its derivatives also with biological viability, in particular Glycerol Tri-Acetate, Glycerol Di-Acetate, Glycerol Mono-Acetate, Glycerol Mono-Acetate-Di-L-(+)-Lactate, Glycerol Di-Acetate-Mono-L-(+)-Lactate, Glycerol Mono-Acetate-Di-Palmitate, Glycerol Di-Acetate-Mono-Palmitate, Glycerol Mono-Acetate-Di-L-(+)-Lactate, Glycerol Di-Acetate-Mono-L-(+)-Lactate, Glycerol, Glycerol Mono-Acetate-Di-Palmitate, Glycerol Di-Acetate-Mono-Palmitate or Glycerol Tri-Acetate;

acetoacetate anion (AcAc) and its derivatives also with biological viability, in particular Glycerol Tri-acetoacetate, Glycerol Di-Acetoacetate, Glycerol Mono-acetoacetate, Glycerol Mono-Acetoacetate-Di-L-(+)-Lactate, Glycerol Di-Acetoacetate-Mono-L-(+)-Lactate, Glycerol Mono-Acetoacetate-Di-Palmitate, Glycerol Di-Acetoacetate-Mono-Palmitate, Glycerol Mono-Acetoacetate-Di-L-(+)-Lactate, Glycerol Di-Acetoacetate-Mono-L-(+)-Lactate, Glycerol, Glycerol Mono-Acetoacetate-Di-Palmitate, Glycerol Di-Acetoacetate-Mono-Palmitate or Glycerol Triacetoacetate;

beta-hydroxybutyrate anion (BOHB) and its derivatives also with biological viability, in particular Beta-Hydroxybutyrate (BOHB), Glycerol Tri-beta-Hydroxybutyrate, Glycerol Di-beta-Hydroxybutyrate-mono acetoacetate, Glycerol Mono-beta-Hydroxybutyrate-Di Acetoacetate, Glycerol-beta-Hydroxy-beta mono-L-(+)-Lactate or Glycerol Mono-beta-Hydroxybutyrate-Di-L-(+)-Lactate;

palmitate anion and its derivatives also with biological viability, in particular sodium palmitate (Palm), Glycerol Tri-Palm, Glycerol Di-Palm-mono acetoacetate, Glycerol Mono-Palm-Di Acetoacetate, Glycerol-Palm-(+)-Lactate or Glycerol Mono-Palm-Di-L-(+)-Lactate;

octanoate anion and its derivatives also with biological viability, in particular sodium octanoate (Oct), Glycerol Tri-Oct, Glycerol Di-Oct-mono acetoacetate, Glycerol Mono-Oct-Di Acetoacetate, Glycerol-Oct-(+)-Lactate or Glycerol Mono-Oct-Di-L-(+)-Lactate.

In addition to providing energy in the form of carbohydrates, including mono- and di-saccharides (sugars) and maltodextrins (glucose polymers and other forms of starches), using our unique formulations energy can be provided as a type of carbohydrate in the form of an MCC of GNG precursor such as lactate or pyruvate. For example, in the formulations of the invention, FIGS. 1-21, which contain some of the molecules of the invention, it is possible to provide carbohydrate energy in forms not typically identified as sugars and starches. Instead, the energy forms are lactate and pyruvate, downstream products of sugar and carbohydrate metabolism. The types of individuals who would benefit from the invention are identified as CrossFit athletes (a trademarked name) and keto athletes, as well as diabetics or others with glucose intolerance and insulin resistance.

The range of percentages of particular functional groups (and molecules in the formulations below) will vary according to the carrier (e.g., $R_1$, $R_2$, $R_3$) energy substrate relationships of the A (e.g., $A_1$, $A_2$, $A_3$) energy functional groups depending on the valences of radical groups R to which they are attached. The nature and variety of these A functional groups is discussed more below.

One, two, or even three of those functional groups (A) can be attached to the same molecule, in a preferred embodiment, to a glycerol backbone, as discussed. Alternatively, the glycerol backbone can carry merely one or two of those functional groups. The one or more (anion) energy substrate groups (functional groups) of biological viability can be attached.

For instance, if R is arginine-based and A is lactate or pyruvate, the ratio is 1:1. Alternatively, if the R is glycerol and one or more As are lactate, pyruvate, acetate, acetoacetate, beta-hydroxybutyrate, octanoate or palmitate the ratio can be 1:1, 1:2 or 1:3. Moreover, the 1:2 and 1:3 ratios are not fixed to a single moiety (A), but might be an acetate, lactate and palmitate, or two lactates and one palmitate, etc. In the invention the molecule or molecules can be glycerol mono-pyruvate, glycerol di-pyruvate, glycerol tri-pyruvate, glycerol mono-lactate, glycerol di-lactate, glycerol tri-lactate, glycerol-lactate N-acetyl cysteine thiolester (LNACE), lactate N-acetyl methionine thiolester (LNAME), their derivatives and mixtures of them.

Inventors Research Support for the Energy Functional Groups and Carrier Groups Described Actions of Metabolites and Electrolytes in Physiological Solutions: In chemistry and physiology, a "solution" is a homogeneous solvent in which one of more solutes can be dissolved. An "aqueous solution" is one in which the solvent is water. In chemistry, numerous solutes, such as inorganic and organic salts and metabolites such as MCCs and GNG precursors, are highly soluble. In physiology, inorganic and organic salts and metabolites readily dissolve in body fluids, such as blood plasma and intracellular body water compartments that include most (≈70-75%) of body volume and mass in humans depending on the level of obesity. Also in physiology, not only are inorganic and organic salts and metabolites dissolved in body water, but they are also carried around the body in aqueous solutions of blood and lymph. Importantly also in physiology numerous enzymatic reactions are catalyzed in discrete body water compounds. Miscibility—Miscibility refers to the ability of substances to mix in homogeneous solutions such as body water. Miscibility also refers to the ability of different components of body water to mix homogeneously in plasma and other body fluids, such as lymph that enters the systemic circulation through the thoracic duct.

Lactate, short, medium and long chain fatty acids and amino acids as well as ketone bodies can be used alone or formulated together in a composition to benefit the body energy state of an individual with health and wellness outcomes that are beneficial. Herein the invention describes both new chemical entities and new formulations of new chemical entities and existing chemical entities to benefit the individual in healthy resting or exercising conditions and ill and injured states.

Different mechanisms for transport from the intestine into the blood exist such as the sodium-mediated transporter protein for glucose (sGLUT). Alternatively, lactate and pyruvate use different transporters at both the intestinal and cellular levels as compared with glucose. As well, ketone bodies share the same cellular transporter with lactate, but lactate is preferentially oxidized. As such, a novel chemical entity containing both lactate and ketone bodies that is easily hydrolyzed in the gut to its constituent parts can provide short- and medium-term cellular energy as well as signaling properties using multiple metabolic pathways and membrane proteins.

Fatty acids vary depending on the length of the carbon chain and depending on the length are transported through the intestine into the blood stream. Because of the various transport mechanisms that exist for fatty acids and the differences between fatty acid transport, lactate transport and ketone body transport, novel chemical entities contain combinations wherein any of the energy sources exist and are easily hydrolyzed to their constituent components in the gut can deliver fuel energy for different intensities of exercise, different durations of exertion as well as beneficial outcome measures for the ill and injured.

Carriers for Lactate and Acetate Anions, Gluconeogenic (GNG) precursors and Monocarboxylate Compounds (MCC): Compounds and molecules can be identified to deliver fluid, electrolytes and metabolites to support diverse functions in the ill and injured as well as healthy individuals under exercise, thermal and other stresses. Ideally, the carriers themselves will have physiological and metabolic efficacy (e.g., $Na^+$ ion for electrolyte replacement, arginine [a nitric oxide (NO) precursor and vasodilator), and glycerol (a plasma volume expander and GNG precursor).

Salts as Nutrient Carriers: Salts are ionic compounds that result from the neutralization reaction of an acid and a base. They are composed of related numbers of counter ions, specifically anions (negatively charged ions) and cations (positively charged ions) such that the product is without net charge and is electrically neutral. The component ions can both be inorganic, such as the combination of sodium ($Na^+$) and chloride ($Cl^-$) to yield NaCl, or organic (carbon-based), such as acetate ($C_2H_3O_2^-$) or lactate ($C_3H_5O_2^-$) and a basic positively charged amino acid, such as Arginine ($Arg^+$), to yield Arginyl-Acetate or Arginyl-Lactate (Arg-Lac), or a combination of inorganic and organic ions, for example the combination of sodium ($Na^+$) and lactate to yield sodium-lactate (Na-Lac). As well, salts can be monatomic, such as sodium-lactate, or polyatomic, such as in the combination of calcium ($Ca^{2+}$), or magnesium ($Mg^{2+}$) and Chloride to yield $MgCl_2$ and $CaCl_2$), respectively, or calcium and magnesium in combination with lactate anion to yield calcium-lactate [$CaLac_2$, $Ca(C_3H_5O_2^-)_2$] or magnesium-lactate [$MgLac_2$, $Mg(C_3H_5O_2^-)_2$]. In parallel, the same can be said for inorganic salts and basic amino acids as acetate carriers.

Solubility and Dissociation of Salts In Aqueous Solution: Many ionic compounds are highly soluble in water. Further, depending on pH and dissociation constants (pKa's) of salts in water, the ionic bonds holding anions and cations readily disassociate to free anions and cations, each then carrying their respective negative and positive charges. The exact combination of ions involved makes each compound have a unique solubility in a solvent such as water. The aqueous solubility is dependent on how well each ion interacts with the solvent, so there are certain patterns. For example, the salts of sodium noted above are soluble in water, whereas the salts of basic amino acids (e.g., Arg-Lac) are relatively insoluble at alkaline pH (i.e., above pKa), but readily dissociate at acid pH (i.e., below pKa). Hence, it is possible to manufacture compounds, such as Arginyl-lactate in an alkaline aqueous solution that when separated from water yields a stable, dry powder. However, powdered arginyl-lactate can be suspended and dissolves in a pH neutral or slightly alkaline aqueous solution. Moreover, Arg-Lac will rapidly dissociate to an arginine cation ($Arg^+$) and a lactate anion ($Lac^-$) in an acid or neutral pH environment, such as exists in the stomach, or the blood of a living human or other mammal.

Metabolite, Electrolyte and Fluid Uptake: A distinct advantage of using combinations of ionic electrolyte, MCC and GNG precursor compounds to support the ill, injured and environmentally stressed as well as healthy individuals under exercise or thermal stresses is that they are readily miscible in aqueous solutions. Moreover, individual components of different ionic electrolyte, MCC and GNG precursor compounds can work synergistically in the human body, particularly because transport across cellular membranes is carrier (i.e., transport protein) mediated. For instance, in oral rehydration of a patient or athlete, the intestinal wall presents a diffusion barrier to the movement (flux) of metabolites, electrolytes and water from intestinal lumen into the blood. However, some carriers are "symporters," or "cotransporters" meaning that two substrates are required for transport. Importantly, for rehydration of the ill, injured or depleted athlete, we know that the intestinal carriers for glucose and lactate are "sodium-mediated." Hence, by providing sodium ion from NaCl or Na-Lactate, the uptake of both lactate anions and glucose molecules are increased (facilitated). Importantly, while the movement of water through its "Aquaporin" carrier is not ionically mediated, the movement of water follows the movement of other solutes such as sodium cations, lactate anions and glucose molecules down concentration gradients. Simply rephrased, the intestinal transport and uptake of more energy solutes brings more electrolytes and more water into the blood of the dehydrated, energy- and electrolyte-depleted patient, athlete or other individual.

Competition for Metabolite Uptake: Another distinct advantage of using combinations of ionic electrolyte, MCC and GNG precursor compounds to support the ill and injured as well as healthy individuals under exercise or thermal stresses is that the specific intestinal and other cell membrane transport systems is that while the individual carrier-mediated transport systems obey Michaelis-Menten kinetics and are substrate concentration sensitive and saturable, the carriers do not compete against each other. By way of example, adding more solute to a solution increases transport only up to the point where individual transporters can no longer interact with and accommodate transport of additional molecules. For instance, intestinal glucose uptake appears to saturate when presented with a glucose solution of 6% (w/v) (Jeukendrup, Moseley et al. 2006). Hence, in an attempt to move more solute, presenting the intestine with an 8-10% glucose solution will be of no practical advantage, and may give rise to bloating and other gastro-intestinal (GI) discomforts. In contrast, if a solution of lesser glucose concentration (e.g., 4-6% glucose) is augmented with 2% fructose and 2% arginyl-lactate, then significantly more rapid and greater total intestinal solute absorption and oxidation occurs (Azevedo, Tietz et al. 2007). Part of the way in which the addition of multiple sugars and carbohydrates to sports beverages can be credited to the complex and special ways in which the intestinal absorption of sugars interacts with hepatic metabolism. For example, the sweet sugar fructose can be used to enhance palatability of a beverage as well as enhance CHO energy delivery to working muscle through the systemic circulation all the while arterial blood [fructose] is held very low through intervention of the liver. Fructose taken up in the small intestine enters the portal circulation that perfuses the liver; the liver removes fructose and converts it to glucose and lactate for release into the systemic circulation. Thus, the addition of fructose to a fluid-electrolyte-energy beverage (i.e., "sports drink" or enteral resuscitation solution) bypasses the restricting effects of intestinal glucose and lactate transporters on energy solute uptake and affects delayed releases of glucose and lactate into the systemic circulation (Lecoultre, Benoit et al. 2010).

Complementary Functioning of Solutes in Solution: The actions of cations, lactate and acetate anions, GNG precursors and MCCs as efficacious for providing nutritive, electrolyte and fluid support to the ill and injured as well as healthy individuals such as athletes engaged in strenuous physical exercise or under thermal stresses have been described. As well, lactate anions, GNG precursors and some MCCs are efficacious for supporting blood glucose concentration (euglycemia) in these classes of individuals. Moreover, we have described how formulations containing single components, or combinations of components, may be efficacious for supporting nutrient, electrolyte, fluid support to those classes of individuals.

Multiple Carbohydrate Energy forms Deliver More Energy: Studies on athletes show that aqueous solutions containing 6% glucose (w/v) can deliver approximately 1 g/min (≈4 kcal) min (Jeukendrup, Moseley et al. 2006). However, by taking advantage of multiple intestinal solute transport systems, including lactate, glucose and fructose transport systems, energy substrates can be delivered more rapidly into the blood of an active person (Azevedo, Tietz et al. 2007, Lecoultre, Benoit et al. 2010) such that significantly more energy is provided to the active person using multiple, compared to single carbohydrate delivery beverages (Jeukendrup, Moseley et al. 2006).

Electrolytes in Maintaining Plasma Osmolarity and Nutritional Status: To support fluid and electrolyte balance in above identified individuals cations as found in blood plasma of healthy individuals ($Na^+$, $K^+$, $Ca^{++}$, $Mg^{++}$), along with phosphate anion, or anions [phosphate ($PO_4^{3-}$), hydrogen phosphate ($HPO_4^{2-}$) and dihydrogen phosphate ($H_2PO_4^-$)], in the ratios as they are present in the plasma of healthy individuals can be given orally, enterally or intravascularly (iv). A fluid to be given iv, $Na^+$, $K^+$, $Ca^{++}$, $Mg^{++}$, along with the phosphate anion (or anions) would be given in the ratios and amounts of 145, 4, 2.5, 1.5, and 1.0 milliequivalents per liter (mEq/l). As an electrolyte solution, cations would be delivered as chloride salts in which chloride ($Cl^-$) would be the counter ion (i.e., the anion). As an amendment of oral hydration and nutrient fluids containing energy-containing constituents such as glucose, fructose, maltodextrins as well as essential and non-essential amino acids the cation ratios of 145:4:2.5:1.5 would be maintained but diluted 6 or more times by the addition of water and other solutes (e.g., glucose, fructose and maltodextrins, essential and non-essential amino acids) such that the $Na^+$ content would approximate 20-40 mEq/l and other cations proportionately less.

Electrolytes as carriers of lactate and acetate anions, gluconeogenic (GNG) precursors and monocarboxylate compounds (MCC): In addition to providing hydration and electrolyte replacement to the ill and injured as well as individuals stressed by exercise or heat exposure the cations $Na^+$, $K^+$, $Ca^{++}$, and $Mg^{++}$ can be used as monocarboxylate compound (MCC) and gluconeogenic (GNG) precursor carriers. Again, to be consistent with the electrolyte composition in plasma of healthy individuals and to carry MCCs and GNG precursors such as lactate, $Na^+$, $K^+$, $Ca^{++}$, and $Mg^{++}$-lactate would be combined in an aqueous solution in the ratios and amounts of 145, 4, 2.5, and 1.5 along with 1 unit phosphate. Specifically, the formulary would consist of: 145 mM Na-lactate, 4 mM K-lactate, 2.5 mM Ca-lactate, and 1.5 mM $Mg^{++}$-lactate, plus 1 mEq/L Na-phosphate. Thus enabling the blending of an efficacious formulation of two or more inorganic lactate salts for delivery of carbohydrate energy in the form of lactate.

Ketones as Energy Substrates: By analogy, a formulary consistent with plasma of healthy individuals would consist of other monocarboxylates such as the biologically active ketones pyruvate, acetoacetate, beta-hydroxy butyrate (BOHB) [technically not a ketone, but rather a "ketone body" derived from the ketone acetoacetate], in the ratios, but not concentrations by molarity of 145 mM Na—BOHB, 4 mM K—BOHB, 2.5 mM Ca— BOHB, and 1.5 mM Mg—BOHB, and similarly for acetoacetate and pyruvate where the inorganic cations $Na^+$, $K^+$, $Ca^{++}$, and $Mg^{++}$ are used as carriers for GNG precursors [lactate, pyruvate and alanine (Ala), and other monocarboxylates such as the biologically active ketones acetoacetate and beta-hydroxy butyrate (BOHB). A Ketone Clamp using a targeted ketone concentration in biological samples, such as blood, urine, breath, sweat, cerebral spinal fluid, tears, etc., alone or in combination with other analytes such as lactate, glucose, or other physiological markers is conceived in the invention.

Basic Amino Acids Can Form Organic Lactate and Acetate Salts and function as Lactate and Acetate Anion Carriers: In addition to using arginine (Arg) as a lactate anion or other MCC or GNG precursor carrier, two other basic amino acids, lysine (Lys), and histidine (His) have basic properties similar to Arg because of nitrogen containing side chains. Like Arg, their pKa's are high enough that they gain a positive charge at neutral or alkaline pH. Also like Arginine ($Arg^+$), Lysine (Lys+), and Histidine ($His^+$) can bind a lactate anion that carries a negative charge at neutral or alkaline pH. Hence, like Arginine, Lys and His can be used to transport lactate and acetate anions as well as other MCCs and GNG precursors for delivery orally, enterally or parenterally, examples being Arg-lactate, Lys-lactate and His-lactate, and Arg-acetate, Lys-acetate and His-acetate. Moreover, in addition to functioning as an MCC or GNG precursor carrier, arginine can be degraded to NO, a vasodilator that helps blood flow in reaching area of high metabolic rates.

Amino Acids as Gluconeogenic Precursors: A glucogenic (gluconeogenic) amino acid is an amino acid that can be converted into glucose through gluconeogenesis. This is in contrast to the ketogenic amino acids, which are converted into ketone bodies and are then oxidized as fuel energy sources. In humans glucogenic amino acids are: Glycine (Gly), Serine (Ser), Valine (Val), Histidine (His), Arginine (Arg), Cysteine (Cys), Proline (Pro), Alanine (Ala), Glutamate (Glu), Glutamine (Gln), Aspartate (Asp), Asparagine (Asn) and Methionine (Met). As such, amendments of gluconeogenic amino acids to formulations can be used to support euglycemia in the ill and injured as well as healthy individuals such as athletes engaged in strenuous physical exercise. Compared to administering glucose (dextrose) enterally or parenterally, providing formulations containing glucogenic amino acids are less likely to provoke a sudden, sharp rise in blood glucose concentration and an ensuing insulin, counter-regulatory response that engages health care professionals in a Merry-Go-Round chase to stabilize blood glucose concentration by alternate and imprecise administrations of dextrose followed by insulin followed by dextrose, and so on.

Dual or Multiple Roles of Ketogenic Amino Acids—Lactate Anion Carriers and Fuel Sources. Humans are incapable of converting Leucine (Leu) and Lysine (Lys) to glucose, but these two basic amino acids fulfill other essential structural roles as they can be catabolized and used as fuel energy sources. Hence, when used as lactate anion carriers, Arginine, Lysine, and Histidine fulfill dual roles as lactate carriers and energy substrates. As well, these amino acids also possess other important properties; for instance, arginine is a precursor for the synthesis of NO, a powerful vasodilator. Hence, in Arginyl-Lactate Arginine is a lactate carrier, a gluconeogenic precursor, and a vasodilator. As such, a multiple role of Clamp therapy exists that includes at least two functions including nutrition therapy (i.e., energy, calorie) and signaling therapy (i.e., inflammasome through GPR81 for anti-inflammatory response).

Amino Acids that are Both Glucogenic and Ketogenic: The amino acids Isoleucine (Ile), Threonine (Thr), Phenylalanine (Phe), Tyrosine (Tyr), and Tryptophan (Trp) can gain access to both pathways of gluconeogenesis to produce glucose and be converted to ketone bodies for use as energy sources. Inclusion of these dual role (glucogenic and ketogenic) amino acids in formulations for administration orally, enterally or parentally have potential to support diverse anabolic (anaplerotic and energy substrate) functions in the ill and injured as well as in healthy individuals under stress.

Leucine and other Branched Chain Amino Acids Isoleucine (Ile) and Valine (Val): Supplementation with branched chain amino acids are anabolic and, therefore, efficacious in trauma such as burn injuries (Wolfe & Spitzer 1977, Slone 2004). Similarly, leucine supports anabolism in individuals recovering from exercise (Phillips 2012). However, while amino acids and proteins are generally considered to be poor fuels for muscular exercise in humans (Brooks, Fahey et al. 2019), leucine is oxidized as a fuel energy source during exercise (White and Brooks 1981, Millward, Davies et al. 1982). Hence, inclusion of branched-chain amino acids, particularly leucine in formulations to stimulate recovery from illnesses, injuries and exercise is efficacious.

Anaplerotic Compounds: Anaplerotic reactions are those that form intermediates of a metabolic pathway. Examples of such are found in the Tricarboxylic Acid Cycle (TCA, Krebs or Citric Acid Cycle, or “final common pathway” in the catabolism of carbohydrates, fatty acids [lipids] and amino acids). An example of a TCA Cycle compound is the first component of the final common pathway, citrate (or citric acid). Another example of an anaplerotic compound is the TCA Cycle intermediate succinate that donates electrons to Complex 2 of the mitochondrial electron transport chain (ETC). In normal function of the TCA Cycle intermediates are lost for purposes of biosynthesis (in what are called cataplerotic reactions). Unless catabolic losses of TCA intermediates replenished by anaplerotic admixture of TCA Cycle intermediates, this central hub pathway of intermediary metabolism will be depleted and hampered in fulfilling its role in connecting energy substrate flux to mitochondrial respiration. Examples of amino acids that support anaplerotic reactions are glutamate (Glu) and glutamine (Gln) that give rise to the important TCA Cycle Intermediate alpha-ketoglutarate. As such, the amino acids glutamate and glutamine are anabolic substances providing both energy, via anaplerosis to the TCA Cycle (Chance and Williams 1955, Brooks, Hittelman et al. 1971), and building blocks for protein supplements. Another example of an anaplerotic compound is malate (aka, malic acid), an important TCA Cycle intermediate and component of the “malate-aspartate shuttle” key to shuttling into mitochondria reducing equivalents produced in the cytosol during glycolysis and other metabolic pathways. The important role of malate in supporting intermediary metabolism is to facilitate respiration of pyruvate, lactate and glutamate in mitochondria (Brooks, Hittelman et al. 1971, Brooks, Dubouchaud et al. 1999). Moreover, malic and citric acids can be used to regulate the pH of aqueous formulations. Still another example of an anaplerotic compound is succinate that, in addition to making up for cataplerotic TCA Cycle losses, also facilitates functioning of the ETC as described above. For this reason, inclusion of anaplerotic compounds such as malate, citrate and succinate in formulations intended for enteral or parental administration have potential to support diverse anaplerotic and anabolic and energy substrate functions in the ill and injured as well as in healthy individuals under stress.

Glycerol as Lactate and Acetate Anion Carriers: Through enzymatic or chemical reactions the three hydroxyl groups of glycerol are available for esterification with lactate and acetate anions to form glycerol tri-lactate (GTL), glycerol di-lactate, glycerol mono-lactate, and glycerol tri-acetate (acetin, GTA), as well as glycerol di- and mono-acetates, respectively. Moreover, when potential glycerol ester bonds are unfiled, there is opportunity for glycerol to carry more than one moiety, such as is the case with lactic acid esters of mono or diglyceride that carries one or two lactate anions and one or two palmitate anions. In this regard it is appropriate to note that sodium lactate, acetin and lactic acid esters of mono or diglycerides are all on the GRAS list. Ester bonds are rapidly broken by esterases in the gastrointestinal tract, blood, and cells to yield glycerol, lactate, acetate and palmitate anions. Glycerol is highly miscible in water and is efficacious as a hydrating moiety (van Rosendal, Osborne et al. 2010) as well as a gluconeogenic (energy delivery) precursor (Trimmer, Casazza et al. 2001). As already identified, lactate anion is a fuel energy source (Brooks, Butterfield et al. 1991, Bergman, Wolfel et al. 1999), and gluconeogenic precursor (Bergman, Horning et al. 2000, Emhoff, Messonnier et al. 2013). In contrast, while not a gluconeogenic precursor, providing acetate helps support euglycemia because acetate is a fuel energy source, and therefore spares use of glucose as a fuel energy source. Hence, all components of GTL and GTA are efficacious for purposes of hydration and providing fuel sources and a supporting blood glucose homeostasis using metabolic pathways intact in the critically ill and injured as well as healthy individuals.

Functional groups A are readily transported from the intestine into the systemic blood circulation by independent transport mechanisms and subsequently moved around the body via the systemic circulation.

Efficacy of Glycerol in addition providing the carrier backbone for metabolite transport. Muscle glycerol turnover increases with exercise (Wallis, Friedlander et al. 2007). In addition, glycerol released from working muscle and adipose during whole-body exercise is a gluconeogenic precursor (Bergman, Butterfield et al. 1999, Bergman, Horning et al. 2000, Wallis, Friedlander et al. 2007) (Trimmer, Casazza et al. 2001). Hence, glycerol is part of the metabolic response to exercise. Moreover, glycerol, administered prior to exercise can result in “hyperhydration” of an athlete, thus promoting endurance during exercise in hot and humid environments (van Rosendal, Osborne et al. 2010). Therefore, as part of the metabolic response to exercise, a gluconeogenic precursor, and a molecule to maintain plasma volume, beyond its role as a metabolite carrier, by itself glycerol is efficacious as part of a solution to support metabolism and physiology in physiologically stressed individuals.

Gels—An alternative to using aqueous solutions, gels can also be used to deliver salts and energy providing compounds. A lactic acid ester of mono or diglyceride can enable the formation of a gel-like structure due to the alpha-crystalline property of the compound to absorb water in the solid state. Hence the emulsification of the lactate ester of mono or diglyceride would enable the delivery of lactate, ketones, proteins, and other salt carriers of metabolic and signaling molecules in a gel form.

Inventor's Research Support for Compounds and Formulations

Health and wellness with novel chemical structures can be indicated for use for the acute and chronic injured and ill such as during traumatic brain injury or diabetes. For example, a chemical entity that provides short- and longer-term carbohydrate energy without the use of insulin to signal cellular uptake would be advantageous. The new chemical entities described herein offer such health and wellness beneficial outcome measures.

This invention relates to a novel group of chemical entities and formulations in the form of carbohydrate, amino acid, fatty acids and ketone bodies to maximize short-, medium- and long-term fuel delivery and endurance exercise for the application of sports and other nutrition in healthy, ill and injured humans and other mammals.

New chemical entities to deliver lactate, ketones, fatty acids and other molecules from a single tri-ester molecule. Use of the glycerol backbone to form a mono-, di- or tri-esters of a combination of lactate and ketones will deliver energy in the form of lactate, ketones and glycerol simultaneously. For example, a new chemical entity with a single glycerol bound to a single molecule of lactate and a single molecule of beta hydroxy butyrate would yield a single lactate molecule, a single beta hydroxybutyrate molecule and a single glycerol molecule when ingested as nutritional energy. Another example of a new chemical entity with a single glycerol bound to a single molecule of beta hydroxy butyrate and two molecules of lactate would yield two molecules of lactate, one molecule of beta hydroxy butyrate and one molecule of glycerol in the form of nutritional energy. Likewise, a tri-ester of glycerol molecule bound with two beta hydroxy butyrate molecules and one lactate molecule would yield nutritional energy in the form of one lactate, one glycerol and two beta hydroxy butyrate molecules. Other combinations of the tri-ester could include molecules of pyruvate, acetate, acetoacetate and fatty acids.

Other glycerol esters of lactate and fatty acids would include the use of short chain, medium chain and even and odd numbered fatty acids. An example of such a unique molecule that would deliver both carbohydrate energy in the form of lactate and lipid energy in the form of fatty acid and glycerol would be two lactate anions plus heptanoic acid with a glycerol carrier. The medium, seven carbon, odd chain fatty acid, heptanoic acid acts as an anaplerotic substrate. Triheptanoin has been used in clinical trials for the treatment of inherited metabolic diseases. This invention anticipates combinations of multiple functions of lactate and combinations of fatty acids (e.g., heptanoate, palmitate, stearate, oleate) with a carrier such as glycerol such as in this example.

Efficacy of new chemical entities containing carbohydrates, ketone bodies, lipids and protein, in addition to carrying fuel energy to tissues throughout the body, also include signaling properties. For example, a single molecule as well as a formulation containing a lactate and beta hydroxybutyrate molecule would act as two distinct ligands to single membrane proteins such as GPR81/HCAR1 via lactate and GPR109 a and b via beta hydroxybutyrate.

Formulations and new chemical entities are concocted to individualize and optimize nutrient delivery to improve body energy state (BES) and achieve exquisite glucose control (EGC) is to deliver multiple nutrients and other amendments, thereby utilizing different, but complementary parallel non-competitive pathways of energy transduction for ill, injured or stressed individuals such as athletes FIGS. 1-21. Example (1) fueling an athlete: BES of an energy depleted athlete can be supported by supplying multiple metabolites that are absorbed via non-competitive transporters in the GI tract, penetrate muscle and other cell plasma membranes by multiple, non-competitive transport proteins, and enter pathways of cellular energy production by various routes. This novel approach is distinct, for instance from simply adding more of one fuel energy source (e.g., the hexose sugar glucose) to an oral solution. Such single component solutions (e.g., glucose a 6%, w/vol) will saturate intestinal transporters, bog down absorption, and result in GI distress. Alternatively, a distributed approach would entail delivering a solution containing 2% glucose, 2% lactate compound, and 2% fructose. Example (2) fueling a diabetic: by taking advantage of insulin-independent pathways of energy transduction fueling a diabetic person at rest or during exercise using glucose would be counterproductive. Instead, a solution containing a mixture of non-glucose metabolites such as 2% lactate, 2% octanoate, 2% acetoacetate or beta-hydroxybutyrate, 1% leucine and 1% fructose would be rapidly cleared from the GI tract because of absorption via specific non-competitive transporters, distributed via the systemic circulation and cleared by diverse tissues all by insulin-independent and non-competitive pathways. The following recitation each MCC, GNG precursor consists of two parts: (a) the solute (e.g., lactate), and (b) an inorganic (e.g.,) $Na^+$ ion or organic carrier (e.g., arginine or glycerol), the MCC, GNG precursors being sodium-lactate, arginyl-lactate and glycerol tri-lactate, respectively. To reiterate though similar in delivery of lactate anion, the individual carriers (i.e., $Na^+$, arginine and glycerol) have different metabolic and physiological purposes. More specifically, sodium ion is necessary for transport of some solutes across membrane barriers (e.g., symporters) and electrolyte replacement during and after fluid loss as in sweating and other forms of dehydration, arginine is a vasodilator stimulating blood flow to metabolically active tissues, and glycerol supports maintenance of blood volume during dehydration.

Thus the invention provides new chemical compound entities to provide fuel energy and signaling properties, including new chemical entities using glycerol as a backbone carrier to provide MMC and GNG precursor, ketone body, fatty acid and signaling properties. Carrier anions to provide fuel energy and signaling properties esterified to glycerol backbone are also disclosed. The following are also disclosed:

New chemical entities using a glycerol backbone provide advantages by minimizing salt carriers associated with individual molecules. For example, a sodium lactate and a sodium beta hydroxybutyrate add two sodium molecules. A new chemical entity wherein a lactate and beta hydroxybutyrate are esterified to a glycerol eliminates all sodium and provides multiple energy and signaling molecules when hydrolyzed in the gut.

New chemical entities providing carbohydrate and ketone body energy in a single molecule such as Glycerol 1 Mono Beta D Hydroxybutyrate 3 Mono L-(+)-Lactate including at least one lactate, and one beta hydroxy butyrate esterified to glycerol in a single molecule uniquely provide short-, medium- and long-term energy requirements to healthy resting, exercising or ill and injured patients.

New chemical entities providing carbohydrate and ketone body energy in a single molecule such as Glycerol 1 Mono Beta D Hydroxybutyrate 3 Mono Pyruvate including at least one pyruvate, and one beta hydroxy butyrate esterified to glycerol in a single molecule uniquely provide short-, medium- and long-term energy requirements to healthy resting, exercising or ill and injured patients.

New chemical entities providing carbohydrate and ketone body energy in a single molecule such as Glycerol 1 Mono Beta D Hydroxybutyrate 2, 3 Di-L-(+)-Lactate, Glycerol 1, 3 Di Beta D Hydroxybutyrate 2 Mono L-(+)-Lactate and provide two ketone body in the form of BHOH and one lactate in a single molecule. Examples such as Glycerol 1, 2, 3 Tri Beta D Hydroxybutyrate provide three ketone bodies in the form of beta hydroxybutyrate, Glycerol 1 Mono-L-(+)-Lactate 3 Mono Acetoacetate provide one lactate and one beta hydroxy butyrate esterified to glycerol in a single molecule. The chemical entity includes this chemical structure and other possible structures with different stereoisomers and positions.

A chemical entity Glycerol 1 Mono Pyruvate 3 Mono Acetoacetate including: one pyruvate and one acetoacetate esterified to glycerol in a single molecule A chemical entity, Glycerol 1 Mono-L-(+)-Lactate 2 Mono Acetoacetate 3 Mono Beta Hydroxybutyrate including: one lactate, and one acetoacetate, and one beta hydroxy butyrate esterified to glycerol in a single molecule.

A chemical entity, Glycerol 1 Mono Pyruvate 2 Mono Acetoacetate 3 Mono Beta Hydroxybutyrate including: one pyruvate, and one acetoacetate, and one beta hydroxy butyrate esterified to glycerol in a single molecule.

A chemical entity, Glycerol 1 Mono-L-(+)-Lactate 3 Mono Palmitate including: one lactate and one long chain fatty acid esterified to glycerol in a single molecule. The chemical entity includes the following chemical structure and other possible structures with different stereoisomers and positions.

A chemical entity, Glycerol 1 Mono Pyruvate 3 Mono Palmitate including: one pyruvate and one long chain fatty acid esterified to glycerol in a single molecule. The chemical entity includes the following chemical structure and other possible structures with different stereoisomers and positions.

A chemical entity, Glycerol 1 Mono-L-(+)-Lactate 3 Mono Octanoate including: one lactate and one medium chain fatty acid esterified to glycerol in a single molecule. The chemical entity includes the following chemical structure and other possible structures with different stereoisomers and positions.

A chemical entity, Glycerol 1 Pyruvate 3 Mono Octanoate including: one pyruvate and one medium chain fatty acid esterified to glycerol in a single molecule. The chemical entity includes the following chemical structure and other possible structures with different stereoisomers and positions.

A chemical entity, Glycerol 1 Mono-L-(+)-Lactate 3 Mono Acetate including: one pyruvate and one short chain fatty acid esterified to glycerol in a single molecule. The chemical entity includes the following chemical structure and other possible structures with different stereoisomers and positions.

A chemical entity, Glycerol 1 Pyruvate 3 Mono Acetate including: one pyruvate and one short chain fatty acid esterified to glycerol in a single molecule. The chemical entity includes the following chemical structure and other possible structures with different stereoisomers and positions.

A chemical entity, Glycerol 1 beta hydroxybutyrate 3 palmitate including: one beta hydroxybutyrate and one long chain fatty acid esterified to glycerol in a single molecule. The chemical entity includes the following chemical structure and other possible structures with different stereoisomers and positions.

A chemical entity, Glycerol 1 acetoacetate 3 palmitate including: one acetoacetate and one long chain fatty acid esterified to glycerol in a single molecule. The chemical entity includes the following chemical structure and other possible structures with different stereoisomers and positions.

A chemical entity, Glycerol 1 beta hydroxybutyrate 3 octanoate including: one beta hydroxybutyrate and one medium chain fatty acid esterified to glycerol in a single molecule. The chemical entity includes the following chemical structure and other possible structures with different stereoisomers and positions.

A chemical entity, Glycerol 1 acetoacetate 3 octanoate including: one acetoacetate and one medium chain fatty acid esterified to glycerol in a single molecule. The chemical entity includes the following chemical structure and other possible structures with different stereoisomers and positions.

A chemical entity, Glycerol 1 beta hydroxybutyrate 3 Acetate including: one beta hydroxybutyrate and one short chain fatty acid esterified to glycerol in a single molecule. The chemical entity includes the following chemical structure and other possible structures with different stereoisomers and positions.

A chemical entity, Glycerol 1 acetoacetate 3 Acetate including: one acetoacetate and one short chain fatty acid esterified to glycerol in a single molecule. The chemical entity includes the following chemical structure and other possible structures with different stereoisomers and positions.

A chemical entity, Glycerol 1 Mono-L-(+)-Lactate, 2 Mono Palmitate 3 Mono beta hydroxy butyrate including: one lactate, and one long chain fatty acid, and one beta hydroxy butyrate esterified to glycerol in a single molecule. The chemical entity includes the following chemical structure and other possible structures with different stereoisomers and positions.

A chemical entity, Glycerol 1 Pyruvate, 2 Mono Palmitate 3 Mono beta hydroxy butyrate including: one pyruvate, and one long chain fatty acid, and one beta hydroxy butyrate esterified to glycerol in a single molecule. The chemical entity includes the following chemical structure and other possible structures with different stereoisomers and positions.

A chemical entity, Glycerol 1 L-(+)-Lactate, 2 Mono Octanoate, 3 Mono beta hydroxy butyrate including: one lactate, and one medium chain fatty acid, and one beta hydroxy butyrate esterified to glycerol in a single molecule. The chemical entity includes the following chemical structure and other possible structures with different stereoisomers and positions.

A chemical entity, Glycerol 1 Pyruvate, 2 Mono Octanoate, 3 Mono beta hydroxy butyrate including: one pyruvate, and one medium chain fatty acid, and one beta hydroxy butyrate esterified to glycerol in a single molecule. The chemical entity includes the following chemical structure and other possible structures with different stereoisomers and positions.

A chemical entity, Glycerol 1 L-(+)-Lactate, 2 Mono Acetate, 3 Mono beta hydroxy butyrate including: one lactate, and one short chain fatty acid, and one beta hydroxy butyrate esterified to glycerol in a single molecule. The chemical entity includes the following chemical structure and other possible structures with different stereoisomers and positions.

A chemical entity, Glycerol 1 Pyruvate, 2 Mono Acetate, 3 Mono beta hydroxy butyrate including: one pyruvate, and one short chain fatty acid, and one beta hydroxy butyrate esterified to glycerol in a single molecule. The chemical entity includes the following chemical structure and other possible structures with different stereoisomers and positions.

A chemical entity, Glycerol 1 L-(+)-Lactate, 3 Mono Acetoacetate including: one lactate, and one acetoacetate esterified to glycerol in a single molecule. The chemical entity includes the following chemical structure and other possible structures with different stereoisomers and positions.

A chemical entity, Glycerol 1 Pyruvate, 3 Mono Acetoacetate including: one pyruvate, and one acetoacetate esterified to glycerol in a single molecule. The chemical entity includes the following chemical structure and other possible structures with different stereoisomers and positions.

A chemical entity, Glycerol 1 L-(+)-Lactate, 2 Mono Palmitate, 3 Mono Acetoacetate including: one lactate, and one long chain fatty acid, and one acetoacetate esterified to glycerol in a single molecule. The chemical entity includes the following chemical structure and other possible structures with different stereoisomers and positions.

A chemical entity, Glycerol Di-L-(+)-Lactate Mono Octanoate including: two lactate, and one medium chain fatty acid esterified to glycerol in a single molecule. The chemical entity includes the following chemical structure and other possible structures with different stereoisomers and positions.

A chemical entity, Glycerol Mono-L-(+)-Lactate Di Octanoate including: one lactate, and two medium chain fatty acid esterified to glycerol in a single molecule. The chemical entity includes the following chemical structure and other possible structures with different stereoisomers and positions.

A chemical entity, Glycerol 1 Pyruvate, 2 Mono Palmitate, 3 Mono Acetoacetate including: one lactate, and one long chain fatty acid, and one acetoacetate esterified to glycerol in a single molecule. The chemical entity includes the following chemical structure and other possible structures with different stereoisomers and positions.

A chemical entity, Glycerol 1 L-(+)-Lactate, 2 Mono Octanoate, 3 Mono Acetoacetate including: one lactate, and one medium chain fatty acid, and one acetoacetate esterified to glycerol in a single molecule. The chemical entity includes the following chemical structure and other possible structures with different stereoisomers and positions.

A chemical entity, Glycerol 1 Pyruvate, 2 Mono Octanoate, 3 Mono Acetoacetate including: one lactate, and one medium chain fatty acid, and one acetoacetate esterified to glycerol in a single molecule. The chemical entity includes the following chemical structure and other possible structures with different stereoisomers and positions.

A chemical entity, Glycerol 1,2 Di-Acetate, 3 Mono Palmitate including: two acetate, and one long chain fatty acid esterified to glycerol in a single molecule. The chemical entity includes the following chemical structure and other possible structures with different stereoisomers and positions.

A chemical entity, Glycerol 2 Mono-Acetate, 1, 3 Di Palmitate including: one acetate, and two long chain fatty acid esterified to glycerol in a single molecule. The chemical entity includes the following chemical structure and other possible structures with different stereoisomers and positions.

A chemical entity, Glycerol 1, 2 Di-Acetate, 3 Mono-L-(+)-Lactate including: two acetate, and one lactate esterified to glycerol in a single molecule. The chemical entity includes the following chemical structure and other possible structures with different stereoisomers and positions.

A chemical entity, Glycerol 2 Mono-Acetate, 1,3 Di-L-(+)-Lactate including: one acetate, and two lactate esterified to glycerol in a single molecule. The chemical entity includes the following chemical structure and other possible structures with different stereoisomers and positions.

A chemical entity, Glycerol 1 L-(+)-Lactate, 2 Mono Acetate, 3 Mono Acetoacetate including: one lactate, and one short chain fatty acid, and one acetoacetate esterified to glycerol in a single molecule. The chemical entity includes the following chemical structure and other possible structures with different stereoisomers and positions.

A chemical entity, Glycerol 1 Pyruvate, 2 Mono Acetate, 3 Mono Acetoacetate including: one pyruvate, and one short chain fatty acid, and one acetoacetate esterified to glycerol in a single molecule. The chemical entity includes the following chemical structure and other possible structures with different stereoisomers and positions.

A chemical entity, Glycerol 1 Mono-D-Beta-Hydroxybutyrate, 2,3 Di-Acetoacetate including: one Beta-Hydroxybutyrate, and two acetoacetate esterified to glycerol in a single molecule. The chemical entity includes the following chemical structure and other possible structures with different stereoisomers and positions.

A chemical entity, Glycerol 1,3 Di-D-Beta-Hydroxybutyrate, 2 Mono-Acetoacetate including: two Beta-Hydroxybutyrate, and one acetoacetate esterified to glycerol in a single molecule. The chemical entity includes the following chemical structure and other possible structures with different stereoisomers and positions.

A chemical entity, Glycerol 1,3 Di-Acetoacetate, 2 Mono-Palmitate including: two acetoacetate and one long chain fatty acid esterified to glycerol in a single molecule. The chemical entity includes the following chemical structure and other possible structures with different stereoisomers and positions.

A chemical entity, Glycerol 3 Mono-Acetoacetate, 1,2 Di-Palmitate including: one acetoacetate and two long chain fatty acid esterified to glycerol in a single molecule. The chemical entity includes the following chemical structure and other possible structures with different stereoisomers and positions.

A chemical entity, Glycerol 1, 3 Di-Acetoacetate, 2 Mono-L(+)-Lactate including: two acetoacetate and one lactate esterified to glycerol in a single molecule. The chemical entity includes the following chemical structure and other possible structures with different stereoisomers and positions.

A chemical entity, Glycerol 1 Mono-Acetoacetate, 2,3 Di-L(+)-Lactate including: one acetoacetate and two lactate esterified to glycerol in a single molecule. The chemical entity includes the following chemical structure and other possible structures with different stereoisomers and positions.

A chemical entity, Glycerol 1, 3 Di-Pyruvate, including: two pyruvate esterified to glycerol in a single molecule. The chemical entity includes the following chemical structure and other possible structures with different stereoisomers and positions.

A chemical entity, Glycerol 1, 2, 3 Tri-Pyruvate, including: three pyruvate esterified to glycerol in a single molecule. The chemical entity includes the following chemical structure and other possible structures with different stereoisomers and positions.

A chemical entity, Glycerol 1 Mono-Pyruvate 2,3 Di-Palmitate, including: one pyruvate and two long chain fatty acids esterified to glycerol in a single molecule. The chemical entity includes the following chemical structure and other possible structures with different stereoisomers and positions.

A chemical entity, Glycerol 1, 3 Di-Pyruvate 2 Mono-Palmitate, including: two pyruvate and one long chain fatty acid esterified to glycerol in a single molecule. The chemical entity includes the following chemical structure and other possible structures with different stereoisomers and positions.

A chemical entity, Glutamine-Pyruvate, including: one pyruvate and one glutamine in a single molecule. The chemical entity includes the following chemical structure and other possible structures with different stereoisomers and positions.

A chemical entity, Lysine-Pyruvate, including: one pyruvate and one lysine in a single molecule. The chemical entity includes the following chemical structure and other possible structures with different stereoisomers and positions.

A chemical entity, Histidine-Pyruvate, including: one pyruvate and one histidine in a single molecule. The chemical entity includes the following chemical structure and other possible structures with different stereoisomers and positions.

A chemical entity, Arginine-Pyruvate, including: one pyruvate and one arginine in a single molecule. The chemical entity includes the following chemical structure and other possible structures with different stereoisomers and positions.

Methods for Synthesis of the Above Carrier-Anion (R-A) Compounds

Lipase enzymes such as *Candida rugosa* lipase, *Pseudomonas* sp. lipase, *Mucor miehei* lipase, and Lipase B from *Candida Antarctica* and Novozym 435 have been successfully used as catalysts for esterification of molecules that contain at least one hydroxy or acid group (Brooks, U.S. Pat. No. 6,743,821). the short chain polyalcohol glycerol contains three carbons and three hydroxyl groups and, therefore, is an appropriate structure for esterification of monocarboxylic acids ranging in carbon chain length 2 (acetate) or 3 (lactate and pyruvate), to 16 (palmitate) to glycerol. Both organic and aqueous media can be used for synthesis of glycerol-monocarboxylate esters, but aqueous media are preferred because organic solvents are inappropriate for introduction into human or other mammals. The solvents could be eliminated by liquid chromatography, but the separation stem is unnecessary if an aqueous medium is involved.

For synthesis of glycerol-monocarboxylate esters in aqueous media glycerol and short-chain monocarboxylates such as lactic, pyruvic and amino acids are readily miscible with the water. Longer chain, "fatty" acids are less miscible, but miscibility can be improved by warming (e.g., 60° C.) and shaking, or by using commercially available long-chain monoglycerides esters (e.g., glycerol-mono-palmitate) as a starting material. Esterification of lactate, pyruvate, and amino acids to glycerol can be achieved, by changing the molar ratios of constituents. For instance, if glycerol tri-lactate is intended, the ratio of lactic acid to glycerol would be (3:1). Similarly, if glycerol di-lactate mono palmitate is intended the glycerol to lactate and palmitate in incubation media would be (1:2:1). Or starting from glycerol-mono-palmitate and lactic acid the ratio would be (1:2). Moreover, ethyl lactate can be used as an alternative to lactic acid.

In a glass stopped bottle, 150 mg (1.65 mmol) of L-lactic acid, 51 mg glycerol (0.55 mmol) are mixed. Fifty mg of Novozym 435 lipase is added and the mixture gently shaken for 48-72 hr. at 40° C.; ester yield should approximate 70%. After completion, the enzyme and solvent can be eliminated by filtration, and the ester can be separated from reactants by liquid chromatography or dialysis notwithstanding that the reactants (lactate and glycerol) individually have bioavailability and viability.

Given the method of synthesis numerous derivative esters can be similarly synthesized. For example, if a 2-lactate:1-pyruvate glycerol ester is intended, the molar ratios of lactate:pyruvate:glycerol reactants would be (2:1:1) and Novozym 435 lipase serve as the catalyst. Similarly, if glycerol di-lactate mono-palmitate is intended the glycerol to lactate and palmitate in incubation media would be (1:2:1). Similarly, if glycerol mono lactate mono beta hydroxybutyrate is intended the glycerol to lactate and beta hydroxybutyrate in incubation media would be (1:1;1). Again, Novozym 435 lipase serve as the catalyst, but the incubation temperature would be raised to 60° C.

Isotopic Variations and Deuterium Enrichment

Miscibility also refers to the ability of different isotopomers of water to mix homogeneously, such as deuterium oxide ($^2H_2O$, $D_2O$ or "heavy water"), and tritium oxide ($^3H_2O$) to mix in hydrogen oxide ($^1H_2O$, $H_2O$ or commonly "water"). As well, other stable, non-radioactive isotopomers of atoms such as carbon (e.g., $^{12}C$, $^{13}C$ and $^{14}C$), oxygen (e.g., $^{16}O$, and $^{18}O$) and other isotopes mix homogeneously in formulations appropriate for human administration.

Common and Conflicting Uses of Deuterium (D): There are multiple uses of deuterium ($^2H$ or D) containing compounds in physiology. Substitution of deuterium for hydrogen in water yields "heavy water," $D_2O$. Deuterium can also be substituted for hydrogen in metabolites, making them isotope tracers to follow the metabolism of metabolites such as glucose ([6,6-$^2H$] glucose, or D2-Glucose) or glycerol ([1,1,2,3,3-$^2H$] glycerol, or D5-Glycerol). For this application isotopic enrichments of D2-Glucose and D5-Glycerol in blood plasma are tracked and metabolic flux (turnover) rate can be determined by measuring dilution of the tracer instantaneously, or over time (Brooks, Wolfel et al. 1992, Bergman, Butterfield et al. 1999, Emhoff, Messonnier et al. 2013, Glenn, Martin et al. 2014). In this process, deuterium is typically lost by enzymatic degradation of the tracer and release of deuterium as a byproduct into body water as $D_2O$. Additionally, in somewhat of a reversal, $D_2O$ added to body water can act as a tracer when there are specific enzymatic reactions in which water is a substrate, or in which products of the process of interest are in equilibrium with body water such that deuterium from $D_2O$ is incorporated into a reaction product as occurs in gluconeogenesis (Landau, Wahren et al. 1995, Landau 1999, Horning, Colberg et al. 2000, Chacko, Sunehag et al. 2008). Considering sensitivity of contemporary measuring devices, the volume of $D_2O$ needed to label metabolite pools is relatively small representing only a few tenths of a percent of total volume (Chacko, Sunehag et al. 2008). By example, the addition of 2 or 3 ml $D_2O$ to 997 or 998 mL $H_2O$ would, depending on instrument sensitivity, sufficiently label the body for detectable levels of deuterium to be detected in blood glucose produced via gluconeogenesis. Thus, energy containing formulations as described can be titrated to deliver precision energy needs to support the Body Energy State with the addition of an isotope of hydrogen (or other isotope such as carbon) to the formulation. As well, formulations containing anti-inflammatory agents such as those described herein can be used to target the inflammasome as a signaling formulation that complements the body energy state in that an additional physiological condition can be mitigated during illness and injury or in healthy individuals.

Because in one instance the addition of metabolites to be traced via intravenous injection or infusion contains deuterium (e.g., D2-Glucose or D5-Glycerol) and catabolism of the trace (molecule of interest) produces $D_2O$, whereas in another instance $D_2O$ is added to body water to isotopically label blood metabolites, the two forms of metabolite tracing using deuterium are fundamentally different, and are seldom practiced in the same person or experimental animal or other system at the same time. Miscibility of Solutions for Intravenous Administration Into Human Blood: Nominal molarity of salts administered into human blood is 150-155 mM, or 300-310 mEq/L if both anions and cations are counted. Hence, solutions given in large volumes of solutions given intravenously (iv) such as normal saline (0.9% NaCl, w/v) are formulated to 150-155 mM, or 300-310 mEq/L. Smaller volumes of more concentrated nutrient-containing formulations and saline (NaCl) solutions can be given to provide parenteral nutrition or support fluid and electrolyte balance as practiced in the treatment of hyponatremia that results in over consumption of water, renal failure or from persistent release of antidiuretic hormone (ADH). In the latter case, a concentrated (3%) NaCl solution (513 mEq/L) is given at a rate and volume to restore plasma (sodium] to a normative value of 145 mEq/L. The formulation delivered iv will be diluted in blood by endogenous solutes and water; hence, in an attempt to normalize blood electrolyte levels and provide intravenous delivery of salts and nutrients depends on several factors including disposal for fluid, electrolytes and nutrients from plasma volume. Importantly, highly concentrated solutions (≥1,000 mEq/L) can have osmotic and pH effects at the site of infusion causing damage to (crenation) of red blood cells, denaturation of blood proteins, or injury to the vessel wall (phlebitis). Hence, concentrated solutions are usually delivered with normal saline or other isosmotic solution such as 10% dextrose (w/v glucose, or D10 glucose) in $H_2O$ to dilute the concentrated infusate and reduce its osmotic and pH effects.

Miscibility of isosmotic aqueous solutions for intravenous administration into human blood: For introduction into blood of a human or other mammal via the iv route, solutions with individual osmolalities in the range of 300±10 mEq/L, such as normal saline, D10 glucose and can be given to meet body energy needs without affecting plasma osmolality. In another example around blood glucose management, normal blood [glucose] being 5 g/L, D5 glucose can be delivered [0.2 kcal/ml of crystalline glucose (200 kcal/L) and 0.17 kcal/ml (170 kcal/l)] for dextrose monohydrate], but D5 glucose is a slightly hypotonic solution (5% glucose=278 mEq/L). To normalize osmolality of D5 glucose administration, NaCl can be added to raise total osmolality to the normal range. For example, a solution with D5 glucose in half normal saline (0.45% w/v of NaCl) will have with combined osmolality≈300 mEq/L (=139+154=290), can be administered without concern for disruption of cells in blood or vessel walls.

Miscibility of isosmotic aqueous solutions for intravenous infusion into human or experimental mammal blood extends to admixture of solutions containing efficacious salts, MCCs and GNG precursors and esters containing energy functional groups such as lactate extends to the inclusion of $D_2O$ in the formulation in which the heavy water is added to measure GNG or other fractional production rates as described above.

Figure 114:
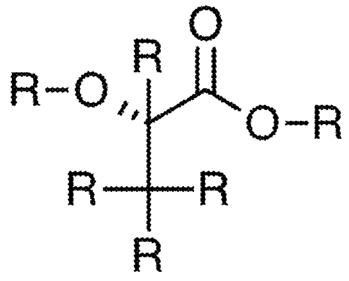
Figure 115:
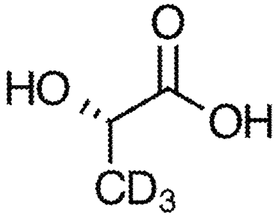
Figure 116:
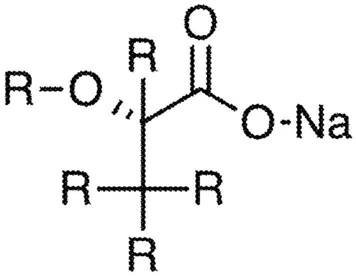
Figure 117:
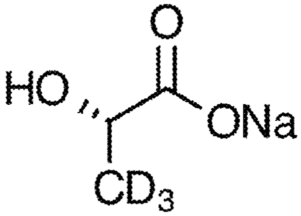
Figure 118:
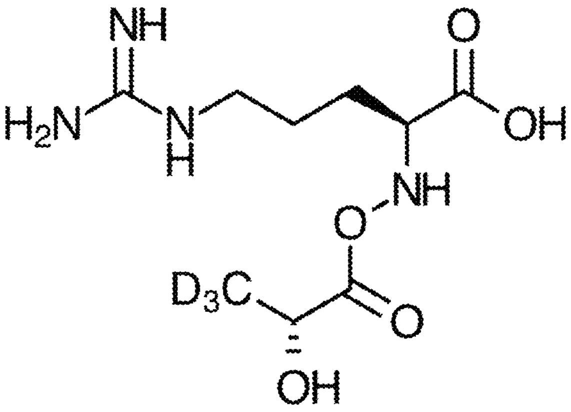
Figure 119:
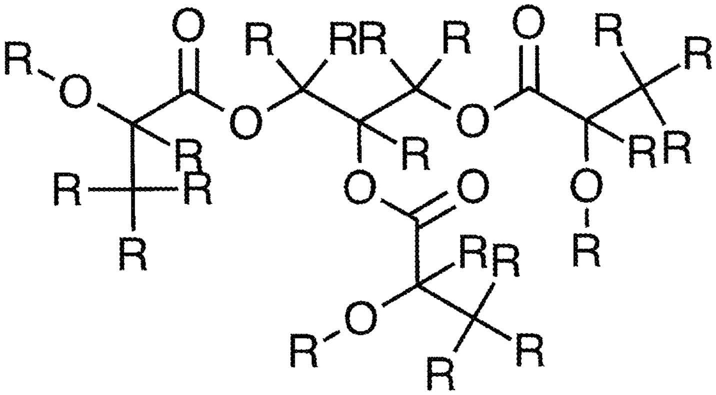
Figure 120:
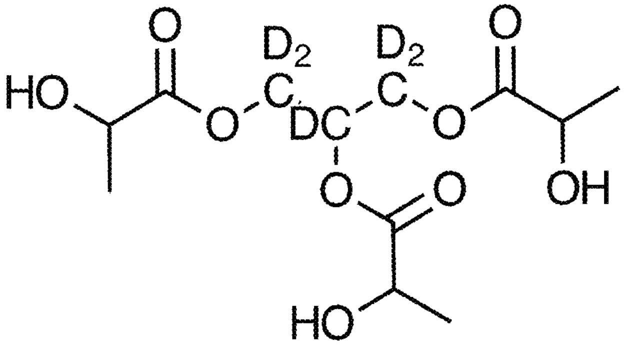
Figure 121:
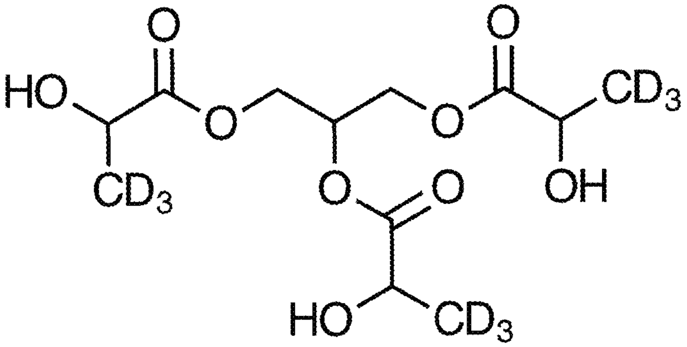
Figure 122:
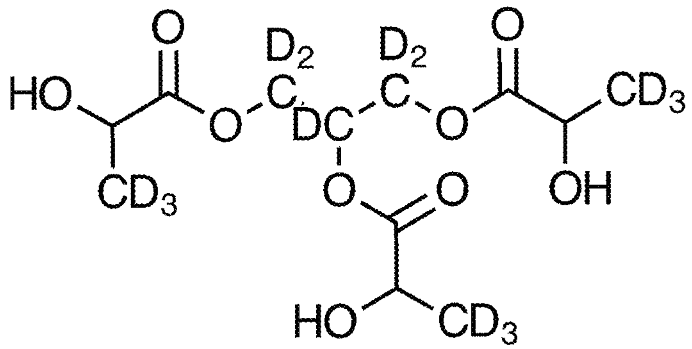
Figure 123:
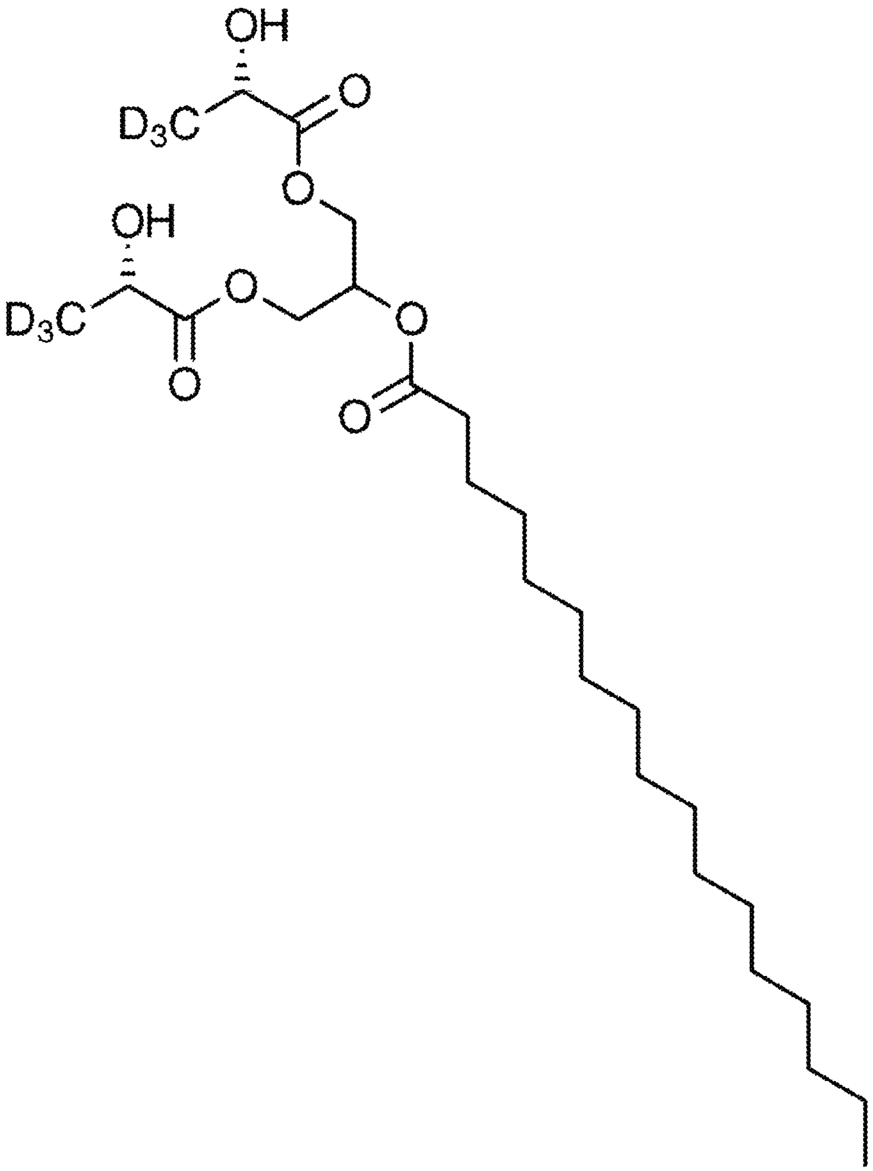
Figure 124:
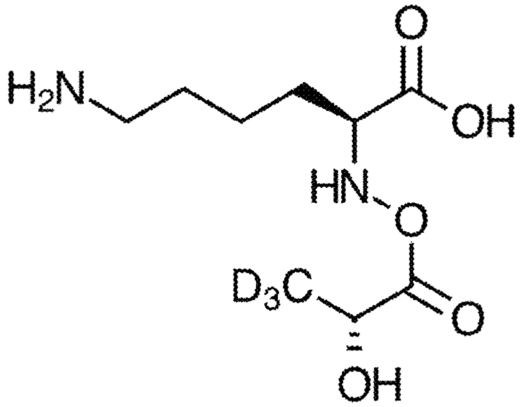

New Chemical Entities containing deuterium substitution for hydrogen to alter metabolism: Deuterium Isotopic Kinetic Effect (DKIE) between a C—H and C-D bond is significant enough to change the pharmacokinetic and pharmacodynamic properties of the molecule. Delaying or modifying the absorption of lactate due to C—H versus C-D bond can add a time-release quality to the chemical entity or formulation containing molecules with C-D substitutions. Compositions containing C—H lactate molecules, C-D lactate molecules or combinations of both can significantly alter the absorption of lactate. Some preferred embodiments of the invention utilizing deuterium enrichments are illustrated in the figures, such as FIG. 114, with deuterium generally denoted as D.

Cytoplasmic and Mitochondrial membrane facilitated lactate transport using C-D lactate or conjugates of lactate as well as use in drug compositions containing C-D lactate to alter cytoplasmic and inner and outer mitochondrial membrane transport of lactate to increase or decrease oxidation of lactate and reduction of pyruvate to lactate depending on deuterium or hydrogen to carbon bond. As well Deuterium versus Protium action on LDH, MCT, GPR81, TREK1, etc. DKIE with using exogenous C-D lactate increase DKIE and alters the absorption of lactate.

Examples of chemical entities containing C-D bonds to alter the absorption of energy include: L-(+) Lactic acid where the carbon-hydrogen bond in the molecule is either H or D, L-(+) CD3 Lactic acid, Sodium L(+) Lactate where the carbon-hydrogen bond in the molecule is either H or D (other salts of lactate are also candidates), Sodium L(+) CD3 Lactate (other salts of lactate are also candidates), L-arginyl L-(+) CD3 lactate (lactate on Zwitterion; other amino acids with basic side chains also candidates such as lysine and histidine). Glycerol Tri-L-Lactate where is the carbon-hydrogen bond in the molecule is either D or H, D5 Glycerol Tri-L-Lactate, Glycerol Tri-CD3-L-Lactate, D5 Glycerol Tri-CD3-L-Lactate, Glycerol Di-CD3-L-Lactate Mono palmitate, L-lysine L-(+) CD3 lactate, L-histidine L-(+) CD3 lactate.

The compounds described above are preferably used in aqueous formulations, in a preferred embodiment for oral ingestion for people engaged in exercise or sports performance, but also in other embodiments, including other metabolic stress, as such as injured or ill. The invention also contemplates enteral and parenteral use. Some preferred embodiments of the formulations are listed in FIGS. 1-21.

In addition to those two most important cellular energy sources, other supportive dietary carbohydrate energy sources are preferably provided in the formulations of the invention. Specifically, glucose and fructose utilize specific transporters allowing movement of those solutes from the intestine into the blood. For example, in the intestine, maltodextrin is digested to glucose and is absorbed into blood as already described. In addition, table sugar (sucrose, a di-saccharide) is digested to its components, glucose and fructose, in the intestine with absorption as already described. However, when too much glucose, fructose, maltodextrin or sucrose is ingested, the transporters become saturated and blocked leading to gastrointestinal distress, bloating and diarrhea. As well, limitation of carbohydrate absorption through the intestine due to saturated transporters results in reduced performance because energy needed by the working tissue is not delivered and therefore not available to be utilized.

On the other hand the formulations of the invention use different transporters, both at intestinal and cellular levels. These combinations of solutes in the formulations of the invention presents a huge advantage as it is then possible to increase total energy substrate loading significantly without saturating glucose and fructose transporters and consequent gastrointestinal (GI) distress due to backup of sugars and salts in the stomach and GI tract.

It must also be considered that because the formulations of the invention contain many components for rapid and efficient delivery of fuel energy, the formulations do not require the presence of all components to be effective. For instance, most sports energy drinks contain an abundance of simple sugars such as dextrose (glucose) and dextrose-based carbohydrate energy forms such as sucrose and maltodextrins. Such concoctions are potentially injurious to diabetic and other insulin-resistant persons. However, even with deletion of dextrose and dextrose derivatives, by using derivatives of carbohydrate metabolism (i.e., lactate and pyruvate), ketones and ketone bodies, amino and fatty acids, the formulations of the invention would provide sugar free carbohydrate energy to and be efficacious for diabetic, other insulin-resistant persons, and others wishing to avoid dietary sugars and carbohydrates.

To reiterate, according to the invention "biological viability" is an inclusive term meaning that the substance is digestible, absorbable from the GI tract, circulates in the blood, is taken up by muscles and other tissues, and offers some useful functional advantage such as a fuel energy source (e.g., lactate, pyruvate, glutamate, glycerol and N-acetyl cysteine), a gluconeogenic precursor (e.g., glycerol, lactate and pyruvate), a hydrating agent (glycerol, as disclosed above), a vasodilator (e.g., arginine), and an essential electrolyte ($Na^+$, $K^+$, $Mg^{++}$, and $Ca^{++}$), for multiple biologically beneficial effects.

The formulations according to the invention may include, beyond the molecular compounds disclosed above, include simple carbohydrates such as glucose, sucrose, fructose and maltodextrin, and/or amino acids such as glutamate, glutamine, leucine, isoleucine, valine and mixtures of them as illustrated in FIGS. 1-21. Boundaries of mixture and tonicity stated above and illustrated in FIGS. 1-21 for beverages and gels apply also to A energy substrates and the intended mode of delivery; specifically for delivery via beverage or gel: ≈300 mEq/L, 1,000≤mEq/L, and <1,000 mEq/L.

The formulations according to the invention further include simple carbohydrates such as glucose, sucrose, fructose and maltodextrin, and/or amino acids such as glutamate, glutamine, leucine, isoleucine, valine and mixtures of them as illustrated in FIGS. 1-21. In addition to providing energy in the form of as carbohydrates, including mono- and di-saccharides (sugars) and maltodextrins (glucose polymers and other forms of starches), using our unique formulations. For example, in the formulations of the invention, including formulas 14 and 15 in FIGS. 1-21, which contain some of the molecules of the invention, it is possible to provide carbohydrate energy in forms not typically identified as sugars and starches. Instead, the energy forms are lactate and pyruvate, downstream products of sugar and carbohydrate metabolism. The types of individuals identified are CrossFit athletes (a trademarked name) and keto athletes, as well as diabetics or others with glucose intolerance and insulin resistance.

The formulations according to the invention are suitable for preparing oral dietary supplements, such as beverages, gels and the like, for increasing fluid, energy and electrolyte availability to athletes and others engaged in extreme physical activity such as soldiers and manual laborers in temperate, hot and dry or hot and humid environments as well as individual suffering illness and injury such as diabetes.

To this purpose the dietary supplements of the invention contain, in addition to the above formulations, other supportive dietary carbohydrate energy sources, specifically glucose and fructose which utilize specific transporters allowing movement of those solutes from the intestine into the blood.

As exemplified in the formulations in the FIGS. 1-21, dry components (powders) are presented for ready dilution typically in 1 liter of water. However, the ingredients can be prepared and presented to an individual seeking support of energy and electrolytes in other forms not limited to gels, chews, tablets, wafers, bars and the like.

In blending ingredients to achieve the preferred systems of nutrient delivery presented in FIGS. 1-21, note that no unnatural, ex vivo synthesized ingredients are included. Rather, what is prescribed are mixtures of naturally occurring biological compounds, mostly GRAS-listed (Generally Accepted As Safe) materials currently approved for human consumption.

Examples include: Sodium-L-+-lactate, Sodium-L-+-pyruvate, Glycerol di-lactate, mono-palmitate ester, lactic acid ester of mono and diglyceride, Glycerol tri-lactate, Glycerol mono-acetate, Glycerol di-acetate, mono-palmitate, and Glycerol tri-acetate. Noteworthy in the above example formulas is that in the formulas combinations of the A groups are identified. Comparisons of formulations are noteworthy also in use of inorganic cations as $R_1$ that contribute to "salt" content and saltiness of the formulation to taste or the ability of electrolyte replacement. Hence, future formulations could be designed to include substances comprised of naturally occurring compounds that associate by electrostatic charge (e.g., $Na^+$-Lactate) or weak covalent bonding as in acetic, fatty and lactic acid esters of mono- and di-glycerides, already approved for human consumption, as well as their respective triglyceride analogs.

Advantages of the new formulations of the invention are demonstrated below with data on a professional cyclist over a defined course. The tests were performed in a blinded fashion.

In our research, taking a standard drink, the best performance of a professional cyclist was a sustained power output of 410 w (6.26 w/kg body weight) for 19 minutes. In contrast, performance of the same athlete taking a FIGS. 1-21 drink allowed him to maintain a power output of 436 w (6.77 w/kg) for 19 minutes, or an 8% increase in power output over the same athlete taking a standard sugar-based drink. Again, in both cases, the athlete was unaware of drink contents.

Considering that in major competitions such as the Tour de France that was won in 2020 by less than a 0.005% time margin, any improvements of more than a fraction of a percent can be decisive; the new drink engenders a clear benefit in performance.

As it is stated above, the formulations of the invention will be a breakthrough in the field of health and wellness. On one hand, as previously described, the advantages for energy availability are significantly higher than with any other current drinks in the market. On the other hand, the biggest tendency in the area of health & wellness is to decrease carbohydrate ingestion. While athletic people with perfectly functioning mitochondria should not be afraid of carbohydrate, millions of people are misinformed and reduce carbohydrate intake including energy drinks that contain carbohydrate. However, by reducing dietary carbohydrate energy sources, the energy levels and performance capacity (of any level of athleticism) will be affected and decreased. Decreased performance because of poor nutrition leads to fatigue, overtraining, decreased enjoyment and decreased adherence to fitness activities.

The formulations of the invention are a great alternative to the current products in the market as glucose or fructose are not essential and can be substituted with the formulations of the invention which will be of great value and great alternative fuels for those fitness enthusiasts who are avoid sugar ("sugar-phobic") as well as for populations with type 2 diabetes or metabolic syndrome which as of today account for ~52% of US adult population (~100 million people). The formulations of the invention can also be of great value for individuals with Type 1 diabetes (T1D) that is characterized by the lack of production of insulin.

In summary, the novel formulations of the invention are the next generation of sports drinks and drinks for health and wellness (also called "smart drinks") which improves performance by delivering energy directly to cell's mitochondria and increasing the significantly the amount of energy delivered to the cells. Furthermore, the formulations of the invention will revolutionize the market of health and wellness due to the lack of insulin secretion to enter the cells as well as the improvement in mitigating hypoglycemia in people with T1D helping them in managing their condition.

To summarize, nutritional formulations are disclosed for humans and mammals including a GNG precursor or MCC with the molecular compounds disclosed above.

The formulations according to the invention are suitable for preparing oral dietary supplements, such as beverages, gels and the like, for increasing fluid, energy and electrolyte availability to athletes and others engaged in extreme physical activity such as soldiers and manual laborers in temperate, hot and dry or hot and humid environments as well as individual suffering illness and injury such as diabetes.

To this purpose the dietary supplements of the invention contain, in addition to the above formulations, other supportive dietary carbohydrate energy sources, specifically glucose and fructose which utilize specific transporters allowing movement of those solutes from the intestine into the blood.

Note that while Formulations 14 and 15 in FIGS. 1-21 are rich in providing energy substrates they contain no amendments typically identified as mono- or di-saccharide sugars, glucose polymers or starches. In Formula 15, FIGS. 1-21 energy is supplied by lactate in the form of salts, glycerol di-lactate, mono-palmitate ester, as well as amino acids and proteins as contained in whey protein there being no free sugar or glucose polymer content.

Preferred Embodiments of the Formulations of the Invention (Including Use of the Molecules Disclosed Above)

A preferred embodiment of the formulations of the invention consists of two molecules, a MCC or GNG precursor molecule and glycerol backbone molecule with a carrier molecule R that is glycerol (i.e., $R_3$) that is esterified with an A group that is MCC or GNG precursor (i.e., $A_1$) plus an A group that is a fatty acid (i.e., $A_3$). Biological viability exists with all the components of the two molecules of the formulation meaning that the two molecules of the formulation and the constituent components of the two molecules of the formulation resulting from being hydrolyzed in the gut after ingestion are digestible, absorbable from the GI tract, circulates in the blood, are taken up by muscles and other tissues, and offers some useful functional advantage such as a fuel energy source (e.g., MCC or GNG precursor on first and second molecule of the formulation), a gluconeogenic precursor (e.g., GNG precursor on the first and second molecule of the formulation), a hydrating agent (e.g., carrier group glycerol on the second molecule of the formulation), and an essential electrolyte (e.g., carrier group on the first molecule of the formulation), for multiple biologically beneficial effects. Using the two molecules of the formulations maximizes biological viability by including multiple functional groups in all categories of biological viability. Additionally, functional groups on either the first or second molecule of the formulation that add signaling properties to the formulation will act as a ligand to signal membrane proteins that facilitate biological processes that are beneficial for the individual when the formulations are used. For example, when $A=A_1$=lactate, the lactate on the molecule(s) of the formulations will act as a signaling molecule via binding as ligand to G-protein coupled lactate receptor (GPR81 aka HCAR1). When $A=A_2$=beta-hydroxybutyrate, the beta-hydroxybutyrate on the molecule(s) of the formulations will act as a signaling molecule via binding as ligand to G-protein couple receptor (GPR109 a and b).

For example, in this embodiment of a formulation of the invention using an MCC or GNG precursor plus an esterified glycerol backbone molecule allows for multiple functional groups to become available when used as an energy substrate solution. For example, if lactate is the preferred GNG precursor for the molecule of the formulation and palmitate is the fatty acid functional group for the molecule of the formulation, and the first MCC or GNG precursor molecule of the formulation has a carrier group that is sodium and the second molecule has a carrier group that is glycerol, when the formulation is digested and hydrolyzed in the gut to its constituent parts these two molecules will contribute at least one sodium, one glycerol, two lactates and one palmitate all with multiple biological pathways and biological viability. The biological viability of the constituent parts of the two molecules of the formulation means all components are digestible, absorbable from the GI tract, circulates in the blood, are taken up by muscles and other tissues, and offers some useful functional advantage such as a fuel energy source (e.g., lactate from both molecules of the formulation and palmitate from the second molecule of the formulation), a gluconeogenic precursor (e.g., lactate from the first and second molecule of the formulation and glycerol from the second molecule of the formulation), a hydrating agent (glycerol from the second molecule of the formulation), and an essential electrolyte ($Na^+$ from the first molecule of the formulation). As well, given that lactate acts as a signaling molecule, addition of lactate on the two molecules of the formulation in this example allows lactate to act as a ligand for the GPR81 (HCAR1) protein that is involved in anti-inflammation in response to activation of the inflammasome.

A preferred embodiment of the formulations of the invention consists of a MCC or GNG precursor plus a carrier molecule R that is glycerol (i.e., $R_3$) that is esterified with an A group that is MCC or GNG precursor (i.e., $A_1$) plus an A group that is a ketone or ketone body (i.e., $A_2$) and an A group that is a fatty acid (i.e., $A_3$). Biological viability exists with all the components of the two molecules of the formulation meaning that the two molecules of the formulation and the constituent components of the two molecules of the formulation resulting from being hydrolyzed in the gut after ingestion are digestible, absorbable from the GI tract, circulates in the blood, are taken up by muscles and other tissues, and offers some useful functional advantage such as a fuel energy source (e.g., MCC or GNG precursor on first and second molecule of the formulation and ketone or ketone body on the second molecule of the formulation), a gluconeogenic precursor (e.g., GNG precursor on the first and second molecule of the formulation), a hydrating agent (e.g., carrier glycerol on the second molecule of the formulation), and an essential electrolyte (e.g., carrier group on the first molecule of the formulation), for multiple biologically beneficial effects. Using the two molecules of the formulations maximizes biological viability by including multiple functional groups in all categories of biological viability. Additionally, functional groups on either the first or second molecule of the formulation that add signaling properties to the formulation will act as a ligand to single membrane proteins that facilitate biological processes that are beneficial for the individual when the formulations are used.

A preferred embodiment of the formulations of the invention consists of a MCC or GNG precursor plus a carrier molecule R that is glycerol (i.e., $R_2$) that is esterified with an A group that is MCC or GNG precursor (i.e., $A_1$) plus an A group that is a ketone or ketone body (i.e., $A_2$) that is chosen from beta-hydroxybutyrate or acetoacetate and an A group that is a fatty acid (i.e., $A_3$). Biological viability exists with all the components of the two molecules of the formulation meaning that the two molecules of the formulation and the constituent components of the two molecules of the formulation resulting from being hydrolyzed in the gut after ingestion are digestible, absorbable from the GI tract, circulates in the blood, are taken up by muscles and other tissues, and offers some useful functional advantage such as a fuel energy source (e.g., MCC or GNG precursor on first and second molecule of the formulation and from beta-hydroxybutyrate or acetoacetate on the second molecule of the formulation), a gluconeogenic precursor (e.g., GNG precursor on the first and second molecule of the formulation), a hydrating agent (e.g., glycerol on the second molecule of the formulation), and an essential electrolyte (e.g., carrier group on the first molecule of the formulation), for multiple biologically beneficial effects. Using the two molecules of the formulations maximizes biological viability by including multiple functional groups in all categories of biological viability. Additionally, functional groups on either the first or second molecule of the formulation that add signaling properties to the formulation will act as a ligand to single membrane proteins that facilitate biological processes that are beneficial for the individual when the formulations are used. For example, if a beta-hydroxybutyrate group is on the first or second molecule of this embodiment of the formulation the beta-hydroxybutyrate will act as a signaling molecule via binding as ligand to G-protein coupled receptor (GPR 109 a and b). Realizing that no molecule exist that includes beta-hydroxybutyrate bound to a glycerol backbone carrier group as describe in this embodiment of the formulations of the invention, the inventors herein describe new chemical entities that would enable the important biological benefits of such molecules.

A preferred embodiment of the formulations of the invention consists of a MCC or GNG precursor plus a carrier molecule R that is glycerol (i.e., $R_2$) that is esterified with an A group that is MCC or GNG precursor (i.e., $A_1$) plus an A group that is a ketone or ketone body (i.e., $A_2$) and an A group that is a fatty acid (i.e., $A_3$) that is chosen from acetate, octanoate, palmitate, oleate, or stearate from the $A_3$ group. Fatty acids such as acetate, octanoate, palmitate, oleate, or stearate vary depending on the length of the carbon chain and depending on the length are transported through the intestine into the blood stream. Because of the various transport mechanisms that exist for fatty acids and the differences between fatty acid transport, MCC and GNG precursor (e.g., lactate, pyruvate) transport and ketone body (e.g., beta-hydroxybutyrate, acetoacetate) transport, molecules containing combinations wherein any of the energy sources exist and are easily hydrolyzed to their constituent components in the gut can deliver fuel energy for different intensities of exercise, different durations of exertion as well as beneficial outcome measures for the ill and injured. Hence, Biological viability exists with this embodiment of the formulations because all the components of the two molecules of the formulation after being hydrolyzed in the gut after ingestion are digestible, absorbable from the GI tract, circulates in the blood, are taken up by muscles and other tissues, and offers some useful functional advantage such as a fuel energy source (e.g., MCC or GNG precursor on first and second molecule of the formulation and from ketone or ketone bodies and from fatty acids such as acetate, octanoate, palmitate, oleate, or stearate on the second molecule of the formulation), a gluconeogenic precursor (e.g., GNG precursor on the first and second molecule of the formulation), a hydrating agent (e.g., glycerol on the second molecule of the formulation), and an essential electrolyte (e.g., carrier group on the first molecule of the formulation), for multiple biologically beneficial effects. Using the two molecules of the formulations maximizes biological viability by including multiple functional groups in all categories of biological viability. Additionally, functional groups on either the first or second molecule of the formulation that add signaling properties to the formulation will act as a ligand to single membrane proteins that facilitate biological processes that are beneficial for the individual when the formulations are used.

A preferred embodiment of the formulations of the invention consists of a MCC or GNG precursor plus a carrier molecule R that is glycerol (i.e., $R_2$) that is esterified with two A groups that consists of a MCC or GNG precursor (i.e., $A_1$) plus an A group that is a fatty acid (i.e., $A_3$). Biological viability exists with this embodiment of the formulations because all the components of the two molecules of the formulation after being hydrolyzed in the gut after ingestion are digestible, absorbable from the GI tract, circulates in the blood, are taken up by muscles and other tissues, and offers some useful functional advantage such as a fuel energy source (e.g., MCC or GNG precursor on first and two MCCs or GNG precursors on the second molecule of the formulation and from a fatty acid on the second molecule of the formulation), a gluconeogenic precursor (e.g., GNG precursor on the first and two on the second molecule of the formulation), a hydrating agent (e.g., glycerol on the second molecule of the formulation), and an essential electrolyte (e.g., carrier group on the first molecule of the formulation), for multiple biologically beneficial effects. Using the two molecules of the formulations maximizes biological viability by including multiple functional groups in all categories of biological viability. Additionally, functional groups on either the first or second molecule of the formulation that add signaling properties to the formulation will act as a ligand to single membrane proteins that facilitate biological processes that are beneficial for the individual when the formulations are used A preferred embodiment of the formulations of the invention consists of a MCC or GNG precursor plus a carrier molecule R that is glycerol (i.e., $R_2$) that is esterified with an A group that is lactate or pyruvate (i.e., $A_1$) plus an A group that is a fatty acid (i.e., $A_3$). Biological viability exists with this embodiment of the formulations because all the components of the two molecules of the formulation after being hydrolyzed in the gut after ingestion are digestible, absorbable from the GI tract, circulates in the blood, are taken up by muscles and other tissues, and offers some useful functional advantage such as a fuel energy source (e.g., MCC or GNG precursor on first and two lactates or pyruvates on the second molecule of the formulation and from a fatty acid on the second molecule of the formulation), a gluconeogenic precursor (e.g., GNG precursor on the first and two lactates or pyruvates on the second molecule of the formulation), a hydrating agent (e.g., glycerol on the second molecule of the formulation), and an essential electrolyte (e.g., carrier group on the first molecule of the formulation), for multiple biologically beneficial effects. Using the two molecules of the formulations maximizes biological viability by including multiple functional groups in all categories of biological viability. Additionally, functional groups on either the first or second molecule of the formulation that add signaling properties to the formulation will act as a ligand to single membrane proteins that facilitate biological processes that are beneficial for the individual when the formulations are used. For example, if a lactate group is on the first or second molecule of the formulation it will act as a signaling molecule via binding as ligand to G-protein coupled lactate receptor (GPR81 aka HCAR1) and will act as an anti-inflammatory response via inflammasome signaling via lactate binding to HCAR-1 that downregulates Toll like receptor induction of the pyrin domain-containing protein 3 (NLRP3) inflammasome and production of IL1-β, via Arrestin beta 2 (ARR-β2).

A preferred embodiment of the formulations of the invention consists of a MCC or GNG precursor that consists of a carrier group R that is selected from the $R_1$ group and an A group that is selected from the $A_1$ group plus a carrier molecule R that is glycerol (i.e., $R_2$) that is esterified with an A group that is MCC or GNG precursor plus (i.e., $A_1$) an A group that is a fatty acid (i.e., $A_3$). As previously described, this formulation contains molecules with biological viability but in this case the first molecule of the formulation further describes the $R_1$ group of the MCC or GNG precursor molecule that makes up the cations of inorganic salts such as Sodium ($Na^+$), Potassium ($K^+$), Magnesium ($Mg^{++}$) and Calcium ($Ca^{++}$) plus mono- and di-phosphorous ($H_2PO_4$ and $H_2PO_3$). More than one MCC or GNG precursor molecule of the formulation can be added to the formulation and in a preferred embodiment of the invention $R_1$ salts could be in ratios as they exist in human blood.

A preferred embodiment of the formulations of the invention consists of a MCC or GNG precursor plus a carrier molecule R that is glycerol (i.e., $R_3$) that is esterified with an A group that is MCC or GNG precursor (i.e., $A_1$) plus an A group that is a fatty acid (i.e., $A_3$) wherein the formulation also includes one or more salts. Here again the molecules of the formulations when ingested and hydrolyzed to the constituent components add biological viability, and the formulation can further contribute salts that are inorganic cations of Sodium ($Na^+$), Potassium ($K^+$), Magnesium ($Mg^{++}$) and Calcium ($Ca^{++}$) plus mono- and di-phosphorous ($H_2PO_4$ and $H_2PO_3$) in ratios as they exist in human blood that further adds biological viability to the formulation.

A preferred embodiment of the formulations of the invention consists of a MCC or GNG precursor plus a carrier molecule R that is glycerol (i.e., $R_2$) that is esterified with an A group that is MCC or GNG precursor (i.e., $A_1$) plus an A group that is a fatty acid (i.e., $A_3$) wherein the formulation also includes one or more anaplerotic compounds from the list of: succinate, glutamate, malate. Again, the molecules of the formulation add biological viability when ingested and hydrolyzed in the gut of the individual. In this embodiment of the invention, anaplerotic compounds are also described which when added to the formulation would support diverse anaplerotic and anabolic and energy substrate functions in the ill and injured as well as in healthy individuals under stress.

A preferred embodiment of the formulations of the invention consists of a MCC or GNG precursor plus a carrier molecule R that is glycerol (i.e., $R_2$) that is esterified with an A group that is MCC or GNG precursor (i.e., $A_1$) plus an A group that is a fatty acid (i.e., $A_3$) wherein the formulation is an aqueous solution. In this embodiment in addition to the biological viability from the two molecules of the formulation the formulation is further described as an aqueous solution. Isotonic aqueous solutions (Iso) [≈300 milliequivalents per Liter (mEq/Liter)] are ideal for oral or intravenous administration.

A preferred embodiment of the formulations of the invention consists of a MCC or GNG precursor plus a carrier molecule R that is glycerol (i.e., $R_2$) that is esterified with an A group that is MCC or GNG precursor (i.e., $A_1$) plus an A group that is a fatty acid (i.e., $A_3$) wherein the formulation is an aqueous solution and wherein the glycerol backbone molecule is in a concentration of at least about 5% weight by volume. In this embodiment in addition to the biological viability from the two molecules of the formulation the formulation is further described by the weight to volume of the components of the formulation as an aqueous solution. Adding more solute to a solution increases the ability to biologically transport the solute only up to the point where individual transporters can no longer interact with and accommodate transport of additional molecules. For instance, intestinal glucose uptake appears to saturate when presented with a glucose solution of 6% (w/v). Hence, to move more solute, presenting the intestine with an 8-10% glucose solution will be of no practical advantage, and may give rise to bloating and other gastro-intestinal (GI) discomforts. In contrast, if a solution of lesser glucose concentration (e.g., 4-6% glucose) is augmented with 2% fructose and 2% arginyl-lactate, then significantly more rapid and greater total intestinal solute absorption and oxidation can occur. Using the molecules of the formulations, a significant percentage of the energy substrates of the formulations could come from both the first and second molecule of the formulation and glucose could be administered without saturating the glucose transporters.

A preferred embodiment of the formulations of the invention consists of a MCC or GNG precursor plus a carrier molecule R that is glycerol (i.e., $R_2$) that is esterified with an A group that is MCC or GNG precursor (i.e., $A_1$) plus an A group that is a fatty acid (i.e., $A_3$) wherein the formulation is an aqueous solution and wherein the glycerol backbone molecule is in a concentration of at least about 30 g/L. In this embodiment of the invention the specific gram amount of the second molecule of the invention has been describes. This amount of material maximizes the number of lactates that exist on the glycerol backbone and therefore can contribute about 20 g of lactate per dose of the energy substrate that utilizes the formulation of the invention. Additional lactate on the MCC or GNG precursor molecule of the formulation will also contribute to the total g amount of lactate per serving.

A preferred embodiment of the formulations of the invention consists of a MCC or GNG precursor plus a carrier molecule R that is glycerol (i.e., $R_2$) that is esterified with an A group that is MCC or GNG precursor (i.e., $A_1$) plus an A group that is a fatty acid (i.e., $A_3$) wherein the formulation is an aqueous solution and wherein the components are of the formulation are in a concentration of at least about 8% weight by volume. As above, the biological viability of the molecules of the invention are designed to maximize the solute uptake by the substrate transporters.

A preferred embodiment of the formulations of the invention consists of a MCC or GNG precursor plus a carrier molecule R that is glycerol (i.e., $R_2$) that is esterified with an A group that is MCC or GNG precursor (i.e., $A_1$) plus an A group that is a fatty acid (i.e., $A_3$) wherein the formulation is an aqueous solution and wherein the formulation includes one or more of the following cations: $Na^+$, $K^+$, $Ca^{++}$, $Mg^+$. Herein the embodiment describes further biological viability by adding specific cation electrolytes found in blood. Electrolytes to maintain plasma osmolarity and nutritional status to support fluid and electrolyte balance should be in the same ratio as they are present in a healthy individual. For example, $Na^+$, $K^+$, $Ca^{++}$, $Mg^{++}$ would be given in the ratios and amounts of 145, 4, 2.5, 1.5, milliequivalents per liter (mEq/l). As well phosphate anion (or anions) would be given at 1.0 milliequivalents per liter (mEq/l).

A preferred embodiment of the formulations of the invention consists of a MCC or GNG precursor plus a carrier molecule R3 that is glycerol that is esterified with an $A_1$ group that is MCC or GNG precursor plus an $A_3$ group that is a fatty acid wherein the formulation is an aqueous solution and wherein the formulation includes one or more of the following anions: $Cl^-$, $HPO_4^{2-}$, $H_2PO_4^-$. As above, a preferred embodiment of the formulation could contain anion counter ions including hydrogen phosphate ($HPO_4^{2-}$) and dihydrogen phosphate ($H_2PO_4$—), and chloride ($Cl^-$) to further balance plasma osmolarity and nutritional status and further improve the biological viability of the formulations.

A preferred embodiment of the formulations of the invention consists of a MCC or GNG precursor plus a carrier molecule R that is glycerol (i.e., $R_2$) that is esterified with an A group that is MCC or GNG precursor (i.e., $A_1$) plus an A group that is a fatty acid (i.e., $A_3$) wherein the formulation is an aqueous solution, and the formulation is electrically neutral. When a formulation is composed of related numbers of counter ions, specifically anions (negatively charged ions) and cations (positively charged ions) the product is without charge and further leads to the balancing of plasma osmolarity and nutritional status and further improves the biological viability of the formulations.

A preferred embodiment of the formulations of the invention consists of a MCC or GNG precursor plus a carrier molecule R that is glycerol (i.e., $R_2$) that is esterified with an A group that is MCC or GNG precursor (i.e., $A_1$) plus an A group that is a fatty acid (i.e., $A_3$) wherein the formulation is an aqueous solution with a molarity of about 300 mM-1000 mM and that is suitable for enteral, parenteral or oral use.

A preferred embodiment of the formulations of the invention consists of a MCC or GNG precursor plus a carrier molecule R that is glycerol (i.e., $R_2$) that is esterified with two A groups that are MCC or GNG precursor (i.e., $A_1$) that includes two lactate groups, two pyruvate groups, or one lactate group and one pyruvate group plus an A group that is a fatty acid (i.e., $A_3$). Maximizing the MCC or GNG precursor group $A_1$ in this embodiment of the formulation will result in a highly efficacious energy substrate solution as the MCC or GNG precursor groups are important energy substrates for all tissues. MCC or GNG precursor compounds can work synergistically in the human body, particularly because transport across cellular membranes is carrier (i.e., transport protein) mediated. For instance, in oral rehydration of a patient or athlete, the intestinal wall presents a diffusion barrier to the movement (flux) of metabolites, electrolytes and water from intestinal lumen into the blood. Importantly, for rehydration of the ill, injured, or depleted athlete, we know that the intestinal carriers for glucose and lactate are "sodium-mediated." Hence, by providing sodium ion from NaCl or Na-Lactate, the uptake of both lactate anions and glucose molecules are increased (facilitated). Importantly, while the movement of water through its "Aquaporin" carrier is not ionically mediated, the movement of water follows the movement of other solutes such as sodium cations, lactate anions and glucose molecules down concentration gradients. Simply rephrased, the intestinal transport and uptake of more energy solutes brings more electrolytes and more water into the blood of the dehydrated, energy- and electrolyte-depleted patient, athlete or other individual.

A preferred embodiment of the formulations of the invention consists of a MCC or GNG precursor plus a carrier molecule R that is glycerol (i.e., $R_2$) that is esterified with an A group that is MCC or GNG precursor (i.e., $A_1$) that includes two lactate groups, plus an A group (i.e., $A_3$) that is a fatty acid. Again, the biological viability of the formulation is designed to maximize the efficaciousness of the energy substrate solution for the athlete as well as the injured and ill. When lactate is selected from the $A_1$ group, the formulation contains the most important energy substrate for the body.

A preferred embodiment of the formulations of the invention consists of a MCC or GNG precursor plus a carrier molecule R that is glycerol (i.e., $R_2$) that is esterified with an A group that is MCC or GNG precursor (i.e., $A_1$) that includes one lactate group, plus an A group that includes two fatty acids ($A_3$).

A preferred embodiment of the formulations of the invention consists of a MCC or GNG precursor that consists of a carrier group $R_1$ that is a salt and an $A_1$ group that is lactate or pyruvate plus a carrier molecule R that is glycerol (i.e., $R_2$) that is esterified with an A group that is MCC or GNG precursor ($A_1$) plus an A group that is a fatty acid (i.e., $A_3$). Selecting salt or salts for the formulations can enhance biological viability. Salts would be included in a ratio that is the same as in the blood (e.g., $Na^+$, $K^+$, $Ca^{++}$, $Mg^{++}$ would be given in the ratios and amounts of 145, 4, 2.5, 1.5, milliequivalents per liter (mEq/l).

A preferred embodiment of the formulations of the invention consists of a MCC or GNG precursor that consists of a carrier group $R_1$ that consists of a salt that is sodium, potassium, magnesium, or calcium and an $A_1$ group that is lactate or pyruvate plus a carrier molecule R that is glycerol (i.e., $R_2$) that is esterified with an A group that is MCC or GNG precursor (i.e., $A_1$) plus an A group that is a fatty acid (i.e., $A_3$).

A preferred embodiment of the formulations of the invention consists of a MCC or GNG precursor that is sodium lactate plus a carrier molecule R that is glycerol (i.e., $R_2$) that is esterified with an A group that is lactate (i.e., $A_1$) plus an A group that selected from acetate, octanoate, palmitate, oleate or stearate (i.e., $A_3$).

A preferred embodiment of the formulations of the invention consists of a MCC or GNG precursor that is sodium lactate plus a carrier molecule R that is glycerol (i.e., $R_2$) that is esterified with two $A_1$ groups that are both lactate plus an $A_3$ group that is selected from acetate, octanoate, palmitate, oleate or stearate.

A preferred embodiment of the formulations of the invention consists of a MCC or GNG precursor that is sodium lactate plus a carrier molecule R that is glycerol (i.e., $R_2$) that is esterified with an $A_1$ group that is lactate plus two $A_3$ groups that are selected from acetate, octanoate, palmitate, oleate or stearate.

A preferred embodiment of the formulations of the invention consists of a MCC or GNG precursor plus a carrier molecule R that is glycerol (i.e., $R_2$) that is esterified with an A group that is MCC or GNG precursor (i.e., $A_1$) plus an A group that is a fatty acid (i.e., $A_3$). The formula would also include carbohydrates such as fructose, glucose, and maltodextrin. To maximize the biological viability of a formulation multiple energy substrates can be chosen. In this example of the formulation fructose, glucose and maltodextrin would be added to maximize the solute in the volume of solution without saturating the substrate transporters of each of the components of the formulation.

A preferred embodiment of the formulations of the invention consists of a MCC or GNG precursor plus a carrier molecule R that is glycerol (i.e., $R_2$) that is esterified with an A group that is MCC or GNG precursor (i.e., $A_1$) plus an A group that is a fatty acid (i.e., $A_3$). The formula would also include carbohydrates such as fructose, glucose and maltodextrin wherein the MCC or GNG precursor is 2.5 g of sodium lactate, the glycerol backbone molecule is 50 g, the fructose is 20 g, the glucose is 20 g and the maltodextrin is 20 g.

A preferred embodiment of the formulations of the invention consists of a MCC or GNG precursor plus a carrier molecule R that is glycerol (i.e., $R_2$) that is esterified with an A group that is MCC or GNG precursor (i.e., $A_1$) plus an A group that is a fatty acid (i.e., $A_3$). The formula would also include carbohydrates such as fructose, glucose and maltodextrin wherein the MCC or GNG precursor is 2.5 g of sodium lactate plus 0.5 g of potassium lactate plus 1 g of calcium lactate, plus 0.6 g of magnesium lactate, the glycerol backbone molecule is 50 g, the fructose is 20 g, the glucose is 20 g and the maltodextrin is 20 g.

A preferred embodiment of the formulations of the invention consists of a MCC or GNG precursor plus a carrier molecule R that is glycerol (i.e., $R_2$) that is esterified with an A group that is MCC or GNG precursor (i.e., $A_1$) plus an A group that is a fatty acid (i.e., $A_3$). The formula would also include carbohydrates such as fructose, glucose and maltodextrin wherein the MCC or GNG precursor is 2.5 g of sodium lactate plus 0.5 g of potassium lactate plus 1 g of calcium pyruvate, plus 0.6 g of magnesium pyruvate, the glycerol backbone molecule is 50 g, the fructose is 20 g, the glucose is 20 g and the maltodextrin is 20 g.

Preferred Embodiments of the Formulations of the Invention (Including Use of the Molecules Disclosed Above)

A preferred embodiment of the chemical entity of the invention includes a glycerol backbone and three functional groups B1, B2, B3, that are each esterified to one carbon of the glycerol, wherein at least one of the functional groups includes a GNG precursor or MCC and at least one of the three functional groups includes a ketone or ketone body group. At least two of the B functional groups esterified to the glycerol backbone must be occupied at any of the positions on the glycerol backbone and the third position can be a hydroxyl group. A preferred embodiment of the chemical entity of the invention includes a glycerol backbone and three functional groups B1, B2, B3, that are each esterified to one carbon of the glycerol, wherein at least one of the functional groups includes a GNG precursor or MCC and at least one of the three functional groups includes a ketone or ketone body group. Health and wellness with novel chemical structures as described in this embodiment of the invention can be indicated for use for athletes as well as the acute and chronic injured and ill such as during traumatic brain injury or diabetes. For example, a chemical entity that provides short- and longer-term carbohydrate energy via multiple metabolic pathways without the use of insulin to signal cellular uptake would be advantageous. As well, new chemical entities to provide fuel energy and signaling properties would be advantageous and would add to the biological viability of a formulation if such chemical entities would be added to the solution. These chemical entities using a glycerol backbone provide other advantages by minimizing salt carriers associated with other molecules frequently used in formulations. For example, a sodium lactate and a sodium beta hydroxybutyrate molecules would add two sodium molecules whereas this proposed embodiment of a new chemical entity would eliminate all sodium. As well, this new chemical entity wherein a lactate and beta hydroxybutyrate are esterified to a single glycerol provides multiple energy to the body and also adds signaling molecules of both lactate and beta-hydroxybutyrate when hydrolyzed in the gut. For example, when lactate is included, the lactate will act as a signaling molecule via binding as ligand to G-protein coupled lactate receptor (GPR81 aka HCAR1). When beta-hydroxybutyrate is included, the beta-hydroxybutyrate on the new chemical entity will act as a signaling molecule via binding as ligand to G-protein couple receptor (GPR109 a and b).

A preferred embodiment of the chemical entity of the invention includes a glycerol backbone and three functional groups B1, B2, B3, that are each esterified to one carbon of the glycerol, wherein at least one of the functional groups includes a GNG precursor or MCC, at least one of the three functional groups includes a ketone or ketone body group and at least one of the three functional groups includes a fatty acid group. As above the increased efficacy of this new chemical entity would add to the biological viability when used in athletes are the injured or ill. In addition to the above embodiment a fatty acid group would also be added to the chemical entity which would further increase the energy carrying capacity of the chemical entity.

A preferred embodiment of the chemical entity of the invention includes a glycerol backbone and three functional groups B1, B2, B3, that are each esterified to one carbon of the glycerol, wherein at least one of the functional groups includes a GNG precursor or MCC and at least one of the three functional groups includes a ketone or ketone body group wherein the ketone or ketone body group is chosen from beta-hydroxybutyrate, acetoacetate.

A preferred embodiment of the chemical entity of the invention includes a glycerol backbone and three functional groups B1, B2, B3, that are each esterified to one carbon of the glycerol, wherein at least one of the functional groups includes a GNG precursor or MCC and at least one of the three functional groups includes a ketone or ketone body group wherein the ketone or ketone body group is chosen from beta-hydroxybutyrate, acetoacetate.

A preferred embodiment of the chemical entity of the invention includes a glycerol backbone and three functional groups B1, B2, B3, that are each esterified to one carbon of the glycerol, wherein at least one of the functional groups includes a GNG precursor or MCC wherein the GNG precursor or MCC includes lactate or pyruvate and at least one of the three functional groups includes a ketone or ketone body group.

A preferred embodiment of the chemical entity of the invention includes a glycerol backbone and three functional groups B1, B2, B3, that are each esterified to one carbon of the glycerol, wherein at least one of the functional groups includes a GNG precursor or MCC, at least one of the three functional groups includes a ketone or ketone body group and at least one of the three functional groups includes a fatty acid group wherein the fatty acid group includes acetate, octanoate, palmitate, oleate or stearate.

A preferred embodiment of the chemical entity of the invention includes a glycerol backbone and three functional groups B1, B2, B3, that are each esterified to one carbon of the glycerol, wherein on B is lactate, one B is beta-hydroxybutyrate and one B is a hydroxyl group.

A preferred embodiment of the chemical entity of the invention includes a glycerol backbone and three functional groups B1, B2, B3, that are each esterified to one carbon of the glycerol, wherein one B is lactate, one B is beta-hydroxybutyrate and one B is palmitate.

Preparation and Synthesis of Formulations

As exemplified in the formulation in the FIGS. 1-21, dry components (powders) are presented for ready dilution typically in 1 liter of water. However, the ingredients can be prepared and presented to an individual seeking support of energy and electrolytes in other forms not limited to gels, chews, tablets, wafers, bars and the like.

In blending ingredients to achieve the preferred systems of nutrient delivery presented in FIGS. 1-21, note that no unnatural, ex vivo synthesized ingredients are included. Rather, what is prescribed are mixtures of naturally occurring biological compounds, mostly GRAS-listed (Generally Accepted As Safe) materials currently approved for human consumption.

Examples include: Sodium-L-+-lactate, Sodium-L-+-pyruvate, Glycerol di-lactate, mono-palmitate ester), Glycerol tri-lactate, Glycerol mono-acetate, Glycerol di-acetate, mono-palmitate, and Glycerol tri-acetate. Noteworthy in the above example formulas is that in Formulas 15-21 combinations of $A_1$, $A_2$, and $A_3$ are identified. Comparisons of formulations are noteworthy also in use of inorganic cations as R1 that contribute to "salt" content and saltiness of the formulation to taste or the ability of electrolyte replacement and R2 that carry one, two or three A groups. Hence, future formulations could be designed to include substances comprised of naturally occurring compounds that associate by electrostatic charge (e.g., sodium lactate) or weak covalent bonding as in acetic, fatty and lactic acid esters of mono- and di-glycerides, already approved for human consumption, as well as their respective triglyceride analogs.

Methods of Use of the Invention Compounds and Formulations for Various Populations With the formulations of the invention based on Lactate Shuttle Theory predict that by adding lactate, pyruvate and other compounds unique to the invention it is possible to increase significantly the ingestion of carbohydrate and other energy forms of up to 160 g/h. In this paradigm, lactate and pyruvate are to be considered carbohydrate intermediate compounds. Lactate and pyruvate can be delivered in diverse carrier forms such as glycerol esters, bound to amino acids (e.g., arginine, lysine, cysteine, histidine and their derivatives, thiolesters, and salts of inorganic ions ($Na^+$, $K^+$, $Ca^{++}$, or $Mg^{++}$). As well, glycerol esters of monocarboxylates and GNG precursors can be combined with glycerol esters of short-, medium- and long-chain fatty acids, or ketones acetoacetate and/or beta hydroxy butyrate. Moreover, these sugar-free molecules and mixtures can be amended by addition of simple sugars such as monosaccharides glucose and fructose, the disaccharide sucrose, or glucose polymers (maltodextrins). The hourly dose of up to 160 g/hour can be managed in several ways using diverse platforms.

The energy substrate dose of 160 g/hr can be delivered in two bottles containing 500 to 750 ml of fluid usually carried by or provided to athletes.

The energy substrate dose of 160 g/hr can be delivered in two or more gel, wafer, tablet, or bar formats each consumed and followed shortly by 500-750 ml of water. This latter approach of not using a fluid, energy, electrolyte mix but only water and gels, bars is an alternative allowing athletes to feel free in dumping bottle contents over their heads, neck, back and even feet.

Competitive Sports Performance

Lactate is probably the preferred fuel by most cells in the body, especially for skeletal muscle, the heart, brain or kidneys as demonstrated by inventor Brooks in many papers and patents. Glucose must be degraded to pyruvate through the 9 steps of glycolysis. During rest and low exercise conditions, pyruvate is oxidized to Acetyl-CoA in mitochondria through the enzyme pyruvate dehydrogenase (PDH) which enters the tricarboxylic citric acid (TCA) cycle, also called the Krebs cycle. However, under high exercise intensities, the rapid rate of glycolysis and a mass action effect don't allow for pyruvate to be oxidized to acetyl-CoA in mitochondria. Hence, pyruvate is then reduced to lactate in cytosol even under fully aerobic conditions. This reaction happens mainly in glycolytic fibers (fast-twitch muscle fibers). Lactate is then exported by fast twitch muscle fibers to adjacent slow-twitch muscle fibers where it enters through its transporter the monocarboxylate 1 (MCT1) and is oxidized in mitochondria to Acetyl-CoA through the mitochondrial lactate oxidative complex (mLOC) as demonstrated by Hashimoto.

Furthermore, cytosolic lactate production is indispensable for the continuation of glycolysis as during this process, $NAD^+$ is depleted in cytosol and the only reaction that can replenish it is the reduction of pyruvate to lactate and oxidation of NADH to $NAD^+$ for the continuation of glycolysis. Otherwise, glycolysis would be halted and muscle contraction at high exercise intensities would not be possible without lactate production.

Moreover, during low exercise intensities, fatty acids are highly oxidized for energy purposes. However, during high exercise intensities, fatty acids are not the ideal source of fuel as their oxidation is quite slow as opposed to glycolysis which produces ATP at a much higher rate than fatty acid oxidation. Therefore, there is a switch from fatty acid metabolism to glycolysis which has been named the "crossover concept" by Brooks and Mercier. Lactate seems indispensable for this metabolic switch as it exerts both endocrine and autocrine actions on fatty acid metabolism during exercise. Lactate binds to a receptor called GPR81 on the surface of adipocytes inhibiting lipolysis as shown by Liu. Furthermore, lactate decreases the activity of mitochondrial fatty acid transporter carnitine palmitoyl 1 and 2 (CPT 1 and CPT2) as shown by inventor San-Millin which in turns decreases fatty acid oxidation in favor of glycolysis.

There are also important differences in the cellular transportation of glucose and lactate. In the intestinal lumen, the typical sources of carbohydrates like glucose, maltodextrin and fructose must enter though the SGLT-1 and GLUT5 transporters while lactate relies on a different transporter which as pointed above is a monocarboxylate (MCT). Most sports drinks are composed of different types of carbohydrates, mainly glucose, fructose, and maltodextrin. It has been shown that increased carbohydrate utilization increases athletic performance. However, when there is a high consumption of carbohydrate like in the case of high intensity exercise, carbohydrate transporters will get saturated which will result in a delay in the transportation of carbohydrate across the intestinal lumen. This will result in reduced availability of carbohydrate in the bloodstream for skeletal muscle as well as a reduced gastric emptying leading to gastrointestinal (GI) distress leading to "feeling bloated", diarrhea or vomiting which are events typical in endurance sports. The actual recommendations for carbohydrate intake during endurance events are 90 g/h as shown by Jeukendrup. However, most elite endurance athletes and teams are already doing 125-150 g/h. In many situations, this high amount of carbohydrate poses an extra stress on carbohydrate transport across intestines leading to GI distress.

However, lactate does not need carbohydrate transporters to enter the blood stream as it uses its own MCT transporter. Therefore, the addition of lactate to carbohydrate will increase the amount of carbon sources in the blood stream for skeletal muscle oxidation and energy. This is a significant advantage for athletes as not only there is a significant increase in the amount of fuel available but also it decreases GI distress. Finally, as pointed before, lactate oxidation is significantly faster than any carbohydrate source which makes lactate a very advantageous fuel for energy purposes.

Health & Wellness: Exercise for Different Populations

Diabetes

Lactate is a great fuel for populations with type 1 and type 2 diabetes (T1D and T2D) as well as insulin resistance. Individuals with insulin resistance, T1D and T2D cannot process carbohydrate properly for multiple reasons.

Populations with Diabetes (Type 1 and Type 2 diabetes)

People with Type 1 and Type 2 diabetes (T1D, T2D) have significant issues with insulin production and resistance. People with T1D cannot produce insulin and therefore, all types of monosaccharides, disaccharides and glucose polymers will need insulin in order to be taken up by cells. For purposes of the invention, we consider glucose polymers (including maltodextrins) and other high glycemic index molecules effectively as sugars (or sugar-like compounds), even if they do not meet such definition in some of the art, because of their physiological effects on diabetics and others. When such sugars (sugar-like compounds) are used, people with T1D will need to inject themselves with insulin. While this is effective, it leads often to an exacerbated insulin secretion which will lead to hypoglycemia, which can be quite serious and increase the incidence of accidents, like when riding a bike or running as many times these patients get dizzy and even lose conscience.

In the case of people with T2D, while in the first phases of their diabetes they produce insulin, the cell receptors for insulin become resistance and therefore the aforementioned sugars cannot be taken up properly. Eventually and over the years, many people with T2D stop producing insulin from pancreas and they need to inject themselves with insulin.

Hence, for people with diabetes, our formulation could be of great help as the use of lactate and pyruvate is not insulin-dependent to be taken up by cells and therefore a person with diabetes should be able to get adequate amount of energy without the need of insulin and the possible side effects from insulin utilization. An energy substrate dose up to 160 g/hr can be delivered in two bottles containing 500 to 750 ml of fluid usually carried by or provided to athletes. An energy substrate dose of up to 160 g/hr can be delivered in two or more gel, wafer, tablet, or bar formats each consumed and followed shortly by 500-750 ml of water.

Type 1 Diabetes

In the case of individuals with T1D, they don't produce insulin and therefore, they cannot transport carbohydrate across cell membranes. Hence, they need to use injectable insulin on a daily base and multiple times a day. Individuals with T1D must be quite careful with their carbohydrate intake as if they don't control it properly, glucose will accumulate in the blood which will lead to serious acute health problems like ketosis and long-term problems like neuropathies and retinopathies which can lead to amputation of feet as well as severe loss of vision and even blindness. Furthermore, the wrong management of insulin can lead to severe hypoglycemic episodes which can get to be lethal and cause long-term effects on the brain. Since carbohydrate are indispensable source of energy, individuals with T1D must be very careful planning their carbohydrate intake as they will need to adjust their insulin correctly. Since lactate doesn't need insulin to enter the cells, we should not expect a need of insulin in these population and as mentioned above, lactate is the end-product of glucose anyways, so it would be a great addition (although probably not a substitution) to carbohydrate in this population.

Type 2 Diabetes and Insulin Resistance

T2D is a completely different disease than T1D although the main clinical characteristics are similar: hyperglycemia and difficulty to transport glucose from the blood into cells. The etiology of T2D is different than T1D. While in the latter there is no production of endogenous insulin by the pancreas, individuals with T2D produce insulin but it is not enough or efficient in order to transport glucose into cells and ultimately, oxidize glucose in mitochondria during resting conditions. Especially at rest, the "activation" of glucose transporters (GLUT) is stimulated by insulin which translocates GLUT transporters from cytosolic vesicles to the cell surface. We have recently showed that the transporter of pyruvate in mitochondria, mitochondrial pyruvate transporter (MPC) is significantly decreased (as well as pyruvate oxidation) in sedentary individuals respect to moderately active individuals. Therefore, in addition to insulin, glucose oxidation (pyruvate) is significantly decrease in both transport and oxidation in mitochondria at rest which could explain the long-term failure of insulin to fix hyperglycemia. In the end, glucose enters the cell and is degraded to pyruvate which must be transported and oxidized in mitochondria which according to our study would mean that a decrease in pyruvate transport and oxidation may be a key process in T2D. Therefore, extra amounts of carbohydrate will pose an extra metabolic challenge on those individuals with reduced capacity to both transport and oxidize pyruvate.

Today ~50% of US adult population is either pre-diabetic or have T2D, according to the CDC, and about ⅔ of all insulin used in the US is by patients with T2D instead of T1D who the population were traditionally using insulin. Hence, people with pre-diabetes, insulin resistance and T2D are told by their clinicians to moderate or even suppress carbohydrates from their diet. This may lead to decreases in energy availability derived from carbohydrate. Furthermore, individuals with T2D are strongly advised to exercise. However, a significant decrease in carbohydrate from their diets can lead to difficulties for exercising due to decrease energy supply which may lead to abandon exercise as a key therapeutic tool to combat T2D.

The use of lactate as a fuel energy would be of great use by this populations as lactate does not need insulin to enter the cells to be oxidized for energy and could revolutionize the nutrition in populations with both T1 and T2 diabetes.

Seriously Ill and Injured Patient, Including Intensive Care Unit (ICU) Patients

Glucose control is a very important issue for ICU patients where hyperglycemia is highly related to mortality. Most ICU patients develop insulin resistance in the acute phase of being in the ICU. However, it is well known that ICU patients need about 2-3 times higher glucose needs than healthy individuals in order to heal and recover. Furthermore, All ICU patients suffer from some form of muscle wasting or catabolism, also called (ICU-acquired weakness). As previously mentioned, protein breakdown (proteolysis) is an excellent gluconeogenic source produced in the liver. An excessive muscle breakdown characteristic of ICU patients can lead to excessive gluconeogenesis and if the patient develops insulin resistance as also characteristic, it can elicit significant issues to maintain proper glucose control and decrease survival rates.

Our formula with lactate and pyruvate bypasses insulin secretion as previously mentioned and therefore, it can be a great source of carbohydrate necessary to heal and recover. An energy substrate dose of up to 120 g can be delivered at bedside through drinking in different bottles containing 500 to 750 ml of fluid. Further, if it is possible to chew, an energy substrate dose of up to 120 g can be delivered in several gels, wafers, tablets, or bar formats each consumed and followed shortly by 500-750 ml of water.

Patients admitted to the ICU are fighting for their lives and nutrition is critical for them. Hypermetabolism and substrate partitioning are typical metabolic characteristic of these patients as shown by many scientists including inventor San Millán. The increase in energy demand, especially glucose leads to decreased glycogen stores and catabolism. Furthermore, ICU patients suffer mitochondrial dysfunction and insulin resistance leading to hyperglycemia. These metabolic status poses a significant burden for survival of ICU patients. On one hand, they need an increase in carbohydrate but on the other hand, many patients' insulin resistance at the ICU. Hence, carbohydrate feeding is challenging for many ICU patients.

The use of lactate could be of great advantage to many ICU patients as they would get faster energy than carbohydrate and without the need of insulin.

Lactate is the preferred fuel by most cells in the body, especially skeletal muscle. Hence, this is an advantage over traditional carbohydrates present in sports drinks like glucose, fructose or maltodextrins.

Lactate is also oxidized to energy significantly faster than any traditional carbohydrate. This is a substantial advantage during high intensity exercises as lactate is oxidized in less than 5 minutes while glucose, fructose and sucrose can take between 20-30 min.

Lactate should be used in the last part of any competition as its oxidation takes less than 5 minutes and it is superior to any other carbohydrate. 20-40 g of lactate would be a superior fuel in the last 30 min of a competition.

Lactate would be an excellent source of energy for the muscles at half time of many team sports where the half time is about 15 minutes. Lactate is oxidized in less than 5 minutes, giving athletes an extra advantage as they would have fuel replenished and available by the time they go back out to the field for the second and crucial part of the game/match.

Lactate is to be used during the competition in order to provide faster energy than traditional carbohydrates. It is of special importance in the last part of most sports including cycling, triathlon, running, football, basketball, etc., where the energetic component is key in the last minutes of competition.

The actual recommendations for carbohydrate intake during endurance events are 90 g/h. However, most elite athletes and teams are already doing 125-150 g/h. In many situations this high amounts of carbohydrate pose an extra stress on carbohydrate transport across intestines leading to GI distress. Using 20-40 g/h of lactate maintains a high level of fuel in addition to 90-100 g/h of carbohydrate without saturating carbohydrate transporters and causing GI stress.

Lactate can be provided in a powder form and be mixed with water and/or along with different carbohydrates. Lactate can also be used in a gel form alone or with other carbohydrates.

For athletes, it is recommended to combine lactate with other carbohydrates. An example could be to use 20-40 g of lactate in combination with 60-80 g of carbohydrate.

Lactate can also be used for recovery in athletes as it will be converted to energy as well as can be converted to glycogen.

For populations with pre-diabetes, T2D and T1D, lactate should be used alone to avoid insulinemic response as in the case of carbohydrates.

Populations with pre-diabetes, T2D and T1D can have 20-40 g/h during exercise instead of carbohydrate.

Lactate should be used by wellness and fitness populations who "ran away" from carbohydrate and insulin spikes. Lactate should be taken before, during and after physical activity in a similar manner to athletes.

For ICU patients, lactate can be a great fuel bypassing insulin-mediated carbohydrate utilization which is key in the healing process. Since lactate is the end-product of glucose and metabolized much faster and not requiring insulin, lactate supplementation could be quite beneficial to ICU patients. The general notion is that lactate should be provided to patients in small doses throughout the day.

Our formula with lactate and pyruvate bypasses insulin secretion as previously mentioned and therefore, it can be a great source of carbohydrate necessary to heal and recover. An energy substrate dose of up to 120 g can be delivered at bedside through drinking in different bottles containing 500 to 750 ml of fluid. Further, if it is possible to chew, an energy substrate dose of up to 120 g can be delivered in several gels, wafers, tablets, or bar formats each consumed and followed shortly by 500-750 ml of water.

Sports Performance and Competition

The energy substrate dose up to 160 g/hr can be delivered in two bottles containing 500 to 750 ml of fluid usually carried by or provided to athletes.

The energy substrate dose up to 160 g/hr can be delivered in two or more gel, wafer, tablet, or bar formats each consumed and followed shortly by 500-750 ml of water. This latter approach of not using a fluid, energy, electrolyte mix but only water and gels, bars is an alternative allowing athletes to feel free in dumping bottle contents over their heads, neck, back and even feet.

The addition of salts as lactate carriers, mainly sodium, would also override the need to use electrolytes during the competition. Our formula has a composition of 2.5 g of sodium lactate per dose, which is the equivalent to 500 mg of sodium. This amount of sodium is similar or even higher than the current top electrolyte-based drinks in the market. Furthermore, our drink contains other lactate and pyruvate carriers like potassium, magnesium and calcium which are in proportion to physiological levels which would be helpful to restore these essential minerals utilized during exercise and metabolic stress.

Furthermore, the addition of glycerol as a carrier will add extra source of energy as well as allow some water retention to maintain plasma volume, which could be important to prevent or manage dehydration.

Fitness Oriented Populations

Similar principles as described above apply to fitness populations. A tendency in the last years among this population is to avoid sugars and in general carbohydrates in the form of monosaccharides, disaccharides and glucose polymers. A main reason argued by this population is that these sugars are "bad" for health as seen in people with type 2 diabetes. These sugars increase insulin release which could lead to hyperinsulinemia which has been linked to multiple physiological and metabolic disorders like insulin resistance, a main attribute of type 2 diabetes. Hence, this type of population tends to move away for sugary drinks. However, a disadvantage of this population is that by not having enough carbohydrates during and after the exercise, their energy levels as well as recovery will be decreased which will impact the benefits of exercise. Furthermore, during high exercise intensities, a lack of carbohydrate will promote the breakdown of muscle protein (proteolysis) as several amino acids can be either transformed in the liver to glucose (gluconeogenesis) or be utilized directly as energy source in skeletal muscle mitochondria. An increase in muscle breakdown for energy purposes can lead to catabolism and therefore be detrimental to exercise as well as lead to overtraining and fatigue, which are quite common among this population.

The utilization of our formula will provide great amount of energy as both lactate and pyruvate are considered carbohydrate compounds. However, since the uptake of both lactate and pyruvate doesn't require insulin, we are not expecting the insulin spike characteristic of the aforementioned form of carbohydrates ("sugars").

Furthermore, the addition of multiple amino acids as carriers of lactate and pyruvate could also be incorporated as energy for muscles.

An ideal dose of carbohydrate energy substrate (lactate and pyruvate) for this population would be up to 120 g/h solely lactate and pyruvate without any monosaccharides, disaccharides, glucose polymers or similar "sugars".

The energy substrate dose up to 120 g can be delivered in two bottles containing 500 to 750 ml of fluid usually carried by or provided to athletes.

The energy substrate dose up to 120 g can be delivered in two or more gel, wafer, tablet, or bar formats each consumed and followed shortly by 500-750 ml of water.

The Diet and Fitness Industries

In the last two decades a movement against carbohydrate and insulin has been predominant among many fitness enthusiasts running away from "sugars" and any form of carbohydrate that causes insulin spikes. This has led to the introduction of multiple anti-carbohydrate diets such as the paleo diet, high fat-low carb diets (HFLC), protein diet, ketogenic diet . . . etc. Most of these fitness enthusiasts use protein drinks/bars and fat for their workouts. However, the source of energy in these products is quite poor compared to carbohydrates and lactate. A common complaint of many fitness enthusiasts going into these diets is that they feel that their energy levels tank, not only during their exercise routines but also during their normal daily activities.

The use of lactate products for this population could be ideal as they would have plenty of energy during their workouts without causing spikes of insulin or just the desire of not having carbohydrate yet using an alternative source of energy (lactate) which is not "sugar" or not insulin-dependent.

Methods of Addressing Nutritional Status Incorporating Blood Metabolic Measurements, Including Use of the Disclosed Molecules and Formulations Precision Medicine (i.e., individualized or personalized medicine) can be achieved using new inventions coupled with existing technologies and formulations. The new technologies proposed herein to assess Body Energy State (BES) and glycemic control for the purpose of achieving Exquisite Glycemic Control (EGC) in supporting body, brain and other tissues in the ill and injured as well as healthy individuals under exercise, thermal and other stresses include: diagnostics of physiological (metabolic and nutritional) status of patients, personalized prescriptions, unique formulations, targeted formulation therapies (Clamp Therapy), devices, and complementary devices and system software to analyze and interpret data so that healthcare professionals and other individuals may individualize (personalize) nutritive support given to patients and other individuals on a near, real-time or continuous basis. A diagnostic and companion therapy is identified and described as: (1) monitoring target ranges for metabolites involved in establishing BES and achieving EGC, and (2) varying delivery of formulations to intended blood metabolite concentrations (i.e., physiological metabolite targets for diagnostic clamps) to support metabolic needs of injured and other tissues during normal physiology and pathophysiology such as metabolic crises that occur during illness, injury, increased exertion, etc. The invention describes the process and components necessary to achieve precision in nutrient and drug delivery, especially during rest, and under stress such as exercise as well as the acute and chronic phases of illness and injury when patients are presenting with one or more metabolic crises. Specialized chemical entities, compositions and formulations designed to treat and support the ongoing stress related to increased energy needs and metabolic crises are also presented. The process consists of four steps: 1) Diagnosis, 2) Prescription, 3) Treatment, and 4) Single and/or Continual Determination and Reassessment. The components of the system are categorized in five ways: 1) Diagnostics, 2) Pharmaceutical and Nutraceutical Compounds, Chemical Entities, Compositions and Formulations 3) Devices, 4) Software for Analysis and Prescription at the device and systems level, and 5) Data collection, retrieval and interpretation on the local system level (i.e., local network) and across and throughout multiple networks such as "cloud" networks wherein data is accessed, interpreted and interfaced by the multiple actors of the ecosystem to facilitate and automate current manual processes (i.e., Digital Health, Digital Therapeutics). As well, while the components can be described individually, in aggregate they can be assembled to perform as either a hybrid closed-loop (i.e., feedback loop) system or a fully automated closed-loop system for providing precision in nutrient and drug delivery to healthy, ill or injured person or other mammal.

Diagnostic procedures for assessment of Body Energy State and glycemic control for the purpose of achieving Exquisite Glycemic Control may be achieved by the combination of enteral, parenteral or oral delivery of macro- and micro-nutrients with complimentary, simultaneous and ongoing monitoring of important metabolite levels to support diverse physiological functions in the ill and injured as well as healthy individuals under exercise, thermal and other stresses such as metabolic crises associated with pathophysiology of acute and chronic illness and injury. When the infusion rate of a drug or nutritional formulation containing a metabolite or mixture of metabolites is adjusted to achieve a target blood (or other sample such as serum, saliva, tears or sweat, cerebral spinal fluid, etc.) concentration, the metabolite of interest (e.g., [lactate] of 4-5 mM, [beta-hydroxy butyrate of 0.2-0.5 mM, or [glucose] of 5 mM, etc.), is said to be "clamped." Targets of lactate include low and high ranges of values (low of 0.5-1 mM and high of greater than 4-5 mM). Physiological ranges of lactate can range from 0.5 to 30 mM. Lactate clamp therapy can include any values of lactate above the normal low range of 0.5-1 mM achieved through the administration of exogenous nutrition and drugs containing the metabolite of interest.

Precision (i.e., personalized, individualized) medicine for clinical nutrition of ill or injured, or other humans or other mammals utilizes nutritional formulations and drugs approved through regulatory agencies for use as sources of calories and metabolic/molecular diagnostics including isotomics/mass fragmentography and a database to interpret metabolic/molecular diagnostic measurements of flux for blood metabolites such as glucose, lactate, amino- and keto-acids and glycerol, the rate of glyconeogenesis, as well as muscle and liver glycogen contents. Either individually, or in combination, the identified physiological fluxome and metabolome processes (i.e., blood metabolite concentration and rate of turnover levels) can be taken as biomarkers for BES and EGC. Moreover, the methodology includes measurement of glucose and lactate concentrations and flux under conditions of injury and illness as well as other physiologic conditions that challenge body energy state and glycemic control.

Algorithms to prescribe precision clinical nutrition can be derived from one or many of these biomarkers. Applications of prescriptions for treatment of specific indications for use including clinical nutrition and other injuries and illnesses can apply to ill or injured patients, healthy individuals, athletes and other mammals. One approach to supplementing nutrient delivery to achieve BES and EGC is to regulate the administration rates of gluconeogenic (GNG) precursors or monocarboxylate compounds (MCC) that function as body and tissue energy fuels, gluconeogenic precursors, signaling molecules (i.e., ligands) or a combination of all functions.

Another approach of supplementing nutrient delivery to achieve BES and EGC is to regulate the oral administration or infusion rate, or rates of gluconeogenic precursors or monocarboxylate compounds to clamp (i.e., achieve a set level or target of the metabolite of interest, such as 4 mM [lactate]) and simultaneously monitor and target [glucose], [ketones] or other markers of micro and macro nutrient status.

Still another approach of supplementing nutrient delivery to achieve BES and EGC is to regulate the oral, enteral or parenteral administration or infusion rate, or rates (increase, decrease, or target a particular concentration), of gluconeogenic precursors or monocarboxylate compounds to clamp (i.e., achieve a set level of a different metabolite of interest), blood [glucose] of 5 mM.

Yet another approach is to individualize and optimize nutrient delivery to improve BES and achieve EGC is to deliver multiple nutrients and other amendments, thereby utilizing different, but complementary pathways of energy transduction to achieve a more rapid and greater cumulative effect. Utilization and utilization rates of nutritional molecules involves gastrointestinal absorption, cellular uptake, mitochondrial uptake, and molecular metabolism/respiration.

Moreover, another approach is to give enteral or parenteral nutrient replacement formulations as predicted from standard equations, e.g., (Harris and Benedict 1918), and then supplement nutrient delivery to achieve BES and EGC regulating the oral, enteral or parenteral administration or infusion rate, or rates (up, down, or to a particular level), of gluconeogenic precursors or monocarboxylate compounds to clamp (i.e., achieve a set level of different metabolites of interest), blood [glucose] of 5 mM. This approach recognizes that macronutrient energy supplementation can only be achieved on the background of adequate energy nutrition.

For assessment of BES and achievement of EGC this invention anticipates use of equipment for assessment of multiple analytes of interest using a pan-omics analysis (i.e., use of multiple analyses consisting of the metabolome, fluxome, proteome, genome, etc.). Panomics is the integration of "-omics" various subfields such as genomics, transcriptomics, proteomics and metabolomics. Measurements of glucose and lactate concentrations (and increasingly ketone concentrations) are most important to identify the maintenance of glucose control under normal, exercising and stress responses to illness and injury, but a panel of physiological pan-omic measurements used as targets for nutritional and drug intervention can be used. Instruments that simultaneously measure lactate and glucose concentrations exist. Similarly, devices exist for simultaneous analysis of blood glucose and ketone levels. As well, devices to measure blood gases, electrolytes, glucose and lactate exist, but currently such devices are not utilized to target exquisite glucose control through administration of formulations containing nutritional macronutrients as well as physiological salts such as contained in drug nutritional formulations.

An example of such an instrument can be found from manufacturers such as Radiometer, Nova Biomedical, YSI and Abaxis among others. Analysis of pH, pCO2, pO2, sO2, ctHb, FO2Hb, FCOHb, FMetHb, FHHb, FHbF, $cK^+$, $cNa^+$, $cCa^{++}$, $cCl^-$, cGluc, cLac, cCrea, ctBil can be made from a single biological sample, and variations of analytes can be measured depending on the device utilized. Some devices have FDA and other regulatory standards clearance. All devices cleared for the medical setting to measure glucose and lactate used in combination with nutritional therapy to target (clamp) a specific concentration of lactate, glucose or other physiological metric can be embodiments of the invention.

Other examples of Electrochemical Sensors for clinical analysis exist that allow for continuous monitoring of blood metabolite concentrations such as the Optiscan Optiscanner 5000 and 6000 medical devices which continuously reports glucose and lactate blood concentrations and cleared for use in the critical care setting.

While suggestions for lactate monitoring in acute and critical care settings exist, none have proposed lactate clamping as therapy in disease and injury states, and further none have proposed to infuse lactate containing formulations to control or clamp blood [glucose] in the physiological set point of about 5 mM (range of about 4-7 mM) in adults, 3.6 mM (range of about 1.5-5.3) in breast fed babies and 4.0 mM (range of about 2.5-6.2) in formula fed babies. During stress induced hyperglycemia as a result of metabolic crises, in some cases the range of glucose concentration my temporarily be elevated as a normal response. A target clamp for blood glucose concentration may be temporarily elevated to a target range of about 8-11 mM. In contrast, contemporary scientific interpretation of lactate as an energy substrate or signaling molecule is little understood or used by medical professionals. Part of the history of avoiding lactate treatment is that hyperlactatemia (elevated blood [lactate]) has been taken as a predictor of mortality from injury or illness, rather than a measure of physiological strain in response to stress. However, an alternative view of the physiological role of lactate as an energy substrate, a gluconeogenic precursor and signaling molecule (i.e., a lactormone) under the scientific framework of Lactate Shuttle theory (Brooks 1984, Brooks 1985, Brooks 2002, Brooks 2009, Brooks 2019) is only now starting to be recognized and discussed openly in high impact factor medical and scientific journals (Bakkar, Nijsten et al. 2013) (Garcia-Alvarez, Marik et al. 2014).

Lactate Biosensing Strip: The present invention provides application of a lactate biosensing strip including a working electrode and a reference electrode. The two electrodes are deposited on an electrically insulated base support, the working electrode being formed by immobilizing an enzyme lactate oxidase and an electro mediator on an inorganic graphite matrix and the graphite layer is deposited on a silver layer and the reference electrode being formed by depositing silver chloride on another silver layer for diagnostic clamps.

Continuous, in vivo, monitoring of lactate and glucose using sweat, microdialysis or minimally invasive devices such as a wire based dual analyte sensor for glucose and lactate also exist. As well, the development of lab-on-a-chip devices for biochemical analysis has seen an explosive growth over the past decade. Some disposable plastic biochips incorporating smart passive microfluidics with embedded on-chip power sources and integrated sensor arrays for applications in clinical diagnostics and point-of-care testing exist. The biochip has a unique power source using on-chip pressurized air reservoirs, for microfluidic manipulation, avoiding the need for complex microfluidic pumps. Multi-analyte detection for $pO_2$, $pCO_2$, glucose and lactate have been measured simultaneously.

i-STAT Corporation has commercialized handheld biochemical device for point-of-care use with disposable biochips that detect blood gases, pH, $pCO_2$, $pO_2$; electrolytes, $Na^+$, $K^+$, $Ca^{2+}$, $Cl^-$, $Mg^{2+}$; metabolites, glucose, urea, lactate; etc. The system design uses a discrete sample receptacle containing one or multiple microfabricated electrochemical electrodes on a chip, and a low-cost general-purpose electromechanical read-out device. i-STAT's core competency is its high-volume planar microfabrication processes for sensors. Sensors are manufactured with wafer-scale, planar, thin film, microfabrication processes (chip manufacturing processes). Potentiometric devices use silver metal electrodes with a sensor end that is converted to silver chloride by electrode anodization in an oxidizing chloride bath. The $CO_2$ sensor is a Severinghaus design, the $O_2$ electrode is an amperometric Clark electrode design, glucose sensors are based on an iridium film RF sputtered and patterned by lift-off, and hematocrit is measured using AC conductimetry.

Other devices include a contact lens incorporating a biosensor for sensing bioanalytes present in tears. Accurate determination of glucose levels in body fluids, such as blood, urine, and cerebro-spinal fluid, is a major aid in diagnosing and improving the therapeutic treatment of diabetes and has the potential to reduce the long-term risk for developing coronary artery disease, visual impairment, renal failure, and peripheral vascular disease.

The most widespread example of a commercial biosensor is the blood glucose biosensor. A biosensor is a compact analytical device, which converts a biologically induced recognition event into a usable signal and includes three parts: (1) the sensitive biological material; (2) the detector element that transforms the signal resulting from the interaction of a target analyte with the biological material into another signal (optical, piezoelectric, electrochemical, etc.) that can be more easily measured and quantified; and (3) the signal processor that is primarily responsible for the display of the results in a user-friendly way (i.e., user interface (UI) and user experience (UX)) and educates the user in a way that adds value or beneficial health and wellness.

In recent years, a few devices have been introduced that allow users to test their glucose levels by drawing blood from their arm instead of the tips of their fingers, such as implantable enzymatic sensors, such as the Medtronic-MiniMed CGM.

Glucose and other metabolites are also monitored using a patch technology developed by, for example, Abbott and Dexcom that continuously monitor metabolites, such as glucose concentration over time and relay those findings to the end user to be used to assess health and wellness including diabetes control.

As a further, or alternative expression of assessing BES in the healthy, ill, injured and other humans or mammals under stress, muscle glycogen content can be non-invasively estimated using ultrasound technology or quantitatively by direct measurement of glucose production (percent fractional hepatic glycogenolysis) using isotomics. Both measurements techniques can indicate BES. Measurement of percent fractional hepatic glycogenolysis (% GLY) yields an absolute value for glycogen content whereas a qualitative measurement of muscle glycogen content yields a relative measurement. A relative measurement of BES can indicate BES as it relates to normal glycogen content. That is, a normal glycogen content in healthy individuals is 1.25 mg/100 g of muscle wet-weight, and a qualitative measurement of that value enables prescriptions for nutritive support. Providing, maintaining, increasing, decreasing, or ceasing oral, enteral or parenteral administration or infusion based on quantitative and qualitative measurements of glycogen that targets a nourished state allows the healthcare provider or other individual to prescribe individualized precision nutritional support for the healthy, ill or injured during the acute or chronic phase of hospitalization or general care. Likewise, healthy individuals or athletes can derive prescriptions from measurements of glycogen for optimal feeding that maximizes the anabolic state without the negative consequences of over- and underfeeding. Lactate clamp therapy and measurement of glucose and lactate concentrations in biological samples using either single measurement or continuous sampling techniques are included in the invention.

Targeted resuscitation therapy, such as lactate or other physiological salts and nutrients as well as signaling molecules include caloric delivery as well as volume and tonicity, i.e., fluid load, dose, target concentration, signaling event, etc.

Targeted resuscitation therapy includes signaling of key metabolic processes. For example, individual proteins or a panel of proteins such as HCAR1 (formerly GPR81), GPR 109 (109a and 109b), BDNF, TREK1, etc., can be signaled to start or end a physiological response when targeted resuscitation fluids are administered and monitored therapeutically as a companion diagnostic (i.e., closed-loop or feedback loop system) to achieve a specific physiological concentration and physiological outcome. Continuous monitoring of concentrations of key targets, such as glucose and lactate during administration of formulations specific for the indication of use, such as traumatic brain injury, acute pancreatitis, acute hepatitis, sepsis, metabolic crisis, etc., and other health and wellness outcomes including diabetes, diet and exercise will enable precise support of the metabolic, nutritional and inflammatory state of the patient.

Lactate monitoring is becoming standard of care and advocated due to potential diagnostic capabilities despite an evolving opinion of what the biomarker lactate means for treatment. With lactate therapy, the diagnostic interpretation is clearer for the use of lactate measurement because exogenous administration of pharmaceutical and nutraceutical compounds and formulations containing lactate are administered to achieve a target concentration in the individual. Historically, the indication for use of lactate concentration has been tied to hypoxia despite turnover (i.e., rate of appearance, rate of disappearance, production, clearance, flux) of lactate occurring continuously when oxygen supply is sufficient. However, even at the peak of Mt. Everest where oxygen supply is limited, lactate concentrations remain relatively low. Lactate production during stress of exercise and stress of illness and injury is most likely a protective mechanism that has evolved over time to generate much needed bioenergetic and signaling substrate by providing fuel directly to tissues in need and indirectly as a gluconeogenic precursor as well as a ligand to signal key proteins to activate physiological response to mitigate the stress and strain of healthy and unhealthy processes.

Some healthcare professionals indicate that lactate should be measured and compared over time including during first responder intervention and for duration of acute and chronic illness or injury even though the current indication for use as determined by regulatory agencies is most likely not physiologically correct. Indeed, the more accurate indication for use of lactate concentration would be as a marker of glycolysis or hypermetabolism. A high lactate concentration at the scene of the accident should indicate the need for formulations containing GNG and MCC precursors to directly fuel the injured body and brain, indirectly produce glucose exquisitely through gluconeogenesis and signal proteins to facilitate physiological action beneficial to the survival of the individual.

Estimating the increase in caloric and nutritional needs using lactate concentration early in the acute phase of illness and injury using standard calculations. For example, knowing that at the scene of the accident a patient with a higher lactate concentration is less likely to survive than a patient with a lower lactate concentration (Jansen, van Bommel et al. 2008) should guide the paramedic or first responder at the scene of the accident or in the emergency setting to start iv containing lactate compounds or solutions, such as commercial NutiCLA (inventors' brand name) at a rate to match the needs indicated by the Lactate Clamp Therapy. A higher concentration indicates a higher administration, infusion or dose of oral or iv exogenous lactate.

Extrapolating concentration to increase energy needs. Typical daily lactate production in resting humans is approximately 20 mmol/kg/day with a resting concentration approximately 1 mM. If the illness or injury increases lactate concentration above resting concentration and using a resting turnover rate of approximately 1.5 mg/kg/min (17 micromole/kg/min)=24.5 mmol/kg/day. If lactate rate of appearance (Ra) increases and is indicated from [lactate] using measuring device, the daily production could increase 3 or 4 times. For the health care provider, when [lactate] is below the lactate threshold of approximately 4-6 mM, the prescription should be to administer or infuse rapidly oxidized fuels such as lactate containing formulations. These formulations should as well allow for maximum energy delivery combined with physiological salts to keep both the acid base stable in the blood as best possible and support the micro- and macro-nutrient needs.

There is no good test for nutritional adequacy in the hospital or other setting. Today scientists and health care professionals such as physicians, nurses and clinical dietitians are looking for better technologies (Casaer and Van den Berghe 2014), acknowledge that there is no marker for adequacy of nutrition and state that the lack of technologies as medical diagnostics is a "favorite ax to grind." As well, albumen and other carrier proteins traditionally used as markers of nutritional adequacy drop because of capillary leak and have no relationship with caloric intake. A current problem in the field of the nutritional needs during the acute phase of injury stems from choosing to study surrogates without studying outcomes. However, outcome studies are expensive and take many enrolled patients. With advanced biomarkers using isotomics with intensive molecular anatomy through mass spectrometry, tracers and inventive fragmentography techniques, flux measurements combined with concentration measurements of the patients is now possible. Thus, the real-time application of therapeutics can be prescribed for the precise needs of the individual patient.

Fractional production of a profile of metabolites using mass fragmentology. A single spectrum can be used to measure body water enrichment and fractional production of glucose (Horning, U.S. Pat. No. 8,927,490). That same body water enrichment can also be applied to the measurement of another product analyte (metabolite, substrate) to measure fractional production based on hydrogen-deuterium incorporation into the product divided by the body water enrichment (precursor). Hence, a profile of fractional production of key metabolites can be obtained from a single biological sample.

Measurement of total enrichment of the product minus the body water enrichment divided by the body water enrichment enables measurement of fractional production of product. The approach can use one or more measurement of body water enrichment using product mass spectrum. A profile of products, routinely measured today, can now yield important fractional production rates using fragmentology.

Fractional production of metabolites (products) are useful for both basic scientific investigation and for the practice of precision medicine. A single biological sample and a single analysis of the biological sample can provide a profile of fractional production values. In medicine, fractional gluconeogenesis using this invention is proving to be useful for the practice of nutritional and metabolic control during metabolic crisis to enable the practice of exquisite glycemic control. Other fractional production values (e.g., fractional glycogenolysis, fractional glyceroneogenesis, etc.,) yield other useful physiological or pathophysiological information to diagnose and prescribe treatment for healthy and ill and injured individuals.

An example of fractional production (i.e., fluxomics, fractional metabolomics, fractional proteomics) is the use of a second metabolite to measure % D2O in body water such as glycerol through body water interaction via hydrogen-carbon isotope incorporation.

Glyceroneogenesis: A measurement of body water enrichment by mass fragmentation using $D_2O$ and mass fragments of glycerol. The pathway for body water equilibration with hydrogens on glycerol are formed from pyruvate and the deuterium enrichment of hydrogens on the C1 and C3 of triglyceride glycerol formed from pyruvate will be the same as that of body water.

Another example of fractional fluxomics is lactate to body water enrichment that can be measured by isolating carbon-hydrogen incorporation similar to glucose and glycerol. The invention envisions most substrates in the body to have a body water-substrate interaction that can be deduced by isolating the carbon-hydrogen that indicates body water equilibrium and comparing to the rest of the molecule's enrichment using isotomics (mass fragmentology). The invention also envisions that a single product can yield a measurement of body water enrichment that can be used to calculate the fractional production of any product that is in equilibrium with body water. Examples include glucose, glycerol and other small molecules that make up the metabolome, and proteins that make up the proteome. It is expected that the genome could be traced similarly and give insight to epigenetic effects such as the maternal effect.

Some reasons why fractional glycerol production (and other processes essential for life) are potentially useful for the practice of precision medicine include the ability to measure the steady transition to starvation similar to fractional glucose production, but this diagnosis might be better suited for a different type of patient.

Cerebral metabolism and Plasma lipid and hormone levels. Plasma lipids measured during 72 hours of starvation resulted in plasma free fatty acid and glycerol concentrations rising on each day of starvation. On the second and third days, plasma triglyceride concentrations increased from control level of 649+/−67 mg/l to a maximum of 1001+/−66 mg/1. Plasma cholesterol concentrations remained unchanged while glucose concentrations fell, and insulin did not change. Plasma glucagon levels doubled while secretin levels increased threefold. During the acute phase of illness and injury such as TBI, mean brain tissue glycerol concentration results from the increased availability of free fatty acids, and that elevated secretin and glucagon levels enhance lipolysis and hence provide substrates for triglyceride synthesis.

Glycerol measurements are important for the understanding of cerebral metabolism in the acute phase of illness and injury such as TBI. Glycerol has been shown to decrease significantly from 206 micromole/L to 9 micromole/L on the first day of injury as compared with the fourth day post injury. Using advanced measurements of glycerol flux in addition to concentration measurements would help to provide diagnostics useful to the clinician during the early phase of illness and injury and over the course of recovery to help guide therapy individualized for the specific patients' needs. As well, glycerol is efficacious in terms of expanding plasma volume to minimize dehydration (vide infra).

Using the example of fractional production of glucose and glycerol, it is already possible to measure both metabolites and mass spectra from a single analysis. Then, either one or both can be used to determine body water enrichment. That measurement of body water enrichment can then be used to measure fractional metabolism of a product molecule such as glucose in the example of fractional glucose production from gluconeogenesis (e.g., fGNG) using the spectra that indicates deuterium incorporation of the total product molecule minus body water enrichment derived from the fragmentation patter of the product divided by body water enrichment.

In the example for fGNG using glucose product we use two fragments of glucose. Glyceroneogenesis (i.e., fractional Glycerol or fGlycerol) can be calculated using body water derived from fragments of glycerol, glucose or average of both and using that value to calculate fGlycerol or fGNG using another fragment or multiple fragments to enable the calculation of deuterium incorporation into the product body water enrichment.

Measurement of fractional production using the invention could be done in one or many product metabolites. One can envision a metabolomic or proteomic profile of many molecules that are easily obtained from a single spectrum that can be used to measure body water enrichment to determine fractional metabolic function (e.g., fGNG, fGlycerol, fLactate, etc.) as a result of the ability to measure the molecular anatomy of a single molecule through fluxomics interpretation of the fragmentation patterns.

Measurement of multiple analytes for deuterium incorporation with simultaneous analysis of body water enrichment for the determination of and comparison of percentage rates of production to be used as targets for treatment. For example, glucose and lactate deuterium incorporation can be simultaneously determined by comparison of the fraction of deuterium in the analyte of interest (e.g., glucose and lactate, but not limited to glucose and lactate) and compared with the measurement of body water enrichment. Determination of the fraction of analyte production enables the physician or healthcare provider to prescribe precise therapy that will target the optimal fractional production indicating a healthy physiology.

Mass Fragmentography (i.e., Flux Spectroscopy, Flux Markers, Fluxoscopy, Fluxometry, Flux Mass Spectroscopy, Ionogenomics, Isotomics, Anatomy of a Molecule): Use of single biological sample for precise measurements of endogenous flux and effect of exogenous nutrient sources on endogenous production and utilization of glucose and other micro and macro nutrient substrates.

Advantages of using a single biological sample for precursor-product metabolic flux measurements as well as measurements of partitioning of energy substrate availability, such as when measuring fractional glucose production from gluconeogenesis, glycogenolysis including glucose Ra from exogenous dietary nutrients is more rapid and precise and uses less blood than conventional methodologies with consideration to instrumental limitations that might be predictable and corrected.

Small blood samples can be assayed to yield both static measurements of metabolite concentration as well as dynamic (flux) measurements yielding new dimensions of insight into a patient's or healthy individual's metabolic and nutritional status. In the case of glucose, a single biological sample processed in a single analysis of a mass spectrum yields actionable concentration and flux data on the nutritional and metabolic state of an individual thus guiding a health care professional in prescribing and delivering the appropriate nutrients to support body energy state and support euglycemia in healthy, ill, or injured patients.

Addition of Internal Standards Enables Measurement of Blood Concentration: In a biological sample, the concentration of a metabolite, such as glucose, can be determined by adding a known internal standard, that does not occur naturally or resolves independently from the analyte of interest, to an experimental sample of known weight, or volume, and comparing abundances of standard and unknown glucose in the experimental sample. Inclusion of a standard in an assay is referred to as internal standard technique. In practice, for assaying blood glucose concentration using principles of internal standard technique, a known amount of uniformly labeled $^{13}C$ glucose (U-$^{13}C$ glucose) is added to the biological sample of known volume (or mass). Then, a comparison of the natural abundance of unlabeled glucose to that of the internal standard yields blood glucose concentration.

Techniques and Instrumentation for Measuring Flux are Rapidly Evolving and allow for Innovative Uses for Medical Applications. An example of early measurements of flux using stable isotopes includes measurements of GNG by precursor product relationships, specifically using the isotopic enrichment of $1^3$C lactate from infused [3-$1^3$C]lactate appearing as the M+1 signal in newly produced glucose (Glenn, Martin et al. 2014). Knowing the enrichment of the precursor, and the enrichment in the product gives a measure of GNG from lactate. However, the technique takes days, if not weeks of chemistry and mass spectrometry, and is not feasible for providing actionable data in a clinical setting. In contrast, we have developed a rapid, micro assay that takes less than an hour (Horning and Brooks 2012) and will provide health care professionals with actionable data in managing a patient's BES.

Mass Isotopomer Distribution Techniques Enable Measurement of Fractional Synthesis Rates: Using multiple fragments (i.e., Mass Fragmentography or Ionogenomics) from a single mass spectrum of a molecule obtained from a small (e.g., 20 micro liter blood sample) enables determination of complex biological processes. For example, the change in fractional deuterium incorporation via gluconeogenesis as the subject transitions from a fasted to a fed state and back can be made using measurements of ion intensities of glucose fragments in mass spectrometry. Specifically, ion intensities of m/z 169 and 170 as expressed in mole percent excess (170/(169+170)) show average deuterium incorporation from gluconeogenesis into hydrogen atoms on carbons 1, 3, 4, 5 and 6 of glucose. At a simple level of understanding, fractional glucose production from gluconeogenesis, can be understood from the incorporation of deuterium into glucose due to gluconeogenesis. As such, Mass Fragmentography can be useful in diagnosing gross changes in physiological process as occurs during a meal, after an overnight fast, or after an extended fast or starvation.

Using Body Mass to Estimate Isotopic Enrichment of Deuterium in Body Water following Administration of $D_2O$, Heavy Water Given that the total volume of body water is a percentage of the total body weight, a more precise measurement can be made using the average deuterium enrichment and estimating the enrichment in body water based on the dosage of $D_2O$ (e.g., 3 g/kg) and the percent of body water of the individual or patient. Established using gender, weight, height, age and other factors, calculations can be made that are empirically tested and thus yield good approximations. For example, using the estimation that an adult man is 65% water by total weight and a 3 g/kg dose of $D_2O$ would enrich the body water pool to 0.46%.

Using Isotomics, Mass Fragmentography to Estimate Isotopic Enrichment of Deuterium in Body Water following Administration of $D_2O$, Heavy Water With invention of the diagnostic technique described here using multiple fragments of a glucose molecule, measurement of body water enrichment can be made comparing multiple mass fragments in a single mass spectrum from a single biological sample after dosing with $D_2O$. Properly, a measurement of body water enrichment can best be made when % GNG (fGNG) is high and the incorporation of deuterium at C2 of glucose following $D_2O$ dosing is in equilibration with body water. For instance, measurement after an overnight fast will yield a closer approximation in subjects than after a meal is consumed and % GNG is low because of exogenous glucose appearance (EGA). As shown below, EGA can have significant effects on glucose Ra and % GNG. None-the-less, after feeding endogenous glucose Ra and % GNG can only be calculated after corrections for enteral and parenteral nutrition (i.e., EGA). Hence, using a single mass spectrum and fragmentography it is possible to determine the product/precursor ratio, and hence % GNG in a single assay.

Effects of Body Water Turnover on $D_2O$ Isotopic Enrichment and the Calculation of % GNG using Isotomics, Mass Fragmentography Due to the large volume of body water, exogenous dilution of the deuterium body water from a bolus of deuterium oxide can be estimated and will be relatively small as a typical recommended consumption of 3.7 liter (L) per day would dilute the deuterium enriched body water around 8.25% a day. While there are no specific water intake guidelines, the IOM makes general fluid intake recommendations based on survey data and publish Adequate Intake ($A_1$) values from the US Dietary Reference Intakes (DRI). Guidelines for men are 3.7 L per day of total fluid intake of total water from all foods and beverages, and for women the recommendation is 2.7 L per day however actual amounts vary across age, gender and other considerations (Drewnowski, Rehm et al. 2013). Water content in food is only 20% of the total recommendations of water, but this source of water will dilute the deuterium enrichment of body water from a bolus of $D_2O$ the same as water in beverages including water, beer, coffee, etc. The example using a bolus of deuterium oxide equal to 3 g/kg would result in an initial estimated deuterium body water enrichment of 0.46% that would dilute, by actual consumption of total fluid intake, and continue to dilute as daily consumption of fluids continues. However, a constant infusion of deuterium oxide can be ingested or infused at a rate to maintain a specific enrichment of deuterium in body water. In a hospital setting a precise estimation of body water enrichment and an estimation of dilution or a constant infusion of sufficient enrichment can be precisely controlled, maintained and measured for the duration of hospitalization. An alternative approach to continuous $D_2O$ infusion by adding $D_2O$ to fluids supplied to patients is described below.

Similar to healthy adults, infants, children, pregnant women, aging populations and the acute and chronic critically ill and injured have recommendations for daily fluid intake, and therefore deuterium oxide boluses resulting in body water enriched with deuterium in a small percentage of the total will be affected by fluid intake. As well, the deuterium enrichment in body water can be maintained using a constant infusion or ingestion of a percentage of $D_2O$ label as a percentage equal to the desired body water enrichment by estimating the dietary intake of water in all food or beverages based on the patient's or individual's specific needs.

Underlying glucose concentration is the production of glucose from the available endogenous and dietary nutrients. When the body is fully fed, the production of glucose comes primarily from exogenous, dietary sources that enter the systemic circulation via intestinal absorption. For a healthy or other awake person this means dietary CHO intake from taking food; for a comatose or other individual unable to eat, this means enteral and/or parenteral nutrition, or both enteral and parenteral nutrition that results in exogenous glucose appearance (EGA). For the purpose of understanding the underlying roles of hepatic glucose production (HGP) and EGA in relationship to the measurement of body water enrichment when deuterium incorporation is in equilibrium with C2 of glucose, a measurement using ion ratios of m/z 169, 170, 331 and 332 of the penta-acetate derivative of glucose can be established:

$$(332/331+332)-(170/169+170)=(\text{True body water IE})*(HGP/(HGP+EGA)$$

Otherwise stated: With a patient supported nutritionally by the attending health care professional (physician, nurse, dietitian or other) with precise oral, enteral or parenteral prescriptions for feeding, a value for the exogenous caloric intake can be included to indicate EGA using isotomics and mass fragmentography.

A measurement of exogenous carbohydrate support to indicate EGA and abundances of SIM of ions m/z 169, 170, 331 and 332 of the penta-acetate derivative of glucose can indicate a difference in the true body water enrichment, as measured in a fasting state, to the absorption rate of exogenous glucose using the expression describe above and repeated here:

$$(332/331+332)-(170/169+170)=(\text{True body water IE})*(HGP/(HGP+EGA)$$

Many advantages of isotomics, mass fragmentography exist including simultaneous measurements of flux, concentration and fractional production in a single biological sample analyzed by a single mass spectrum.

Isotomics allows physiological insight in the form of flux of organisms. With the understanding that certain biological pathways derive their molecular structure due to anabolic and catabolic physiologic function as it relates to organism survival under adverse environmental situations including healthy and injured states. A healthy state includes refueling the organism with dietary intake of nutrients. Using isotomics enables the basic researcher or medical professional to differentiate the biological pathway consumed and integrated molecules for micro and macro nutrient survival. Using a tracer can transition understanding from static, homeostasis of glucose, to glucose production, a measurement of flux that satisfies the molecular repository for biosynthesis. Glucose being a biological priority is therefore redundantly supported in the organism through consumption of dietary nutrients and real-time production from glycogen and gluconeogenesis. Predominately dietary glucose supports glucose production through glycolysis and gluconeogenesis as the major gluconeogenic precursor is lactate, and lactate is the end product of glycolysis. However, lipids, amino acids, and ketone bodies contribute to the source of nutrients for glucose homeostasis through gluconeogenesis as well. Because this homeostasis is a biologic priority concentration is largely maintained through exquisite glycemic control and therefore [glucose] is not necessarily the best biomarker for glucose homeostasis since it is the underlying flux of the organism that produces glucose and establishes [glucose].

Isotomics, the anatomy of a molecule through the physiological pathways for energy production will enhance medical discovery and guide physicians to prescribe precision medicine to individual patients. This includes glycolysis and maintenance of glucose production, but also includes enzymatic and protein transporter activity. Some examples of protein transport include the systems of the Lactate Shuttle. For example, monocarboxylate transport (MCT) protein activity (flux) can be monitored using isotomics to understand the rates of turnover of a single protein or the interactome of a complex of proteins or a proteome by isotomics, mass fragmentography analysis of a protein like MCT as the increase and decrease in flux rates determined by activity as well as during injury and illness. Similar to isotomics of fractional gluconeogenesis, MCTs can be analyzed in a precursor product relationship, or within a single mass spectrum in which the fragments of the mass spectrum when taken as individual pieces of a metabolic pathway elucidate the endogenous production and utilization of a process of an organism in flux.

Some potential application for clinical use might be the flux rates of metabolites through a complex of transport proteins (i.e., the fluxome) as the metabolites and their respective transporters interact (i.e., the interactome) to facilitate metabolic processes. Examples of medical applications using isotomics to measure these processes (fluxome and interactome) will be cancer research. As well, in the acute phase of injury or illness, the flux of metabolites through their respective transporter networks that facilitate glucose production from glycogenolysis and gluconeogenesis can be used as biomarkers of the individual metabolic and energy state of the individual or patient, i.e. the body energy state (BES) can be more fully interpreted by measuring multiple components of the metabolic processes.

Signaling molecules, like lactate and beta hydroxy butyrate, can be labeled or affect the labeling pattern of the molecules that make up the energy substrates, enzymes or protein transporters and therefore the molecular anatomy, determined by positional isomers of the atoms of the molecule (either labeled or non-labeled) can be determined through isotomics.

Another embodiment where isotomics, the anatomy of the molecule, mass fragmentography and fluxomics intersect is described through the signaling of G-protein coupled lactate receptor (GPR81, aka Hydroxy Carbolic Acid Receptor1, HCAR1) and beta hydroxybutyrate receptors) GPR 109 a and b). Stimulation of GPR81 and GPR109 by physiological concentrations of lactate or beta hydroxybutyrate, respectively, in combination with or without tracers, can be measured. With a thorough understanding of the anatomy of the molecules involved (with respect to signaling and signaled molecule similar to precursor product relationships), and with or without the aid of tracers, metabolic pathways can be understood. As well, when the flux rates through diverse metabolic pathways change when individuals transition from a healthy to injured state, or from rest to exercise, isotomics will enable real-time measurements of flux. An understanding of the flux-interaction between signaling and signaled molecules can indicate the body energy state of a mammal. As well, formulations with compositions determined to signal the receptor specifically for the desired physiological outcome such as HCAR1 (GPR81), GPR 109a and 109b, BDNF, TREK1, etc., are possible with the invention.

Signaling molecules can exist locally at tissue specific sites. In adipose tissue lactate signaling occurs due to insulin-dependent uptake of glucose. Similar glycolytic activity exists in the brain. Other brain specific signaling sites include TREK1 acting at high physiological ranges of lactate concentration (>30 mM) for potassium channel activity and neuroprotection.

Clamp therapy as a signaling mechanism for inflammasome. The administration of lactate that targets low (0.5-1.0 mM) to high (>5 mM) acts as an anti-inflammatory agent. The combination therapy of nutrition and anti-inflammation of lactate clamp therapy can be applied to multiple indications for use. As well, in combination with other agents such as ketones, energy and signaling can simultaneously occur as ketones are known to reduce seizures in epileptics and signal membrane proteins.

Ketone Clamp—target blood, breath, sweat, urine (i.e., biological sample) BOHB concentration from exogenous administration of nutritional formulations. BOHB is a monocarboxylate that naturally occurs and fluctuates as part of normal and pathophysiology. Blood concentrations of ketones depend on the metabolic and nutritional status of an individual. The normal blood concentration range of BOHB is about 0.1-0.2 mmol/L; and, after a 12 hour fast blood BOHB concentration range rises to 0.4 to 0.5 mmol/L (Zinker, Britz et al. 1990). As well, blood BOHB concentrations about 3 mmol/L are physiologically possible (Clarke, Tchabanenko et al. 2012). Thus, an elevated blood BOHB concentration indicates that the metabolic and nutritional state of a healthy individual who is insufficiently fed. Moreover, errors in carbohydrate and lipid metabolism cause blood ketone levels to rise in "poorly controlled" diabetics. Interestingly, while blood ketone levels are elevated in healthy, but inadequately fed persons, regardless of previous dietary history, it is possible to nourish inadequately fed persons by administering a high-ketone or high-fat diet (Prins and Matsumoto 2014). Importantly, if cerebral nutrition is of concern, because ketones share cerebral monocarboxylate transporter (MCT) proteins with lactate and pyruvate (Roth and Brooks 1990, Roth and Brooks 1990, Prins and Giza 2006), a "ketogenic diet" (i.e., one giving rise to elevated blood ketone levels) or exogenous administration of BOHB or salts of BOHB has the potential to nourish body and brain (Brooks and Martin 2014). In a healthy, non-diabetic person biological (e.g., blood) ketone levels can be raised not only by administration of a formulation containing BOHB, or acetoacetate, but also a high fat diet containing mono-, di-, or triglycerides containing short-, medium- or long-chain fatty acids can raise blood BOHB concentration. Thus, a target range of BOHB in a healthy, non-diabetic person being supplemented by exogenous ketone formulation or high fat diet is a blood BOHB greater than 0.2 mmol/L and less than about 3 mmol/L. Accordingly, the determination of the concentration of BOHB of about 0.4 mmol/L determines whether to increase, decrease, maintain or cease administration of a nutritional formulation. Thus, a personalized target of BOHB concentration around 0.2 mmol/L to 0.5 mmol/L resulting from administration of a ketogenic nutritional formulation indicates the metabolic and nutritional status of an individual and results in supplemental nutrition when considered on the broader context of overall nutritional adequacy. Targeting the individual's specific BOHB concentration range for nutritional adequacy is in sharp contrast to the current standard of care dosing of nutrition where the dose is standardized by body weight and regression-to-mean equations that cannot take into consideration the variability of the energy substrate flux rates giving rise to an individual's unique metabolic and nutritional states.

Lactate clamp for the treatment of inflammation (inflammatory disorders) including other biomarkers of interest such as inflammatory proteins, combination of an array of inflammatory proteins and physiological metrics as defined by systemic inflammatory response syndrome (SIRS).

Treatment of inflammation using a lactate measuring device to target lactate concentration above about 2 mM using exogenously administered pharmaceutical or nutraceutical compounds or formulations and measuring and targeting other biological markers of inflammation such as interleukin (IL)-6, serum TNF-alpha, IL-1B (i.e., serum cytokines), C-reactive protein (CRP), serum Alanine aminotransferase (ALT) or Glutamate Pyruvate transaminase (SGPT), serum albumin, serum prealbumin, (transthyretin), retinol-binding protein, transferrin, lymphocytes, serum procalcitonin (PCT).

Measuring of physiological markers of inflammation usually includes collecting blood, serum, plasma or other biological samples and employing techniques common in the scientific and medical fields. Agencies such as the Centers for Disease Control (CDC) and Food and Drug Administration (FDA) as well as others give guidelines with respect to assay the sample including preparation of samples, analysis and interpretation of biomarkers of inflammation. For example, an online searchable Guidance Document from the FDA exist to guide in-vitro diagnostic (IVD) immunological test systems for approval for Conventional C Reactive Protein (CRP) and derivatives (e.g., High sensitivity CRP (hsCRP), Cardiac C-Reactive Protein (cCRP) (U.S. Food and Drug Administration).

Combining lactate clamp therapy and determination of CRP and other physiological biomarkers of interest for inflammation and other indications for use necessitates the assaying, measuring, determining or receiving values of the biomarkers of interest and administering, increasing, decreasing, maintaining or ceasing nutrition to achieve the target concentrations. For example, when a patient is assessed for inflammatory disorders, one or more biomarkers of inflammation will be determined and lactate clamp therapy will be administered. The therapy will continue with periodic (or continuous) measurement of the biomarkers of interest and periodic (or continuous) adjustment of administration of nutrition.

Conventional CRP assays test values are typically considered to be clinically significant at levels above 10 mg/L. In healthy individuals blood CRP levels are below 5 mg/L, while in various conditions this threshold is often exceeded within four to eight hours after an acute inflammatory event, with CRP values reaching approximately 20 to 500 mg/L High sensitivity CRP (hsCRP) assays measurement range extends below the measurement range of conventional CRP assays. A lower range of measurement of CRP facilitated by the hsCRP assay may expand the indications for use to include otherwise healthy individuals but indications for hsCRP assays not associated with specific diseases or risks for disease.

Cardiac C-Reactive Protein (cCRP)) is indicated for use for individuals at risk of future cardiovascular disease and like hsCRP extend the measurable range below conventional CRP measurements.

According to FDA Guidance Document, use of the three CRP biomarkers of inflammation are as follows: 1) "Conventional CRP: For evaluation of infection, tissue injury, and inflammatory disorders. Provides information for the diagnosis, therapy, and monitoring of inflammatory disorders. Cutoff: approximately 10 mg/L. Apparently healthy individuals: less than or equal to 5 mg/L Acute range: 20-500 mg/L. 2) hsCRP: For evaluation of conditions thought to be associated with inflammation, in otherwise healthy individuals. Cutoff: s 1.0 mg/L and 3) cCRP: For aid in identification and stratification of individuals at risk for cardiovascular disease. When used in conjunction with traditional clinical laboratory evaluation of acute coronary syndromes, cCRP may be useful as an independent marker of prognosis for recurrent events, in patients with stable coronary disease or acute coronary syndrome. Cutoff: s 1.0 mg/L"

Additional protein biomarkers of inflammation can similarly be used in combination with lactate clamp therapy as CRP. For example lactate clamp therapy and a panel of inflammatory protein biomarkers including one or more of interleukin (IL)-6, serum TNF-alpha, IL-1B (i.e., serum cytokines), serum alanine aminotransferase (ALT or SGPT), serum albumin, serum prealbumin (transthyretin), retinol-binding protein, transferrin, lymphocytes, serum procalcitonin (ProCT) can be used alone or in combination including with CRP, SIRS or other biomarkers of inflammation as they continue to be discovered and utilized in healthy and injured and ill individuals.

Other protein biomarkers, like CRP, are routinely assayed in the scientific and medical fields and guidance documents exist for the approval of such diagnostics through scientific publications and agencies such as the FDA. Although concentrations of serum cytokine ranges depend on age of subject and indication for use have clinical utility.

Protein ranges in a study comparing a group<45 years versus a second group>65 years show IL-6 concentrations were 2.91±6.45 pg/ml versus 2.57±5.22 pg/ml, respectively.

TNF-alpha ranges in the same study were 3.21±4.04 pg/ml and 4.94±4.78 pg/ml in the <45 versus>65 age groups, respectively.

IL-1B ranges in the same study were 2.04±4.93 pg/ml and 2.52±7.41 pg/ml in the <45 versus>65 age groups, respectively.

Another reference guideline indicates serum alanine aminotransferase normal range, which is measured in international units/liter, is 10-40 IU/L.

Another reference guideline of the normal range of human serum albumin in adults (age>3 yr) is 3.5 to 5 g/dL. For children less than three years of age, the normal range of human serum albumin is 2.9 to 5.5 g/dL.

Another reference guideline of the normal range of serum prealbumin (transthyretin) concentration range is 16 to 40 mg/dL.

Another reference guideline of the normal range of Retinol-binding protein range is 3 to 6 mg/dL.

Another reference guideline of the normal range of transferrin is 200 to 320 mg/dL.

Another reference guideline of the normal range of procalcitonin (ProCT) in adults and children> or =72 hours is < or =0.15 ng/mL. Children<72 hours the normal ProCT range is <2.0 ng/mL at birth and rises to < or =20 ng/mL at 18-30 hours of age, then falls to < or =0.15 ng/mL by 72 hours of age.

Treatment of inflammation using a lactate measuring device to target lactate concentration above about 2 mM using exogenously administered pharmaceutical or nutraceutical compounds or formulations and measuring and targeting other biological markers of inflammation such as systemic inflammatory response syndrome (SIRS).

SIRS is routinely used in the clinical setting to determine systemic inflammation, and can be used with lactate clamp therapy and other biomarkers of interest such as an individual protein or panel of proteins.

Diagnosing SIRS includes body temperature less than 36° C. (96.8° F.) or greater than 38° C. (100.4° F.), heart rate greater than 90 beats per minute, tachypnea with greater than 20 breaths per minute (or, an arterial partial pressure of carbon dioxide less than 4.3 kPa (32 mmHg), white blood count less than 4000 cells/$mm^3$ ($4\times10^9$ cells/L) or greater than 12,000 cells/$mm^3$ ($12\times10^9$ cells/L); or the presence of greater than 10% immature neutrophils (band forms). When two or more of these metrics exceed given values, with or without evidence of infection, patients may be diagnosed with SIRS. If patients with SIRS also present with acute organ dysfunction they may be termed severe SIRS.

Protein and physiological biomarkers indicated in the embodiments of the invention are used as examples of treating inflammation, but they are also used in other indications for use and are not limited to the treatment of inflammation alone.

Inflammatory disorders include but are not limited to acute pancreatitis, hepatitis, sepsis.

Treatment of inflammation using ketone clamp therapy and biomarkers of inflammation Ketone clamp therapy using measuring device to target ketone BOHB concentrations above about 0.1-0.2 mmol/L and exogenously administered pharmaceutical or nutraceutical compounds or formulations, and measuring and targeting other biomarkers of interest can be combined alone with, for example, SIRS or in combination with other biomarkers of interest such as an individual protein, an individual protein and SIRS, a panel of proteins, or panel of proteins and SIRS. As diagnostic test continue to become more available, it will be common to combine panels of analytes, as described, to improve diagnosis and treatment and specificity of clinical utility will improve when a panel of two, three or more analytes (i.e., physiological biomarkers, or biomarkers of the body and brain energy state) are used together for personalized diagnosis, treatment, and periodic (or continuous) feedback.

Clamp Therapies including lactate, ketone and other metabolites of interest can be used alone or in combination with formulations and measuring devices to treat the injured and ill as well as provide precision nutrition to the health.

Treatment of neurological disorders and stroke using clamp therapy and a single or panel of physiological biomarkers: Similar to using lactate clamp therapy for inflammation wherein lactate concentration is targeted and single or panel of physiological biomarkers are target by adjusting the administration of nutritional compounds or formulations, clamp therapy can be used for the assessment and treatment of neurological disorders.

Protein biomarkers of neurological disorders and stroke can include the proteins described for inflammation as well as SIRS and other physiological biomarkers as well as brain specific proteins biomarkers. These brain specific protein biomarkers can also be used to diagnose and treat and periodically (or continuously) reassess patient status and include serum biomarker concentrations for Brain-Derived Neurotrophic Factor (BDNF), Glial Fibrillary Acidic Protein (GFAP), Metallothionein 3 (MT3), Neurogranin (NRGN), Neuron Specific Enolase (NSE), Beta-Synuclein (SNCB) and Ubiquitin carboxy-terminal hydrolase L1 (UCHL1).

Reference guideline of the normal range of Brain-Derived Neurotrophic Factor (BDNF) is 8 to 46 ng/ml, with an average around 18 to 26 ng/ml and generally not beyond a minimum of 3 and a maximum 80 ng/ml Reference guideline of the normal range of Glial Fibrillary Acidic Protein (GFAP) is about 0.014 micro gram/L to 18 micro gram/L.

Reference guideline of the normal range of Metallothionein 3 (MT3) is about 0.15 to 10 ng/mL.

Reference guideline of the normal range of Neurogranin (NRGN) is about 18.75 ng/ml to 1200 ng/ml.

Reference guideline of the normal range of Neuron Specific Enolase (NSE) is about 5 ng/ml to 200 ng/ml.

Reference guideline of the normal range of Beta-Synuclein (SNCB) is about 25 pg/ml to 1600 pg/ml.

Reference guideline of the normal range of Ubiquitin carboxy-terminal hydrolase L1 (UCHL1) is about 78 pg/ml to 5,000 pg/mL.

Neurological disorders include but are not limited to: brain damage (frontal lobe, parietal lobe, temporal lobe, occipital lobe), spinal cord (injury and inflammation), peripheral neuropathy, cranial nerve disorder, autonomic nervous system disorders, seizures, movement disorders (such as Parkinson's disease, amyotrophic lateral sclerosis, Tourette's Syndrome, multiple sclerosis, and various types of peripheral neuropathy), sleep disorders, migraines and other types of headaches (such as cluster and tension), lower back and neck pain, central neuropathy, neuropsychiatric illnesses diseases and/or disorders with psychiatric features associated with known nervous system injury, underdevelopment, biochemical, anatomical, or electrical malfunction, and/or disease pathology e.g., attention deficit hyperactivity disorder, Autism, Tourette's syndrome and some cases of obsessive compulsive disorder as well as the neurobehavioral associated symptoms of the nervous system such as Parkinson's disease, essential tremor, Huntington's disease, Alzheimer's disease, mild cognitive impairment, multiple sclerosis and organic psychosis, Delirium and Dementia such as Alzheimer's disease, Dizziness and Vertigo, Stupor, Coma, Head Injury (mild, moderate and severe Traumatic Brain Injury), Stroke (CVA, cerebrovascular attack), Tumors of the nervous system, Multiple Sclerosis, Infections of the brain (meningitis), Prion disease, depression, concussion, memory, etc.

Clamp therapy with a panel of analytes including lactate, glucose, physiological salts, fGNG, etc. for companion diagnostic/therapeutic for personalized/precision prescriptions for nutrition and signaling.

Clamp therapy to normalize the Lactate/Pyruvate ratio (L/P, or LPR). Although typically misunderstood in terms contemporary physiology and biochemistry the LPR has been interpreted by clinicians to mean inadequate tissue oxygenation, and hence severity of injury due to a "metabolic crisis" (*Vespa*, Boonyaputthikul et al. 2006). Under this paradigm, even though CMR of glucose is diminished after cerebral injury (Glenn, Kelly et al. 2003, Glenn, Martin et al. 2015), the erroneous assumption is that endogenous cerebral glycolysis will produce pyruvate that is reduced to lactate if cerebral oxygenation is insufficient or if mitochondrial dysfunction is a consequence of injury. The interpretation that elevated [lactate] and LPR are attributable to inadequate tissue respiratory capacity is an entrenched dogma. Despite successes of clinicians to maintain cerebral blood flow and tissue oxygenation after TBI, [lactate] and LPR continue to be disrupted. Still, if there is clinical interest to decrease LPR to a value of 15 or less (the normative value being 10), two approaches are available: (1) infuse pyruvate into the carotid artery, or (2) infuse lactate into a peripheral or central vein.

In porcine models Mallet and colleagues (Sharma, Knott et al. 2005) have shown that pyruvate infusion reduces the systemic LPR. However, in the systemic circulation pyruvate is rapidly converted to lactate due to the effects of lactate dehydrogenase in red blood cells and the lung parenchyma (Johnson, Hussien et al. 2011). Hence, for the antioxidant properties of pyruvate (Mallet and Sun 2003), the optimal site of pyruvate infusion would be in the carotid artery or ascending aorta.

In human experimentation now under way (Thomas Glenn, personal communication) systemic sodium lactate infusion to target a 4 mM blood [lactate]decreases cerebral LPR. This interpretation is not understandable using traditional concepts of biochemistry, but is understandable according to the mitochondrial-to cytosolic lactate to pyruvate shuttle idea of Passarella and colleagues (Passarella, Paventi et al. 2014). A variation on the Intracellular Lactate Shuttle mechanism (Brooks 2002) mitochondrial lactate uptake can result in partial oxidation and export of pyruvate thus decreasing the apparent LPR as measured with blood or cerebral microdialysis.

Fractional production measurements can always be combined with concentrations measurements using internal or external standards known in the art. For example, a biological sample can be obtained and a single or panel of fractional production analytes can be measured in addition a single or panel of analyte concentrations can be obtained from the same sample and from the same (single) analysis.

Closed loop and hybrid closed loop systems for automation of measuring and delivery of formulations to support the body energy state (BES) of individuals.

Systems and networks of information sharing wherein the information acts as a feedback loop to measure, describe and take action on a system is called a closed loop. While the components of such a system can be described individually (e.g., diagnostic, device, formulations, infusion pump, software and data), in aggregate they can be assembled to perform life-saving activities as a fully automated closed loop system, or a hybrid closed loop system.

A closed loop system for precision nutrition can include a diagnostic measurement based on biosensor feedback of an individual's metabolic and nutritional status, an infusion device and a nutritional formulation that is regulated to supply nutrition to a healthy or ill or injured person or other mammal. If provided voluntarily to a conscious person the nutritional formulation can be a nutraceutical that is regulated as a food, medical food, or dietary supplement. Alternatively, if given intravascularly to meet a specific indication for use, the formulation will be regarded as a drug by regulatory agencies such as the FDA.

Developing a hybrid closed loop system would represent a phased approach to developing and commercializing a fully automated closed loop system wherein a component of competent human intervention is automated. Competent human intervention is a concept that explains the role of a clinician as the authority to providing medical care when such care is to improve health of a patient. Any automation that lessens the competent human intervention such as with a hybrid closed loop or fully automated closed loop system is subject to regulatory, FDA, scrutiny over issues related to safety and efficacy of any device, drug or mode of treatment. As a result, automating any aspect of the clinician's judgment or mode of practice in meeting a patient's needs reaches the highest order of clinician, device manufacturer and regulatory concern.

An example of a first step to creating a closed loop system would be to use a point of care or other biosensor as a complementary device to monitor the response to SOC delivery of a nutrient or drug formulation to a patient and then, depending on biosensor results, use competent human intervention to adjust delivery rate of nutrient or drug delivery to the patient. Such a closed loop system would have the intention of increasing precision in nutrient or drug delivery to ill or injured person or other mammal.

An example of a first step to creating a hybrid closed loop system would be to embed an algorithm into an infusion device that would alter infusion rates automatically from interpretation of the results of biomarker feedback through the receiving of metabolic and nutritional diagnostics based on the individual's metabolic and nutritional status. Such a hybrid closed loop system would then provide precision in nutrient delivery to ill or injured person or other mammal.

An example of a first step hybrid closed loop system for lactate clamp therapy would be to provide biomarker feedback on blood lactate concentration measured in an individual who is receiving nutritional support and then utilizing that information to adjust the infusion rate (administration) of the nutritional support to match the metabolic and nutritional needs of the individual and thus support their unique body energy state. With respect to competent human intervention, the clinician can use an algorithm to manually adjust the infusion rate that is appropriate for the patient's treatment. Another embodiment of the hybrid closed loop system using a lactate clamp would be to automate the infusion rate automatically using an embedded software system in the infusion device that increases, decreases, ceases or maintains the delivery of the nutritional formulations based on the biosensor feedback.

A fully automated closed loop system would automate the entire process such that a clinician would not be required to manually adjust the infusion rate of the nutritional formulation.

Another example of using closed loop systems would be to transmit or receive the results of the biosensor and infusion rate results through an information network such as a LAN or Cloud. The information transfer would enable a clinician such as the attending physician, clinical dietitian, nurse, pharmacist or other to receive the patient's data and change the prescription of the patient based on the feedback from the hybrid closed loop or fully automated closed loop automating the delivery of nutritional formulations to support the individual's body energy state. Feedback from the patient's closed loop system to this second, information closed loop system would enable record keeping and prescriptions to be made and shared across several divisions of the hospital to better treat and monitor the patient.

Automated and Software Implementations

It will be appreciated that many of the described methods can be intermediated and implemented automatically by a computer, or special-purpose hardware, or some combination of both, as such systems are well known in the art. Readings could automatically be stored in databases or computer memory and presented to users in various visual forms. The software could also make recommendations as to feeding protocols and times, in human-readable instructions or some sort of automated protocol such as dispensing.

The invention as such can be implemented on any suitable computer system. A typical, general purpose computer system suitable for implementing the present invention includes any number of processors that are coupled to memory devices including primary storage devices such as a read only memory, random access memory and hard drives. Any one of many data and database architectures can be used to store and retrieve methods, protocols and recommendation, to store data, and to communicate with server-side assistance through the Internet and other networks.

A hardware system may be specially constructed for the required purposes, or it may be a general-purpose computer, such as a server computer or a mainframe computer, selectively activated or configured by a computer program stored in the computer. The processes presented above are not inherently related to any particular computer or other computing apparatus. In particular, various general-purpose computers may be used with programs written in accordance with the teachings herein, or, alternatively, it may be more convenient to construct a more specialized computer system to perform the required operations.

Such a general-purpose computer system suitable for carrying out the processing in accordance with one embodiment of the present invention can be a server computer, a client computer, or a mainframe computer. Other computer system architectures and configurations can be used, made up of various subsystems described below, includes one or more microprocessors (or central processing units). Using instructions retrieved from memory, the microprocessor controls the reception and manipulation of input data, and the output and display of data on output devices.

With regard to the present invention, the many features and advantages of the present invention are apparent from the written description, and thus, it is intended by the appended claims to cover all such features and advantages of the invention. Further, since numerous modifications and changes will readily occur to those skilled in the art, it is not desired to limit the invention to the exact construction and operation as illustrated and described. Hence, all suitable modifications and equivalents may be resorted to as falling within the scope of the invention.

Various elements of the invention are described as modules implemented as software on a general-purpose computer and others as hardware elements. It should be apparent that in various embodiments of the invention, implementation of software can be executed by embedded hardware, or vice versa, or in some combination of software and hardware. Also, a computer may take the form of an integrated circuit, printed circuit board, handheld computer, or any general-purpose computer without limitation.

Part of the invention may be implemented by a general-purpose computer, embedded circuitry, or some combination of these. The software execution may be accomplished through the use of a program storage device readable by the computer and encoding a program of instructions executable by the computer for performing the operations described above. The program storage device may take the form of any memory known in the art or subsequently developed. The program of instructions may be object code, i.e., in binary form that is executable more-or-less directly by the computer; in source code that requires compilation or interpretation before execution; or in some intermediate form such as partially compiled code and/or a collection of executable library files. The precise forms of the program storage device and of the encoding of instructions are immaterial here.

The invention also contemplates use of computer networks known in the art, including but not limited to, intranets such as corporate networks, local and wide area networks, the Internet and the World Wide Web, and thus use of mobile devices and software applications of such (apps). Wire and wireless communication and communication protocols known in the art, such as, but not limited to, radio, infrared, Bluetooth, Ethernet and other wireless and wired networks, are also contemplated.

Preferred embodiments of flow direction between elements, looping and iteration are discussed, but alternative embodiments of these flows are contemplated by the invention. Any elements or other features described in the figures, even if not described in the specification, are supported in the figures so as to be enabling. All references cited here are incorporated in their entirety for all purposes.

REFERENCES

The below references are useful as background material. Some, but not all, are cited in-line throughout this specification above, and they are not necessarily relevant to patentability of the invention.

Azevedo, J. L., E. Tietz, T. Two-Feathers, J. Paull and K. Chapman (2007). "Lactate, fructose and glucose oxidation profiles in sports drinks and the effect on exercise performance." *PloS one* 2(9): e927.

Bakker, J., M. W. Nijsten and T. C. Jansen (2013). "Clinical use of lactate monitoring in critically ill patients." *Ann Intensive Care* 3(1): 12.

Bergman, B. C., G. E. Butterfield, E. E. Wolfel, G. D. Lopaschuk, G. A. Casazza, M. A. Homing and G. A. Brooks (1999). "Muscle net glucose uptake and glucose kinetics after endurance training in men." *The American journal of physiology* 277(1 Pt 1): E81-92.

Bergman, B. C., M. A. Horning, G. A. Casazza, E. E. Wolfel, G. E. Butterfield and G. A. Brooks (2000). "Endurance training increases gluconeogenesis during rest and exercise in men." *American journal of physiology. Endocrinology and metabolism* 278(2): E244-251.

Bergman, B. C., E. E. Wolfel, G. E. Butterfield, G. D. Lopaschuk, G. A. Casazza, M. A. Horning and G. A. Brooks (1999). "Active muscle and whole body lactate kinetics after endurance training in men." *Journal of applied physiology* 87(5): 1684-1696.

Brooks, G. A. (1984). "Glycolytic end product and oxidative substrate during sustained exercise in mammals—the "lactate shuttle." *Comparative Physiology and Biochemistry—Current Topics and Trends, Volume A. Respiration—Metabolism—Circulation:* 208-218.

Brooks, G. A. (1985). "Anaerobic threshold: review of the concept and directions for future research." *Medicine and science in sports and exercise* 17(1): 22-34.

Brooks, G. A. (2002). "Lactate shuttles in nature." *Biochem Soc Trans* 30(2): 258-264.

Brooks, G. A. (2009). "Cell-cell and intracellular lactate shuttles." *J Physiol* 587(Pt 23): 5591-5600.

Brooks, G. A., G. E. Butterfield, R. R. Wolfe, B. M. Groves, R. S. Mazzeo, J. R. Sutton, E. E. Wolfel and J. T. Reeves (1991). "Decreased reliance on lactate during exercise after acclimatization to 4,300 m." *Journal of applied physiology* 71(1): 333-341.

Brooks, G. A., H. Dubouchaud, M. Brown, J. P. Sicurello and C. E. Butz (1999). "Role of mitochondrial lactate dehydrogenase and lactate oxidation in the intracellular lactate shuttle." *Proc Natl Acad Sci USA* 96(3): 1129-1134.

Brooks, G. A., T. D. Fahey and K. M. Baldwin (2019). *EXERCISE PHYSIOLOGY: Human Bioenergetics and Its Applications*, Kindle Direct Publishing, Lexington, KY.

Brooks, G. A., K. J. Hittelman, J. A. Faulkner and R. E. Beyer (1971). "Temperature, skeletal muscle mitochondrial functions, and oxygen debt." *Am J Physiol* 220(4): 1053-1059.

Brooks, G. A. and N. A. Martin (2014). "Cerebral metabolism following traumatic brain injury: new discoveries with implications for treatment." *Front Neurosci* 8: 408.

Brooks, G. A., E. E. Wolfel, B. M. Groves, P. R. Bender, G. E. Butterfield, A. Cymerman, R. S. Mazzeo, J. R. Sutton, R. R. Wolfe and J. T. Reeves (1992). "Muscle accounts for glucose disposal but not blood lactate appearance during exercise after acclimatization to 4,300 m." *Journal of applied physiology* 72(6): 2435-2445.

Casaer, M. P. and G. Van den Berghe (2014). "Nutrition in the acute phase of critical illness." *N Engl J Med* 370(13): 1227-1236.

Chacko, S. K., A. L. Sunehag, S. Sharma, P. J. Sauer and M. W. Haymond (2008). "Measurement of gluconeogenesis using glucose fragments and mass spectrometry after ingestion of deuterium oxide." *Journal of applied physiology* 104(4): 944-951.

Chance, B. and G. R. Williams (1956). "Respiratory enzymes in oxidative phosphorylation. VI. The effects of adenosine diphosphate on azide-treated mitochondria." *J Biol Chem* 221(1): 477-489.

Clarke, K., K. Tchabanenko, R. Pawlosky, E. Carter, M. Todd King, K. Musa-Veloso, M. Ho, A. Roberts, J. Robertson, T. B. Vanitallie and R. L. Veech (2012). "Kinetics, safety and tolerability of (R)-3-hydroxybutyl (R)-3-hydroxybutyrate in healthy adult subjects." *Regul Toxicol Pharmacol* 63(3): 401-408.

Drewnowski, A., C. D. Rehm and F. Constant (2013). "Water and beverage consumption among adults in the United States: cross-sectional study using data from NHANES 2005-2010." *BMC Public Health* 13: 1068.

Emhoff, C. A., L. A. Messonnier, M. A. Homing, J. A. Fattor, T. J. Carlson and G. A. Brooks (2013). "Gluconeogenesis and hepatic glycogenolysis during exercise at the lactate threshold." *Journal of Applied Physiology* 114(3): 297-306.

Garcia-Alvarez, M., P. Marik and R. Bellomo (2014). "Stress hyperlactataemia: present understanding and controversy." *Lancet Diabetes Endocrinol* 2(4): 339-347.

Glenn, T. C., D. F. Kelly, W. J. Boscardin, D. L. McArthur, P. *Vespa*, M. Oertel, D. A. Hovda, M. Bergsneider, L. Hillered and N. A. Martin (2003). "Energy dysfunction as a predictor of outcome after moderate or severe head injury: indices of oxygen, glucose, and lactate metabolism." *Journal of cerebral blood flow and metabolism: official journal of the International Society of Cerebral Blood Flow and Metabolism* 23(10): 1239-1250.

Glenn, T. C., N. A. Martin, M. A. Horning, D. L. McArthur, D. Hovda, P. M. *Vespa* and G. A. Brooks (2015). "Lactate: Brain Fuel in Human Traumatic Brain Injury. A Comparison to Normal Healthy Control Subjects." *J Neurotrauma.*

Glenn, T. C., N. A. Martin, D. L. McArthur, D. Hovda, P. M. *Vespa*, M. A. Horning, M. L. Johnson and G. A. Brooks (2014). "Endogenous nutritive support following traumatic brain injury: peripheral lactate production for glucose supply via gluconeogenesis." *J Neurotrauma.*

Harris, J. A. and F. G. Benedict (1918). "A Biometric Study of Human Basal Metabolism." *Proceedings of the National Academy of Sciences of the United States of America* 4(12): 370-373.

Homing, M. A. and G. A. Brooks (2012). FORMULATIONS AND METHODS TO PROVIDE NUTRITION TO HUMAN AND OTHER PATIENTS.

Homing, M. A., S. R. Colberg, G. A. Casazza and G. A. Brooks (2000). "Recycling of deuterium from dideuterated glucose during moderate exercise." *Annals of Clinical Biochemistry* 37(Pt 4)(5): 540-542.

Jansen, T. C., J. van Bommel, P. G. Mulder, J. H. Rommes, S. J. Schieveld and J. Bakker (2008). "The prognostic value of blood lactate levels relative to that of vital signs in the pre-hospital setting: a pilot study." *Crit Care* 12(6): R160.

Jeukendrup, A. E., L. Moseley, G. I. Mainwaring, S. Samuels, S. Perry and C. H. Mann (2006). "Exogenous carbohydrate oxidation during ultraendurance exercise." *Journal of Applied Physiology* 100(4): 1134-1141.

Johnson, M. L., R. Hussien, M. A. Homing and G. A. Brooks (2011). "Transpulmonary pyruvate kinetics." *American journal of physiology. Regulatory, integrative and comparative physiology* 301(3): R769-774.

Landau, B. R. (1999). "Quantifying the contribution of gluconeogenesis to glucose production in fasted human subjects using stable isotopes." *The Proceedings of the Nutrition Society* 58(4): 963-972.

Landau, B. R., J. Wahren, V. Chandramouli, W. C. Schumann, K. Ekberg and S. C. Kalhan (1995). "Use of 2H2O for estimating rates of gluconeogenesis. Application to the fasted state." *The Journal of clinical investigation* 95(1): 172-178.

Lecoultre, V., R. Benoit, G. Carrel, Y. Schutz, G. P. Millet, L. Tappy and P. Schneiter (2010). "Fructose and glucose co-ingestion during prolonged exercise increases lactate and glucose fluxes and oxidation compared with an equimolar intake of glucose." *The American journal of clinical nutrition* 92(5): 1071-1079.

Mallet, R. T. and J. Sun (2003). "Antioxidant properties of myocardial fuels." *Molecular and cellular biochemistry* 253(1-2): 103-111.

Millward, D. J., C. T. Davies, D. Halliday, S. L. Wolman, D. Matthews and M. Rennie (1982). "Effect of exercise on protein metabolism in humans as explored with stable isotopes." *Fed Proc* 41(10): 2686-2691.

Passarella, S., G. Paventi and R. Pizzuto (2014). "The mitochondrial L-lactate dehydrogenase affair." *Front Neurosci* 8: 407.

Phillips, S. M. (2012). "Dietary protein requirements and adaptive advantages in athletes." *The British journal of nutrition* 108 Suppi 2: S158-167.

Prins, M. L. and C. C. Giza (2006). "Induction of monocarboxylate transporter 2 expression and ketone transport following traumatic brain injury in juvenile and adult rats." *Developmental neuroscience* 28(4-5): 447-456.

Prins, M. L. and J. H. Matsumoto (2014). "The collective therapeutic potential of cerebral ketone metabolism in traumatic brain injury." *J Lipid Res* 55(12): 2450-2457.

Roth, D. A. and G. A. Brooks (1990). "Lactate and pyruvate transport is dominated by a pH gradient-sensitive carrier in rat skeletal muscle sarcolemmal vesicles." *Archives of biochemistry and biophysics* 279(2): 386-394.

Roth, D. A. and G. A. Brooks (1990). "Lactate transport is mediated by a membrane-bound carrier in rat skeletal muscle sarcolemmal vesicles." *Archives of biochemistry and biophysics* 279(2): 377-385.

Sharma, A. B., E. M. Knott, J. Bi, R. R. Martinez, J. Sun and R. T. Mallet (2005). "Pyruvate improves cardiac electromechanical and metabolic recovery from cardiopulmonary arrest and resuscitation." *Resuscitation* 66(1): 71-81.

Slone, D. S. (2004). "Nutritional support of the critically ill and injured patient." *Critical care clinics* 20(1): 135-157.

Spitzer, J. J. (1979). "Gluconeogenesis in the burned patient." *J Trauma* 19(11 Suppl): 899-900.

Trimmer, J. K., G. A. Casazza, M. A. Horning and G. A. Brooks (2001). "Autoregulation of glucose production in men with a glycerol load during rest and exercise." *American journal of physiology. Endocrinology and metabolism* 280(4): E657-668.

van Rosendal, S. P., M. A. Osborne, R. G. Fassett and J. S. Coombes (2010). "Guidelines for glycerol use in hyperhydration and rehydration associated with exercise." *Sports medicine* 40(2): 113-129.

Vespa, P., R. Boonyaputthikul, D. L. McArthur, C. Miller, M. Etchepare, M. Bergsneider, T. Glenn, N. Martin and D. Hovda (2006). "Intensive insulin therapy reduces microdialysis glucose values without altering glucose utilization or improving the lactate/pyruvate ratio after traumatic brain injury." *Critical care medicine* 34(3): 850-856.

Wallis, G. A., A. L. Friedlander, K. A. Jacobs, M. A. Homing, J. A. Fattor, E. E. Wolfel, G. D. Lopaschuk and G. A. Brooks (2007). "Substantial working muscle glycerol turnover during two-legged cycle ergometry." *Am J Physiol Endocrinol Metab* 293(4): E950-957.

Wasserman, K. and M. B. McIlroy (1964). "Detecting the Threshold of Anaerobic Metabolism in Cardiac Patients during Exercise." *Am J Cardiol* 14: 844-852.

White, T. P. and G. A. Brooks (1981). "[U-14C]glucose, -alanine, and -leucine oxidation in rats at rest and two intensities of running." *Am J Physiol* 240(2): E155-165.

Zinker, B. A., K. Britz and G. A. Brooks (1990). "Effects of a 36-hour fast on human endurance and substrate utilization." *J Appl Physiol* (1985) 69(5): 1849-1855.

What is claimed is:

1. A molecule, as shown:

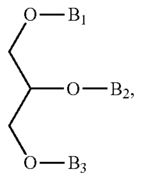

wherein functional group $B_1$ comprises beta hydroxybutyrate, functional group $B_2$ comprises beta hydroxybutyrate and functional group $B_3$ comprises lactate or pyruvate.

2. An aqueous formulation comprising: a molecule, as shown:

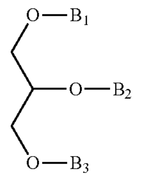

wherein functional group $B_1$ comprises beta hydroxybutyrate, functional group $B_2$ comprises beta hydroxybutyrate and functional group $B_3$ comprises lactate or pyruvate.

3. The formulation of claim 2 further comprising an aqueous nutritional formulation for humans or mammals or both.

4. The formulation of claim 2 wherein the formulation is suitable for administration by one or more of the following: intravenously, enterally, orally.

5. The formulation of claim 2 wherein the formulation is hypertonic.

6. The formulation of claim 2 wherein the formulation is isotonic.

* * * * *